United States Patent
De Cola et al.

(10) Patent No.: US 10,450,423 B2
(45) Date of Patent: Oct. 22, 2019

(54) DISINTEGRATABLE POROUS ORGANOMETALOXYDE MATERIAL

(71) Applicants: Université de Strasbourg, Strasbourg (FR); Centre National de la Recherche Scientifique—CNRS, Paris (FR)

(72) Inventors: Luisa De Cola, Strasbourg (FR); Laura Maggini, Strasbourg (FR); Eko Adi Prasetyanto, Strasbourg (FR)

(73) Assignees: UNIVERSITE DE STRASBOURG, Strasbourg (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days.

(21) Appl. No.: 15/111,506

(22) PCT Filed: Jan. 14, 2015

(86) PCT No.: PCT/EP2015/050605
§ 371 (c)(1),
(2) Date: Jul. 14, 2016

(87) PCT Pub. No.: WO2015/107087
PCT Pub. Date: Jul. 23, 2015

(65) Prior Publication Data
US 2016/0333145 A1 Nov. 17, 2016

(30) Foreign Application Priority Data

Jan. 14, 2014 (EP) .................................. 14151167

(51) Int. Cl.
*A61K 9/00* (2006.01)
*C08G 83/00* (2006.01)
*C08L 101/16* (2006.01)
*A61K 9/51* (2006.01)
*A61K 31/4188* (2006.01)
*A61K 49/00* (2006.01)

(52) U.S. Cl.
CPC .......... *C08G 83/001* (2013.01); *A61K 9/5115* (2013.01); *A61K 9/5192* (2013.01); *A61K 31/4188* (2013.01); *A61K 49/0093* (2013.01); *C08G 83/008* (2013.01); *C08L 101/16* (2013.01)

(58) Field of Classification Search
CPC .................................................... C08G 83/001
See application file for complete search history.

(56) References Cited

U.S. PATENT DOCUMENTS

2006/0223965 A1 10/2006 Trifu

FOREIGN PATENT DOCUMENTS

WO 03102001 A1 12/2003

OTHER PUBLICATIONS

Álvaro et al, Synthesis of Chiral Periodic Mesoporous Silicas (ChiMO) of MCM-41 Type with Binapththyl and Cyclohexadiyl Groups Incorporated in the Framework and Direct Measurement of Their Optical Activity, Chem. Mater., 2004, 16, 2222-2228.*

(Continued)

*Primary Examiner* — Paul W Dickinson
(74) *Attorney, Agent, or Firm* — Cantor Colburn LLP

(57) ABSTRACT

The present invention relates to disintegratable mesoporous silica materials, a method for producing the same, and uses thereof.

25 Claims, 17 Drawing Sheets

Porous material   Pore   Responsively cleavable linker

(56) References Cited

OTHER PUBLICATIONS

Jayasundera, Organosilica Copolymers for the Adsorption and Separation fo Multiple Pollutants, The Journal of Physical Chemistry Letters B, 2005, 109, 9198-9201.*

Brook et al "Sugar-modified silanes: precursors for silica monoliths"; J. Mater. Chem.; 2004; 14; pp. 1469-1479.

Cho et al "Multifunctional peridioc mesoporous organosilicas with bridging groups formed via dynamic covalent chemistry"; Chem. Commun; 2010; 46; pp. 4568-4570.

Taylor-Pashow et al "Mesoporous Silica Nanoparticies with Co-Condensed Gadolinium Chelates for Multimodal Imaging"; Nanomaterials; 2012; 2; pp. 1-14.

Asefa et al "Recent developments in the synthesis and chemistry of periodic mesoporous organosilicas"; Studies in Surface Science and Catalysis; 2002; 141; 1-26.

Bozbas et al "Novel inorganic-organic hybrid polymers to remove heavy metals from aqueous solution"; Desalination and water treatment: science and engineering; DWT; Nov. 1, 2013; vol. 51; No. 37-39; 7208-7215.

Chandra et al "Highly Luminescent Organic-Inorganic Hybrid Mesoporous Silicas Containing Tunable Chemosensor inside the Pore Wall"; Chemistry of Materials; Oct. 1, 2007; vol. 19, No. 22; 5347-5354.

Cheng et al "Diffusion-Based Deprotection in Mesoporous Materials: A Strategy for Differential Functionalization of Porous Silica Particles"; J. Am. Chem. Soc.; 2007; 129; 9674-9685.

Chiu et al "Synthesis and characterization of cubic periodic mesoporpus organosilicas with a high loading of disulfide groups" New J. Chem., Jan. 1, 2011; 35; 489-494.

Ciesla et al "Ordered mesoporous materials"; Microporous and Mesoporous Materials; 1999; 27; 131-149.

Cornelius et al "Systematic extension of the length of the organic conjugated $\pi$-system of mesoporous silica-based organic-inorganic hybrid materials"; Journal of Materials Chemistry; Jan. 1, 2008; 18; 2587-2592.

Davis "Ordered porous materials for emerging applications"; Nature; 2002; vol. 417; 813-821.

De Juan et al "Selective Functionalization of Mesoporous Silica"; Adv. Mater.; 2000; 12; No. 6; 430-432.

De Moraes et al "Silica-titania sol-gel hybrid materials: synthesis, characterization and potential application in solid phase extraction"; Talanta; 2003; 59; 1039-1044.

Furutani et al "Demonstration of RNA N-Glycosidase Activity of a Vero Toxin (VT2 Variant) Produced by *Escherichia coli* O91: H21 from a Patient with the Hemolytic Uremic Syndrome"; Microbiol. Immunol.; 1990; vol. 34 (4); 387-392.

Graffner et al "Synthesis and Enzymatic Hydrolysis of Esters, Constituting Simple Models of Soft Drugs"; Chem. Pharm. Bull.; 1998; 46(4); 591-601.

Grandsire et al "Palladium supported in polyether-functionalized mesoporous silica. Synthese and application as catalyst for Heck coupling reaction"; Appl. Organometal Chem.; Mar. 1, 2010; 24; 179-183.

Grudzien et al "Adsorption and structural properties of channel-like and cage-like organosilicas"; Absorption; 2006; 12; 293-308.

He et al "Thick hybrid silica-zirconia sol-gel film for single-step fabrication of channel waveguide"; Integrated Optics: Devices, Materials and Technologies X; Proceedings of SPIE; 2006; vol. 6123; 130.

Hoffmann et al "Silica-Based Mesoporous Organic-Inorganic Hybrid Materials"; Angew. Chem. Int. Ed.; 2006; 45; 3216-3251.

Hsu et al "DNA targeting specificity of RNA-guided Cas9 nucleases"; Nat Biotechnol; 2013; 31(9); 827-832.

Hu et al "Proposed Oxidative Metabolic Pathay for Polypropylene Glycol in *Sphingobium* sp. Strain PW-1"; Biosci. Biotchnol. Biochem.; Apr. 23, 2008; 72 (4); 1115-1118.

Inagaki et al "An Ordered mesoporous organosilica hybrid material with a crystal-like wall structure"; Nature; 2002; vol. 416; 304-307.

International Search Report; International Application No. PCT/EP2015/050605; International Filing Date Jan. 14, 2015; dated Feb. 2, 2015, 3 pages.

Khalikova et al "Microbial Dextran-Hydrolyzing Enzymes: Fundamentals and Applications"; Microbiology and Molecular Biology Reviews; 2005; 69, 306-325.

Kobayashi et al "Identification of active sites in amidase: Evolutionary relationship between amide bond- and peptide bond-cleaving enzymes"; Proc. Natl. Acad. Sci.; 1997; vol. 94; 11986-11991.

Kruk "Access to Ultralarge-Pore Ordered Mesoporous Materials through Selection of Surfactant/Swelling-Agent Micellar Templates"; Chem. Research; 2012; vol. 45; No. 10; 1678-1687.

Lee et al "Modification of polylactic acid fabric bt two lipolytic enzyme hydrolysis"; Textile Research Journal; 2013; 83 (3); 229-237.

Linssen et al "Mesoporous templated silicates: an overview of their synthesis, catalytic activation and evaluation of the stability"; Advances in Colloid and Interface Science; 2003; 103; 121-174.

Liu et al "Hydrthermally Stable Thioether-Bridged Mesoporous Materials with Void Defects in the Pore Walls"; Advanced Functional Materials; Aug. 1, 2005; vol. 15, No. 8; 1297-1302.

Lopreore et al "The Yrease-Catalyzed Hydrolysis of Thiourea and Thioacetamide"; Archive of Biochemistry and Biophysics; 1998; vol. 39; No. 2; 299-303.

Lu "Biocompatibility, Biodistribution, and Drug-Delivery Efficiency of Mesoporous Silica Nanoparticies for Cancer Therapy in Animals"; Small; 2010; 6(16); 1794-1805.

Rowan et al "Dynamic Covalent Chemistry"; Angew. Chem. Int. Ed.; 2002; 41; 898-952.

Shea et al "Bridged Polysilsesquioxanes, Molecular-Engineered Hybrid Organic-Inorganic Materials"; Chem. Mater.; 2001; 13; 3306-3319.

Shephard et al "Site-Directed Surface Derivatization of MCM-41: Use of High-Resolution Transmission Electron Microscopy and Molecular Recognition for Determining the Position of Functionality within Mesoporous Materials"; Angew. Chem.; 1998; 37; 2719.

Urata et al "Preparation of mesostructured silica-micelle hybrids and their convrsion to mesoporous silica modified controllably with immobilized hydrphobic blocks by using triethoxysilyl-terminated PEO=PPO=PEO triblock copolymer"; J. Mater Chem.; 2001; 21; 3711-3717.

Vallet-Regi et al "A new Property of MCM-41: Drug Delivery System"; Chem. Mater.; 2001; 13; 308-311.

Valtchev et al "Porous Nanosized Particles: Preparation, Properties, and Applications"; Chem. Rev.; 2013; 113; 6734-6760.

Weissleder et al "In vivo imaging of tumors with protease-activated near-infrared fluorescent probes"; Nat. Biotech; 1999; 17; 375-378.

Written Opinion of the International Searching Authority; International Application No. PCT/EP2015/050605; International Filing Date Jan. 14, 2015, dated Feb. 2, 2015, 6 pages.

Yamashita et al "A new ether bond-splitting enzyme found in Gram-positive polyethylene glycol 6000-utilizing bacterium, *Pseudonocardia* sp. strain K1"; Appl Microbiol Biotechnol; 2004; 66; 174-179.

Zhao et al "Triblock Copolymer Synthesis of Mesoporous Silica with Periodic 50 to 300 Angstrom Pores"; Science; 1998; vol. 279; 548-552.

Chen, Xi et al., " Synthesis of novel thiol-functionaiized mesoporous silica nanorods and their sorbent properties on heavy metals", Front. Mater. Sci. 2012, 6(3); pp. 278-282.

"Study of Matrix Polymer Drug Delivery System" (Abstract only), Lin Mei, Chinese Doctoral Dissertations Full-text Database, Engineering, Science, and Technology 1, No. 7, pp. B016-10, published Jul. 15, 2008 (machine English translation of full abstract; professional translation of Section 1.2.1).

* cited by examiner

CTAB: hexadecyltrimethylammonium bromide
TEOS: tetraethyl orthosilicate
Auxiliary Solvent (AS): EtOH, DMF, etc.*

*Conditions to be adapted to the characteristics of the responsively cleavable linker

DISINTEGRATABLE POROUS ORGANOMETALOXYDE MATERIAL

PRIORITY

This Application claims priority to European Patent Application no EP 14151167.5 filed on 14 Jan. 2014, the entire contents of which are hereby incorporated by reference.

FIELD OF THE INVENTION

The present invention relates to disintegratable porous organometaloxide materials, a method for producing the same, and uses thereof.

BACKGROUND OF THE INVENTION

Porous materials, namely mesoporous, microporous, and macroporous materials, are interesting classes of materials useful for various applications. [1] The discovery, in 1992, of periodic mesoporous silica materials denoted M41S or MCM-type having pore sizes 2-10 nm represented a paradigm shift in the synthesis of porous materials.

The materials were prepared in a straightforward synthesis that involved the aqueous phase co-assembly and acid or base-catalyzed hydrolytic poly-condensation of silicate-surfactant micelles followed by removal of the surfactant by thermal or chemical or photochemical post-treatment steps. This synthetic strategy created a silica replica of the templating micelles (a silicatropic mesophase) and represented a new way of creating silica-materials with crystalline mesoporosity, having a pore architecture (i.e., hexagonal, cubic, worm-hole) and pore dimensions (2-10 nm) that were predicted upon the structure and dimensions of the surfactant-directing micelle assembly. Using this synthetic approach the mesopore dimensions could be chemically controlled with angstrom precision. In an extension of this strategy researchers demonstrated that by using tri-block copolymer micelles, involving for example the co-assembly of a polypropylene oxide-β-polyethylene oxide-β-polypropylene oxide mesophase with silicate precursors, as a new and larger dimension templating mesophase, then the mesopore size range of the MCM41 class of periodic mesoporous silica materials, could be boosted to the upper mesoscale range of 10-30 nm to create a class of much larger mesopore silica materials, denoted as SBA periodic mesoporous silica. [2]

It is important to note that the channel walls of all these MCM and SBA classes and structure types of periodic mesoporous silicas were glassy having just short range order, the channel walls lacked structurally well-defined silica sites like those found in zeolites (a class of solids defined as crystalline microporous aluminosilicates), and were found to be devoid of useful channel functionality for perceived applications that could benefit from the size and shape-controlled mesopores and specific adsorption properties of the materials. In other words, while the mesopores in MCM41, MCM48 and SBA materials were monodispersed (single size) and the mesoporosity could be either periodic (hexagonal, cubic) or randomly organized (worm-hole), [3] the material behaved more or less like any other form of porous silica sol-gel type chemistry, exemplified by the well-known classes of materials called xerogels and aerogels, and that contained a random spatial distribution of different diameter mesopores in a glassy silica matrix. Hence the envisioned benefits of this new class of periodic mesoporous silica materials were never really realized in practice, and, to the best of our knowledge, no products or processes have emerged in more than 10 years since their discovery. Tremendous efforts have been devoted to overcome the functionality deficiency of the MCM41, MCM48 and SBA class of mesoporous silica materials by, incorporating other elements into the materials, creating entirely different compositions, crystallizing the constituents of the channel walls, by incorporating useful organic functionality into the materials. [4]

In the context of functionalization two main methods of integrating organic function into periodic mesoporous silica to create hybrid organic-functionalized mesoporous materials have been devised:

A) The first involving the grafting of organo-functionalized alkoxysilanes $RSi(OR)_3$ to the external or internal surface silanol groups SiOH to give the desired organic-functionalized mesoporous materials; with "external" meaning the external wall of the particles and "internal" meaning the channel walls with the functionalization inside the channels. [5] The functional groups can therefore be covalently anchored after the formation of the mesoporous material or incorporated into the template to react inside the channels during the synthesis of the material. Whichever synthetic strategy is used to make these organo-functionalized mesoporous materials with organic groups terminally bound to the walls of the channels, the surfactant template can be removed from the material by thermal or chemical or photochemical post-treatment steps.

B) Another way to functionalize the framework of the porous material involves the use of a silsesquioxane-type silica precursor (exemplified by $(OR)_3SiRSi(OR)_3$) in which the organic function R instead of being present as a terminally bonded group to the alkoxysilane is rather positioned as a "bridging group" between two alkoxysilyl groups. [6] The resulting templated material is called a periodic mesoporous organosilica (PMO) in which the bridging organic group R is exclusively integrated into the silica framework to create organosilica channel walls.

The ability to directly include, in a predetermined fashion, bridging organic groups into the silica walls of a periodic mesoporous silica was pioneered by Inagaki. [7] His work opened the basis for an entirely new class of PMO nanocomposites, synthesized from the "bottom-up" and with "molecular scale" control, and which offered a myriad of envisioned opportunities based upon the ability to utilize organic synthetic chemistry to control the chemical and physical properties of the material.

The ease of functionalization and the versatile morphology manipulation of the PMOs allowed the development of several hybrids, which can likely be exploited to advantage in a number of application areas including but not limited to controlled release of chemicals and drugs, chemical sensing, bioassays, catalysis and separations, to name a few. [8]

There is, however, still some doubt regarding the question of the degradability of this materials. In fact, once exploited the material for a predetermined purpose, degradation/breakdown of the material does not spontaneously occur, sometimes causing the instauration of accumulation issues (i.e. biomedical applications) or the performance of costly, and not always efficient purification procedures to remove the particles from their working environment.

It would be very advantageous to provide a method of producing an entirely new class of hybrid porous organometaloxide (HPO) materials that have all the desired attributes of the PMOs but are able to overcome the degradation issue mentioned above. Thus, one objective of the present invention is to provide a new class of hybrid porous organometaloxide (HPO) materials characterized by a self-destructive behavior, in order to have better control of their fragmentation and dissolution, avoiding, or at least decreasing the risk of accumulation and facilitating elimination.

DEFINITIONS

Figure 1:
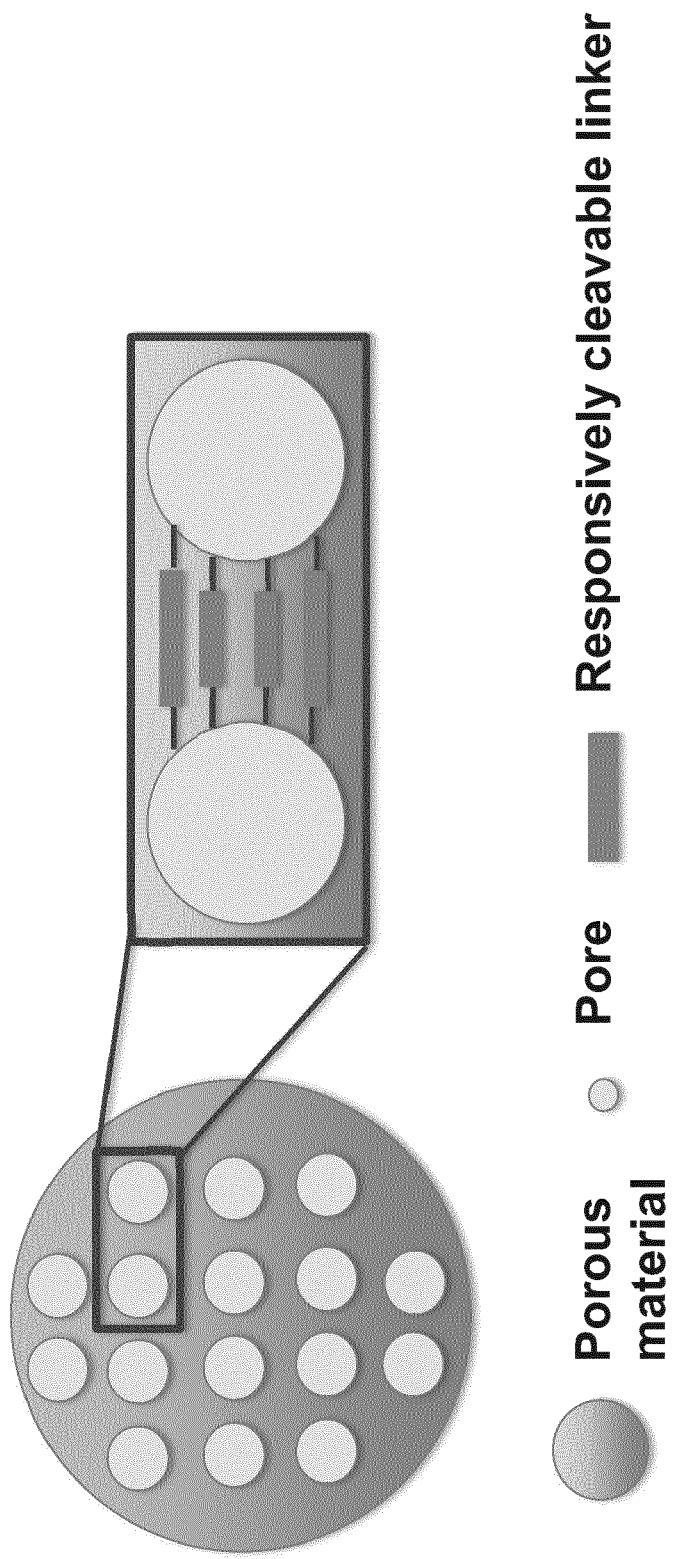
FIG. 1 represents a schematic illustration of the desired structure of the disintegratable porous hybrid organometaloxide material according to the invention, showing the presence of responsively cleavable linkers within the material's framework.

To facilitate an understanding of the present invention, a number of terms and phrases are defined below:

In general, the term "substituted" whether preceded by the term "optionally" or not, and substituents contained in formulae of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds.

As used herein, the term "alkyl", refers to straight and branched alkyl groups. An analogous convention applies to other generic terms such as "alkenyl", "alkynyl" and the like. In certain embodiments, as used herein, "lower alkyl" is used to indicate those alkyl groups (substituted, unsubstituted, branched or unbranched) having about 1-6 carbon atoms. Illustrative alkyl groups include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like. The term "$C_{1-x}$alkylenyl", as used herein, refers to a linear or branched saturated divalent radical consisting solely of carbon and hydrogen atoms, having from one to x carbon atoms, having a free valence "–" at both ends of the radical. Likewise, the term "$C_{1-x}$heteroalkylenyl", as used herein, refers to a linear or branched saturated divalent $C_{1-x}$alkylenyl radical as defined above, comprising at least one heteroatom selected from O, N, or S, and having a free valence "–" at both ends of the radical. When the $C_{1-x}$alkylenyl or $C_{1-x}$heteroalkylenyl is optionally substituted, at least one of the H atoms may be replaced by a substituent such as halogen or —OR where R may represent C1-6alkyl.

The term "ethenylenyl", as used herein, refers to the divalent radical —CH=CH—. When the ethylenyl is optionally substituted, one or both the H atoms may be replaced by a substituent such as halogen or —OR where R may represent C1-6alkyl.

In general, the term "aromatic moiety" or "aryl", as used herein, refers to stable substituted or unsubstituted unsaturated mono- or polycyclic hydrocarbon moieties having preferably 3-14 carbon atoms, comprising at least one ring satisfying the Hackle rule for aromaticity. Examples of aromatic moieties include, but are not limited to, phenyl, indanyl, indenyl, naphthyl, phenanthryl and anthracyl.

The term "halogen" as used herein refers to an atom selected from fluorine, chlorine, bromine and iodine.

As used herein, the term "independently" refers to the fact that the substituents, atoms or moieties to which these terms refer, are selected from the list of variables independently from each other (i.e., they may be identical or the same).

As used herein, the term "template" or "supramolecular template" refers to a self-aggregation of ionic or non-ionic molecules or polymers that have a structure directing function for another molecule or polymer.

As used herein, the term "and/or" means any one of the items, any combination of the items, or all of the items with which this term is associated.

As used herein, the term "about" can refer to a variation of ±5%, ±10%, ±20%, or ±25%, of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a nonlimiting example, each range discussed herein can be readily broken down into a lower third, middle third and upper third, etc.

As will also be understood by one skilled in the art, all language such as "up to," "at least," "greater than," "less than," "more than," "or more," and the like, include the number recited and such terms refer to ranges that can be subsequently broken down into subranges as discussed above. In the same manner, all ratios recited herein also include all subratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes medical, therapeutic, and/or prophylactic administration, as appropriate.

The term "responsively disintegratable", when referring to the porous organometaloxide materials according to the invention, refers to the property of a material or particle that undergoes degradation (i.e., breakdown of the structural integrity of the material or particle) triggered by a particular signal. The signal can be, for example, a change in pH (either an increase or decrease), a change in redox potential, the presence of UV, visible or near infrared light, ultrasounds, electromagnetic radiation, an enzymatic cleavage, a change in temperature, etc. The term "responsively cleavable", when referring to a chemical bond, polymer fragment or linking group, refers to a covalent bond, polymer fragment or linking group that is cleaved upon application of one of the aforementioned particular signals. Generally speaking, the presence of a responsively cleavable bond, polymer fragment or linker moiety within a porous organometaloxide material of the invention, confers to the material its disintegratable properties (the property of structurally breaking down upon application of a specific signal/stimulus, akin to "self-destructive" behavior).

As used herein, the term "periodic mesoporous" refers to having an ordered arrangement of pores in terms of translation symmetry with a diameter between about 2 nm and about 50 nm.

As used herein, the term "mesoporous" refers to having pores with a diameter between about 2 nm and about 50 nm.

As used herein, the term "macroporous" refers to having pores with a diameter between about 50 and about 1,000 nm.

As used herein, the term "mesoporous-macroporous" refers to having two different kinds of pores one of which is between about 2 nm and 50 nm and the other of which is between about 50 nm and about 1,000 nm in the structure.

As used herein, the term "surfactant or block copolymer mesostructure" refers to an ordered supramolecular assembly of surfactant or block copolymer molecule micelles, with translation symmetry between about 2 and about 50 nm.

As used herein, the term "porous framework material" refers to a mesoporous or macroporous or mesoporous-macroporous material in which a $(X_3M_1)R^1\text{-L-}R^2(M_2X_3)$-type responsively cleavable linker is inserted.

As used herein, the term "linker" refers to a responsively cleavable moiety $*\text{—}R^1\text{-L-}R^2*$,

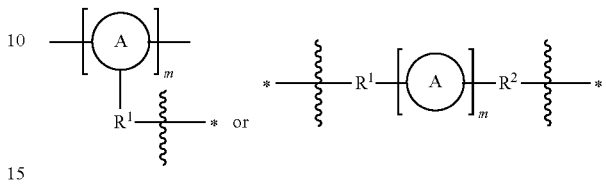

or m inserted into the organometaloxide framework by reaction of a $(X)_3M_1\text{-}R^1\text{-L-}R^2\text{-}M_2(X)_3$ precursor, either

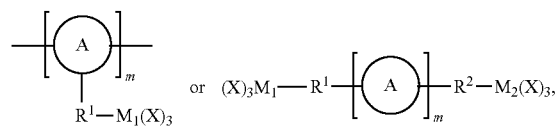

by sol-gel chemistry (hydrolysis or condensation), with the linker being bound to the framework via two or more metal atoms in the framework. In other words, at least one X on each occurrence of $M_1$ and $M_2$ on the precursor is hydrolyzed to lead to formation of the metaloxide framework.

As used herein, the term "cleavable" refers both to the reversible/biodegradable nature of the $*\text{—}R^1\text{-L-}R^2\text{—}*$,

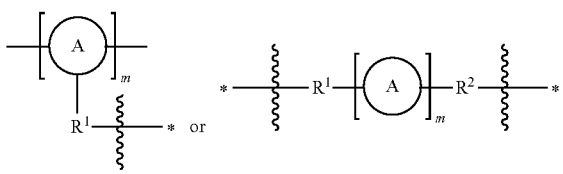

linker, as defined herein, triggering the decomposition/disintegration of the bulk hybrid porous material. As such, the linker may contain a dynamic covalent bond.

As used herein, the term "dynamic covalent bond" refers to any covalent chemical bond possessing the capacity to be formed and broken under equilibrium control.

In this sense, they can be intended as "reversible" covalent bonds. [9]

As used herein, the term "biological polymer" or "biopolymer" refers to polymers produced by living organisms, or synthetic mimics of those. There are three main classes of biopolymers, classified according to the monomeric units used and the structure of the biopolymer formed: polynucleotides (RNA and DNA), which are long polymers composed of 13 or more nucleotide monomers; polypeptides, which are short polymers of amino acids; and polysaccharides, which are often linear bonded polymeric carbohydrate structures.

As used herein, the term "biodegradable polymer" refers to synthetic polymers, which can undergo chemical dissolution by biological means (bacteria, enzymes, etc.)

As used herein the term "organometaloxide" refers to a compound, which contains at least a metal-carbon bond.

As used herein the term "metaloxide" generally refers to metal oxide derivatives, such as silicon oxide derivatives but it could be generalized to other metal oxides, e.g. titanium oxide and zirconium oxide.

DETAILED DESCRIPTION OF CERTAIN PREFERRED EMBODIMENTS OF THE INVENTION

As noted above, there has been increasing interest in recent years in the development porous organometaloxide materials with better degradability.

In this context, there is provided herein novel porous organometaloxide materials, for example in the form of nanoparticles, whose framework contain metal adjacent sites covalently bound via a responsively cleavable linker.

1) General Description of Porous Organometaloxide Materials of the Invention

In one aspect, there is provided a porous organometaloxide material comprising a porous three-dimensional framework of metal-oxygen bonds, wherein at least a subset of metal atoms in the material's framework are connected to at least another metal atom in the framework through a linker having one of the following structures:

$*R^1\text{-}L\text{-}R^2\text{—}*$,

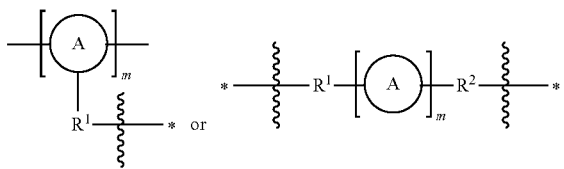

wherein:
each occurrence of * denotes a point of attachment to a metal atom in the material's framework;

A represents a monomer of a responsively cleavable fragment of biological/biodegradable polymer;

m is an integer from 2 to 10000 and m represents the number of monomers in the fragment of biological/biodegradable polymer;

L represents a responsively cleavable covalent bond; and $R^1$ and $R^2$ independently represent an optionally substituted C1-20 alkylenyl moiety, an optionally substituted C1-20 heteroalkylenyl moiety, an optionally substituted ethylenyl moiety, —C≡C— or an optionally substituted phenyl moiety, wherein the C1-20 alkylenyl, C1-20 heteroalkylenyl or ethylenyl moiety may bear one or more substituents selected from halogen or —OR where R may represent H or C1-6 alkyl, and the phenyl moiety may bear one or more substituents independently selected from halogen, C1-6 alkyl, —NO$_2$, —CN, isocyano, —OR$^p$, —N(R$^p$)$_2$ wherein each occurrence of R$^p$ independently represents H or C1-6 alkyl.

Advantageously, when the linker has the structure $*\text{—}R^1\text{-}L\text{-}R^2\text{—}*$, the subset of metal atoms in the material's framework that are connected to the linker $*\text{—}R^1\text{-}L\text{-}R^2\text{—}*$, represent at least 30% of the metal atoms present in the porous organometaloxide material of the invention.

In the present document, the porous organometaloxide material will be said to be "at least 30% doped". As used herein, "x" in the expression "x % doped" is calculated based on the % of metal centers in the porous organometaloxide material that comes from the starting material $(X)_3M_1\text{-}R^1\text{-}L\text{-}R^2\text{-}M_2(X)_3$ used to synthesize the organometaloxide material according to the invention. This % doping also reflects the contents of responsively cleavable covalent bond L in the organometaloxide material. The higher the % doping, the higher the content of linker L in the porous organometaloxide, and the greater the ability of the resulting organometaloxide material to undergo complete structural breakdown, suitable for the intended applications.

Likewise, when the linker has the structure

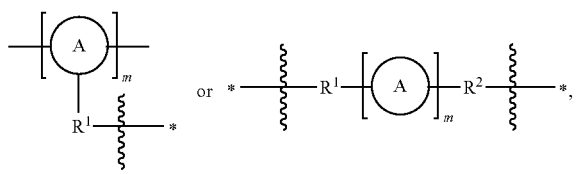

as used herein, "x" in the expression "x % doped" is calculated based on the % of metal centers in the porous organometaloxide material that comes from the starting material

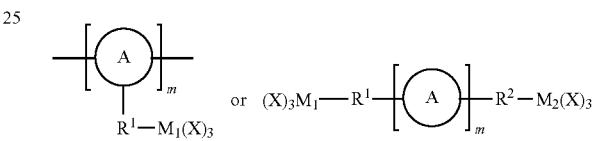

used to synthesize the organometaloxide material according to the invention. This % doping also reflects the contents of responsively cleavable fragment of biological/biodegradable polymer

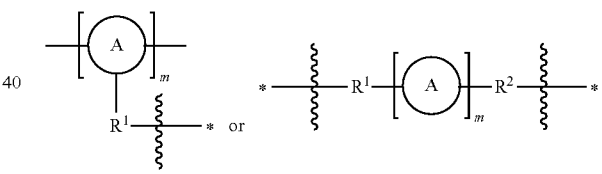

in the organometaloxide material. The higher the % doping, the higher the content of linker

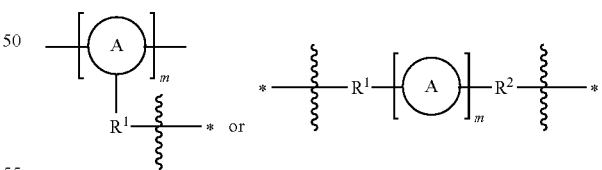

in the porous organometaloxide, and the greater the ability of the resulting organometaloxide material to undergo complete structural breakdown, suitable for the intended applications.

Advantageously, when the linker has the structure $*\text{—}R^1\text{-}L\text{-}R^2\text{—}*$, the subset of metal atoms in the material's framework that are connected to the linker $*\text{—}R^1\text{-}L\text{-}R^2\text{—}*$, may range anywhere from 30% to 100% of the metal atoms present in the porous organometaloxide material of the invention. For example, the subset of metal atoms in the material's framework that are connected to the linker $*\text{—}R^1\text{-}$ L-R²—*, may range from 30% to 100%, from 30% to 90%, from 30% to 80%, from 30% to 70%, from 30% to 60%; from 30% to 50%, from 30% to 40%, of the metal atoms present in the porous organometaloxide material of the invention. The final % doping of the porous organometaloxide material will depend on the respective molar ratios of starting materials $(X)_3M_1-R^1-L-R^2-M_2(X)_3$ and $M(X^A)_4$ used in the synthesis of the material (cf. section dealing with synthetic process, later in the present document). When no $M(X^A)_4$ is used in the preparation of the material, a doping of 100% will be reached (i.e., only $(X)_3M_1-R^1-L-R^2-M_2(X)_3$ is used as metal source).

Advantageously, for a slower and more controlled desintagrability/degradability of the porous organometaloxide material, the subset of metal atoms in the material's framework that are connected to the linker *—R¹-L-R²—*, may be in the lower % range; for example from 30% to 35%, from 30% to 40%, from 30% to 45%, from 30% to 50%, of the metal atoms present in the porous organometaloxide material of the invention. Advantageously, the subset of metal atoms in the material's framework that are connected to the linker *—R¹-L-R²—*, may range from 30% to 40%, preferably about 30%.

Advantageously, for a faster desintagrability/degradability of the porous organometaloxide material, the subset of metal atoms in the material's framework that are connected to the linker *—R¹-L-R²—*, may be in the higher % range; for example from 55% to 60%, from 55% to 65%, from 55% to 70%, from 55% to 75%, from 55% to 80%, from 55% to 85%, from 55% to 90%, from 55% to 95%, from 55% to 100%, of the metal atoms present in the porous organometaloxide material of the invention.

Advantageously, when the linker has the structure

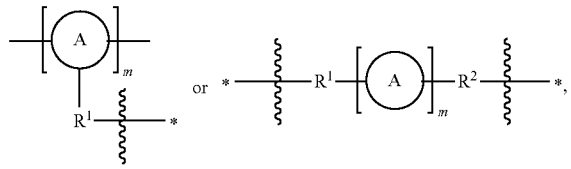

the subset of metal atoms in the material's framework that are connected to said linker may represent 100% of the metal atoms present in the porous organometaloxide material of the invention. In other words, in that case, all the metal atoms in the porous organometaloxide material of the invention originate from the starting materials

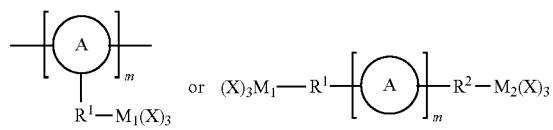

used to prepare the organometaloxide material.
However, this is not a requirement, and the contents of linker

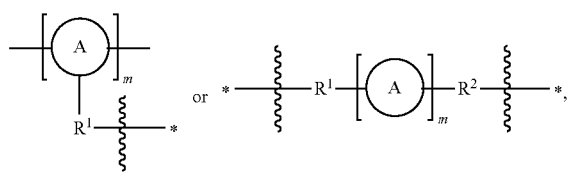

in the material's framework may be modulated in the same as described for the linker *—R¹-L-R²—*, above.

Thus, advantageously, when the linker has the structure

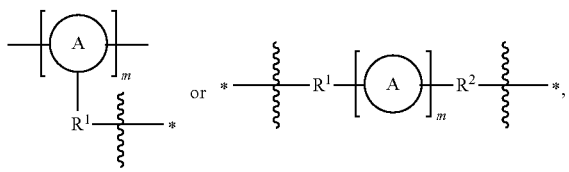

the subset of metal atoms in the material's framework that are connected to the linker

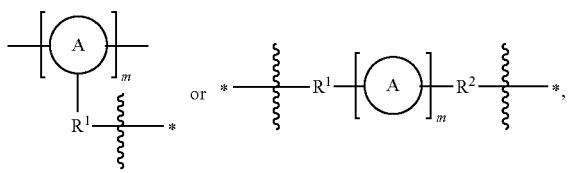

respectively, may range anywhere from 5% to 100% of the metal atoms present in the porous organometaloxide material of the invention. For example, the subset of metal atoms in the material's framework that are connected to the linker

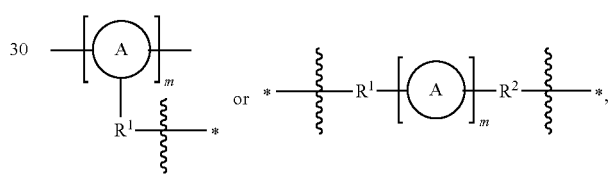

respectively, may range from 5% to 100%, from 5% to 90%, from 5% to 80%, from 5% to 70%, from 5% to 60%; from 5% to 50%, from 5% to 40%, from 5% to 30%, from 5% to 20%, from 5% to 10%, of the metal atoms present in the porous organometaloxide material of the invention. Advantageously, the subset of metal atoms in the material's framework that are connected to the linker

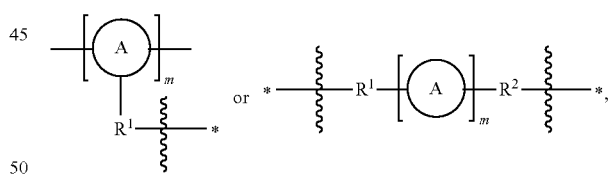

respectively, may range from 10% to 100%, from 10% to 90%, from 10% to 80%, from 10% to 70%, from 10% to 60%; from 10% to 50%, from 10% to 40%, from 10% to 30%, from 10% to 20%, of the metal atoms present in the porous organometaloxide material of the invention. Advantageously, the subset of metal atoms in the material's framework that are connected to the linker

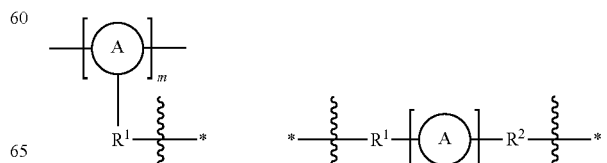

respectively, may range from 20% to 100%, from 20% to 90%, from 20% to 80%, from 20% to 70%, from 20% to 60%; from 20% to 50%, from 20% to 40%, from 20% to 30%, of the metal atoms present in the porous organometaloxide material of the invention. Advantageously, the subset of metal atoms in the material's framework that are connected to the linker

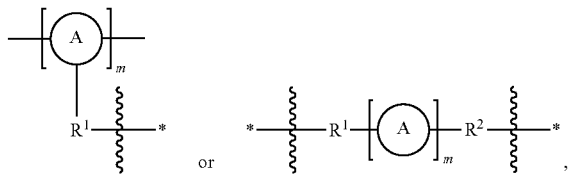

respectively, may range from 30% to 100%, from 30% to 90%, from 30% to 80%, from 30% to 70%, from 30% to 60%; from 30% to 50%, from 30% to 40%, of the metal atoms present in the porous organometaloxide material of the invention. The final % doping of the porous organometaloxide material will depend on the respective molar ratios of starting materials

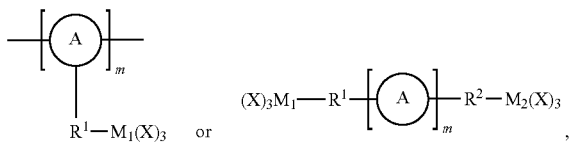

respectively and $M(X^4)_4$ used in the synthesis of the material (cf. section dealing with synthetic process, later in the present document). When no $M(X^4)_4$ is used in the preparation of the material, a doping of 100% will be reached (i.e., only

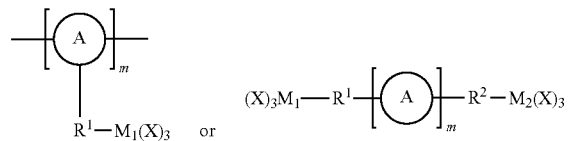

is used as metal source).

Advantageously, for a slower and more controlled desintagrability/degradability of the porous organometaloxide material, the subset of metal atoms in the material's framework that are connected to the linker

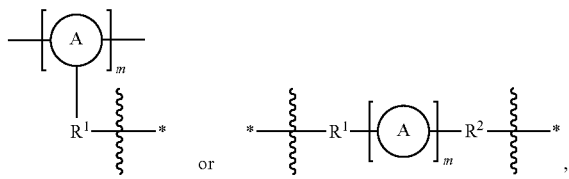

respectively, may be in the lower % range; for example from 5% to 10%, from 5% to 15%, from 5% to 20%, from 5% to 25%, from 5% to 30%, from 5% to 35%, from 5% to 35%, from 5% to 40%, from 5% to 45%, from 5% to 50%, of the metal atoms present in the porous organometaloxide material of the invention. Advantageously, the subset of metal atoms in the material's framework that are connected to the linker

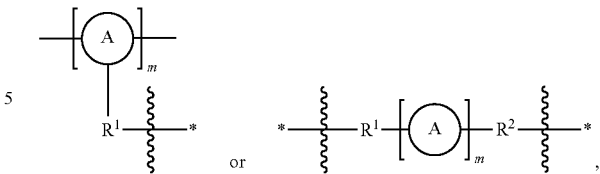

respectively, may range from 30% to 35%, from 30% to 35%, from 30% to 40%, from 30% to 45%, from 30% to 50%; preferably from 30% to 40%, preferably about 30%.

Advantageously, for a faster desintagrability/degradability of the porous organometaloxide material, the subset of metal atoms in the material's framework that are connected to the linker

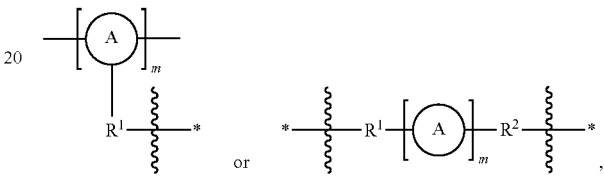

respectively, may be in the higher % range; for example from 55% to 60%, from 55% to 65%, from 55% to 70%, from 55% to 75%, from 55% to 80%, from 55% to 85%, from 55% to 90%, from 55% to 95%, from 55% to 100%, of the metal atoms present in the porous organometaloxide material of the invention. Advantageously, the subset of metal atoms in the material's framework that are connected to the linker

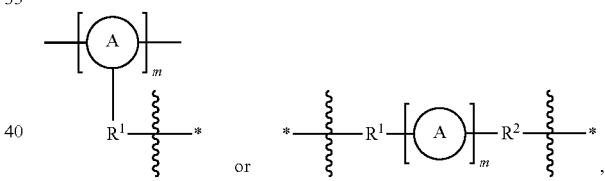

respectively, may be 100%.

In all cases, the high content of linker *—$R^1$-L-$R^2$—*,

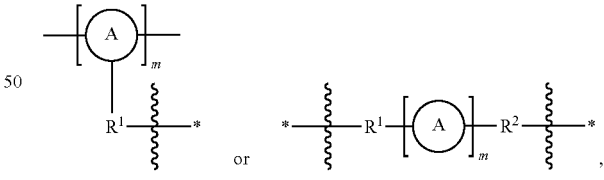

in the porous organometaloxide material confers the resulting material the ability to undergo complete structural breakdown. As such, the resulting porous organometaloxide material exhibits enhanced biodegradability compared to other related materials known in the art upon application of a suitable stimulus, thereby resulting in smaller, more easily hydrolysable, and consequently less harmful fragments.

Advantageously, the fragment of biological/biodegradable polymer may be an oligomer (i.e., m may range from 2 to 20), a medium sized fragment (i.e., m may range from 20 to 1000), or a large fragment (i.e., m may reach several thousands, for example it may range from 1000 to 10000).

Advantageously, in the linker *—R$^1$-L-R$^2$—*

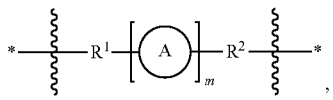

each occurrence of R$^1$ and R$^2$ may be identical.

Advantageously, in the linker

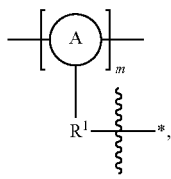

each occurrence of R$^1$ may be identical.

Advantageously, in the linker *—R$^1$-L-R$^2$—*, R$^1$ and R$^2$ may be any organic radical from any commercially available silylated derivative suitable for sol-gel chemistry. For example, R$^1$ and R$^2$ may independently represent —CH$_2$—, —(CH$_2$)$_2$—, —(CH$_2$)$_3$—, —(CH$_2$)$_4$—, or phenyl.

Advantageously, R$^1$ and R$^2$ may be identical and may each represent —CH$_2$—, —(CH$_2$)$_2$—, —(CH$_2$)$_3$—, —(CH$_2$)$_4$—, or phenyl.

Advantageously, the metal is selected from Si—, Ti— or Zr, or mixture thereof, and the porous organometaloxide material according to the invention is a Si-, Ti- and/or Zr-based porous organometaloxide material. The expression "and/or" in this context means that the porous organometaloxide material may: contain Si only as metal, contain Ti only as metal, contain Zr only as metal, or be a mixed-metal organometaloxide material containing any combination of at least two of Si, Ti or Zr as metal(s) in the framework.

Advantageously, the porous organometaloxide material according to the invention may:

contain 90.0-100% Si as metal (% based on the number of available metal sites in the framework), the remaining metal sites may be Ti or Zr;

contain 90.0-100% Ti as metal (% based on the number of available metal sites in the framework), the remaining metal sites may be Ti or Zr; or contain 90.0-100% Zr as metal (% based on the number of available metal sites in the framework), the remaining metal sites may be Ti or Zr.

Advantageously, the porous organometaloxide material according to the invention may be a Si—Ti mixed-metal organometaloxide material containing 0.1-50.0% Si and 0.1-50.0% Ti, the % sum of Si and Ti adding to 100% the number of available metal sites in the framework. For example, the porous organometaloxide material according to the invention may be a Si-based porous organometaloxide material doped with 0.1 to 10.0% Ti (% based on the number of available metal sites in the framework).

Advantageously, the porous organometaloxide material according to the invention may be a mixed metal, M-based porous organometaloxide material, where M may be Si or Ti, containing at least 80.0%, preferably at least 85.0%, preferably at least 90.0%, preferably at least 95.0%, preferably at least 95.5%, preferably at least 99.9% Si or Ti (% based on the number of available metal sites in the framework), the remaining metal sites being Si, Ti and/or Zr.

Advantageously, the substituent(s) on R$^1$ and R$^2$ may be suitably selected to facilitate the cleavage of the responsively cleavable linker L when the external signal/stimulus is applied (e.g., a change in pH (either an increase or decrease), a change in redox potential, the presence of UV light or near infrared light, an enzymatic cleavage, a change in temperature, etc.). For example, the substituent(s) on R$^1$ and R$^2$ may be selected based on their electron-withdrawing or -donating properties, to facilitate the cleavage of the linker moiety. For example, for illustrative purposes, when L may be an imine bond and R$_1$ and/or R$_2$ may be a phenyl group, the phenyl group may bear a nitro group to make the imine bond more reactive (i.e., more responsive to cleavage upon application of a suitable stimulus).

One advantageous aspect of this invention resides in the simple, yet compelling, underlying concept: namely a precursor having one of the following structures:

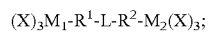

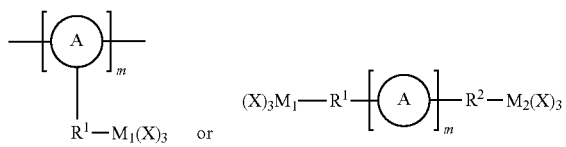

wherein A, L, R$^1$, R$^2$ and m are as defined above, and M$_1$ and M$_2$ independently represent Si, Ti or Zr, is chemically inserted within the framework of the porous organometaloxide material via sol-gel chemistry. Advantageously, said precursor (X)$_3$M$_1$-R$^1$-L-R$^2$-M$_2$(X)$_3$ is introduced in the porous organometaloxide material framework so that the subset of metal atoms in the material's framework that are connected to the linker *—R$^1$-L-R$^2$—*, represent at least 30% of the metal atoms present in the porous organometaloxide material of the invention. In other words, at least 30% of the metal centers in the porous organometaloxide material framework originates from the precursor (X)$_3$M$_1$-R$^1$-L-R$^2$-M$_2$(X)$_3$ (i.e., M$_1$ and M$_2$ account for at least 30% of the metal center in the organometaloxide material).

Advantageously, said precursor

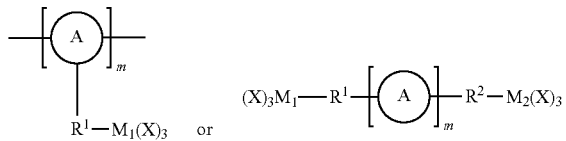

is introduced in the porous organometaloxide material framework so that the subset of metal atoms in the material's framework that are connected to the linker

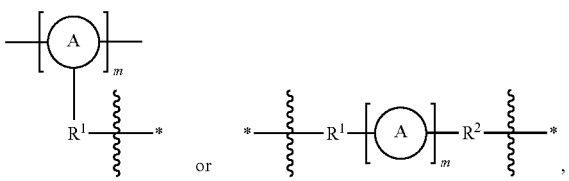

respectively represent at least 5% of the metal atoms present in the porous organometaloxide material of the invention. In other words, at least 5% of the metal centers in the porous organometaloxide material framework originates from the precursor

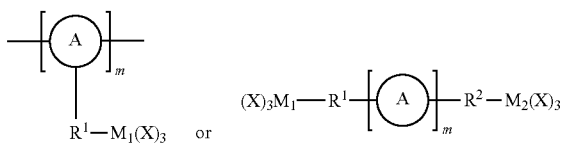

(i.e., $M_1$ and $M_2$ account for at least 5% of the metal center in the organometaloxide material).

In the above, X may represent a hydrolysable or nonhydrolyzable group, provided that on each occurrence of $M_1$ and $M_2$, at least one occurrence of X represents a hydrolysable group.

When X represents a hydrolysable group, it may be selected from a C1-6 alkoxy, C1-6 acyloxy, halogen or amino moiety. Advantageously, when X represents a hydrolysable group, X may represent Cl, —OMe, —OEt, —OiPr or —OtBu.

When X represents a nonhydrolyzable group, it may be selected from an optionally substituted C1-20 alkyl, C2-20 alkenyl or C2-20 alkynyl moiety, an optionally substituted C1-20 heteroalkyl, C2-20 heteroalkynyl or C2-20 heteroalkynyl moiety, or an optionally substituted phenyl moiety, wherein the substituents on the phenyl, alkyl, alkenyl, alkynyl, heteroalkyl, heteroalkenyl and heteroalkynyl moieties may be independently selected from halogen, —NO$_2$, —CN, isocyano, C1-6 alkoxy, an oxirane/epoxyde moiety, —N(R)$_2$ wherein each occurrence of R is independently selected from H or C1-6 alkyl.

Advantageously, when X represents a nonhydrolyzable group, X may represent C1-6 alkyl or C2-6 alkenyl; preferably -Me, -Et or —CH=CH$_2$; most preferably -Me or -Et.

The insertion of the responsively cleavable linker within the framework of the porous metaloxide is performed during the synthesis of the porous organometaloxide material itself, no additional step is required, if not the preparation of the required $(X)_3M_1$-$R^1$-L-$R^2$-$M_2(X)_3$;

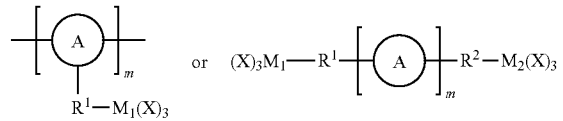

precursor, which may also be carried out in situ. It is then important to choose the correct $(X)_3M_1$-$R^1$-L-$R^2$-$M_2(X)_3$;

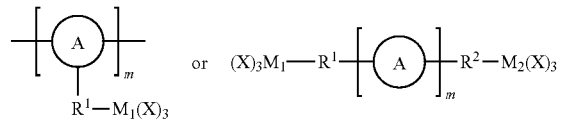

precursor in order to obtain the desired self-destructive behavior in the final operational environment.

In the case of organometaloxide material containing the linker *—$R^1$-L-$R^2$—*, the ratio $(X)_3M_1$-$R^1$-L-$R^2$-$M_2(X)_3$/$M(X^A)_4$ precursor used for the synthesis is also important, as it determines the % doping (and thus the ratio of responsively cleavable linker L within the material), and therefore the ability of the porous organometaloxide material to disintegrate upon application of a suitable stimulus. Advantageously, in the case of organometaloxide material containing the linker *—$R^1$-L-$R^2$—*, a minimum of 30% of the whole metallic atoms present in the organometaloxide material should come from the $(X)_3M_1$-$R^1$-L-$R^2$-$M_2(X)_3$ linker. Because $(X)_3M_1$-$R^1$-L-$R^2$-$M_2(X)_3$ is bivalent (i.e., because this precursor contains two metal atoms per cleavable bond L), M1 and M2 represent 30% of the metal centers in the resulting organometaloxide material (i.e., 30% doping). This corresponds to 15% molar ratio if the responsively cleavable moiety of the linker is taken in account (L), as for each $M_1$ and $M_2$ set only one L is associated. For a doping of 100%, $(X)_3M_1$-$R^1$-L-$R^2$-$M_2(X)_3$ may be used as the exclusive source of metal (i.e., no $M(X^A)_4$ is used).

The following Table 1A describes exemplary ratios of equivalents $(X)_3M_1$-$R^1$-L-$R^2$-$M_2(X)_3$/$M(X^A)_4$ to reach the desired % doping (which is at least 30%):

TABLE 1A

| $M(X^A)_4$ | $(X)_3M_1$-$R^1$-$R^2$-$M_2(X)_3$ | $(X)_3M_1$-$R^1$-L-$R^2$-$M_2(X)_3$ | % doping |
|---|---|---|---|
| 0.70 eq. | 0.30 eq. ǂ | 0.15 eq. # | 30% |
| 0.60 eq. | 0.40 eq. ǂ | 0.20 eq. # | 40% |
| 0.50 eq. | 0.50 eq. ǂ | 0.25 eq. # | 50% |
| 0.40 eq. | 0.60 eq. ǂ | 0.30 eq. # | 60% |
| 0.30 eq. | 0.70 eq. ǂ | 0.35 eq. # | 70% |
| 0.20 eq. | 0.80 eq. ǂ | 0.40 eq. # | 80% |
| 0.10 eq. | 0.90 eq. ǂ | 0.45 eq. # | 90% |
| — | 1 eq. ǂ | 0.5 eq. # | 100% |

ǂ equivalents expressed in terms of metal atoms ($M_1$ and $M_2$) introduced by the bivalent starting material $(X)_3M_1$-$R^1$-L-$R^2$-$M_2(X)_3$ in the final organometaloxide material.
equivalents expressed in terms of responsively cleavable bond L introduced by the bivalent starting material $(X)_3M_1$-$R^1$-L-$R^2$-$M_2(X)_3$ in the final organometaloxide material.

The reaction conditions may be modulated, depending on the eq. ratios $(X)_3M_1$-$R^1$-L-$R^2$-$M_2(X)_3$/$M(X^A)_4$ used. From the general knowledge in the field of organometaloxide chemistry, the practitioner will readily know how to adjust suitable reaction conditions, for example the type of solvent used to effect the reaction depending on the respective solubilities of the selected $(X)_3M_1$-$R^1$-L-$R^2$-$M_2(X)_3$ and $M(X^A)_4$.

Likewise for

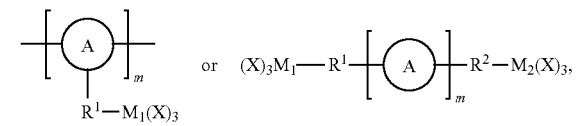

the following Tables 1B and Table 1C describes exemplary ratios of equivalents

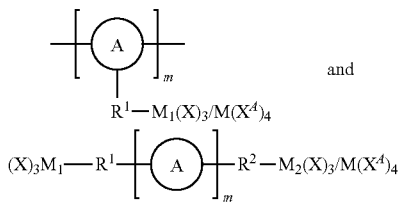

respectively, to reach the desired % doping (which is at least 5%):

TABLE 1B

| $M(X^A)_4$ | $R^1$—$M_1(X)_3$ | % doping |
|---|---|---|
| 0.90 eq. | 0.10 eq. ǂ | 10% |
| 0.80 eq. | 0.20 eq. ǂ | 20% |

TABLE 1B-continued

| | | |
|---|---|---|
| $M(X^4)_4$ | $R^1-M_1(X)_3$ [A]$_m$ structure | % doping |
| 0.70 eq. | 0.30 eq.‡ | 30% |
| 0.60 eq. | 0.40 eq.‡ | 40% |
| 0.50 eq. | 0.50 eq.‡ | 50% |
| 0.40 eq. | 0.60 eq.‡ | 60% |
| 0.30 eq. | 0.70 eq.‡ | 70% |
| 0.20 eq. | 0.80 eq.‡ | 80% |
| 0.10 eq. | 0.90 eq.‡ | 90% |
| — | 1 eq.‡ | 100% |

‡ equivalents expressed in terms of metal atoms ($M_1$) introduced by the starting material

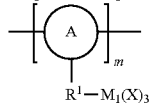

in the final organometaloxide material.

TABLE 1C

| | | |
|---|---|---|
| $M(X^4)_4$ | $(X)_3M_1-R^1-[A]_m-R^2-M_2(X)_3$ | % doping |
| 0.90 eq. | 0.10 eq.‡ | 10% |
| 0.80 eq. | 0.20 eq.‡ | 20% |
| 0.70 eq. | 0.30 eq.‡ | 30% |
| 0.60 eq. | 0.40 eq.‡ | 40% |
| 0.50 eq. | 0.50 eq.‡ | 50% |
| 0.40 eq. | 0.60 eq.‡ | 60% |
| 0.30 eq. | 0.70 eq.‡ | 70% |
| 0.20 eq. | 0.80 eq.‡ | 80% |
| 0.10 eq. | 0.90 eq.‡ | 90% |
| — | 1 eq.‡ | 100% |

‡ equivalents expressed in terms of metal atoms ($M_1$ and $M_2$) introduced by the bivalent starting material

in the final organometaloxide material.

Advantageously, the porous organometaloxide material may be a hybrid material. The hybrid organic/inorganic nature of the material is naturally conferred by the presence of the organic moiety *—$R^1$-L-$R^2$—*,

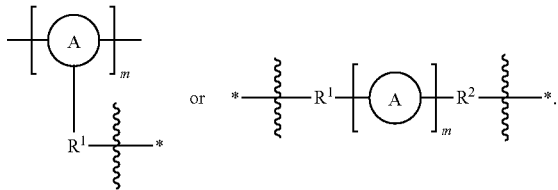

However, other organic moieties may be introduced in the porous organometaloxide material by conventional sol-gel chemistry methods known in the art. For example, the use of a $R^3$-M($R^4$)$_3$ precursor, wherein M is Si, Ti or Zr; $R^3$ is a nonhydrolyzable organic moiety bound to M via a carbon atom, and each occurrence of $R^4$ is independently a hydrolysable group. By "nonhydrolyzable organic moiety" is meant an organic moiety that is not cleaved from the metal M during the sol-gel process leading to the porous organometaloxide framework material. Conversely, by "hydrolyzable group" is meant a radical that is hydrolyzed (cleaved from the metal M) during the sol-gel process leading to the porous organometaloxide framework material. Typically, $R^4$ may be a C1-6 alkoxy, C1-6 acyloxy, halogen or amino group. $R^3$ may be an optionally substituted C1-20 alkyl, C2-20 alkenyl or C2-20 alkynyl moiety, an optionally substituted C1-20 heteroalkyl, C2-20 heteroalkynyl or C2-20 heteroalkynyl moiety, or an optionally substituted phenyl moiety. Advantageously, $R^3$ may bear a substituent that allows further functionalization of the organometaloxide material, or posses a functionality that imparts desired characteristics. For example, the substituents on the phenyl, alkyl, alkenyl, alkynyl, heteroalkyl, heteroalkenyl and heteroalkynyl moieties may be independently selected from halogen, —$NO_2$, —CN, isocyano, C1-6 alkoxy, an oxirane/epoxyde moiety, —$N(R)_2$ wherein each occurrence of R is independently selected from H or C1-6alkyl. Organic/inorganic hybrid Si-, Ti- and Zr-based porous organometaloxide framework materials are well-known in the literature, as well as methods for their preparation. (See for example, (a) for Si-based materials: [11]; (b) for Ti-based materials: [12]; (c) for Zr-based materials: [13]. These methods may be readily adapted to the present hybrid porous organometaloxide materials, by using a $(X)_3M_1$-$R^1$-L-$R^2$-$M_2(X)_3$ precursor as defined above and herein, in the sol-gel synthetic process.

The porous organometaloxide material according to the invention may be in any form known for conventional porous hybrid or purely inorganic Si-, Ti- or Zr-based metaloxide framework materials. For example, porous organometaloxide material according to the invention may be in the form of a monolith, a film (thin or thick film), powder, nanoparticles, or spherical, cubic, cylindrical or disc-like particles.

Advantageously, the porous organometaloxide material may be in the form of nanoparticles. For example, the porous material according to the invention may have a particle diameter from 1 to 1000 nanometers, preferably from 1 to 500 nm, preferably from 1 to 250 nm, preferably from 1 to 100 nm, from 1 to 50 nm preferably from 1 to 20 nm. Advantageously, the porous organometaloxide material may be in the form of nanoparticles ranging from 20-100 nm in particle diameter, for example about 20 nm, for example about 100 nm. The diameter particle may be modulated depending on reaction condition parameters, such as reaction time, temperature of reaction, base used (ammonium hydroxide, NaOH, . . . ), amount of organic solvent used (e.g., EtOH). The practitioner can adapt knowledge from general synthetic methods for mesoporous organometaloxide chemistry to fine tune the proper reaction conditions amenable to the desired particle diameter.

Advantageously, the porous organometaloxide material may be in the form of nanoparticles dispersed in a solvent. The solvent may be that used in the synthesis of the material.

Advantageously, the porous organometaloxide material may be in the form of a powder.

Advantageously, the porous organometaloxide material may be in the form of a film. For example, it may be in the form of a thin film.

Advantageously, the porous organometaloxide material may be mesoporous, microporous, macroporous or mixed mesoporous-macroporous; preferably mesoporous.

Advantageously, the porous disintegratable organometaloxide materials of the invention preferably have pores in the size range of from about 1 to about 1,000 nm, preferably from 1 to 500 nm, more preferably from 1 to 250 nm, even more preferably from 1 to 100 nm, most preferably from 1 to 50 nm. These pores may be well-ordered and of uniform size, but this is not a requirement of this invention. Naturally, when the porous organometaloxide material is in the form of nanoparticles, as described above, the pore size will be proportionally smaller than the particle size.

Advantageously, L may be any moiety that contains a responsively cleavable covalent bond, which can be cleaved upon exposure to a determined stimulus, or a responsively cleavable fragment of a biological compound (proteins, carbohydrates, etc.) or biodegradable synthetic polymer, able to undergo degradation (e.g., enzymatic) or a supramolecular assembly (non-covalent bond).

Advantageously, when the linker has the structure *—R$^1$-L-R$^2$—*, L may represent a responsively cleavable covalent bond selected from:

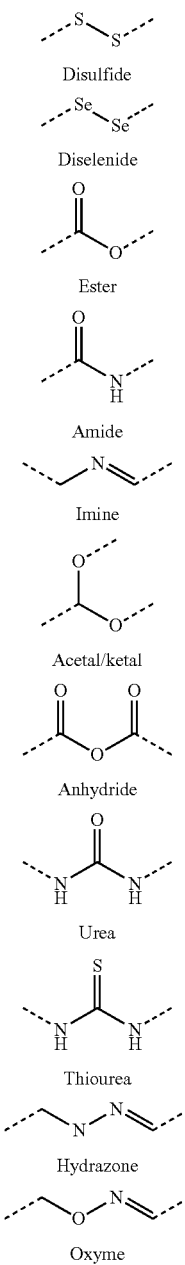

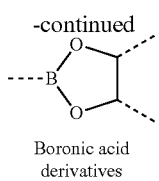

Boronic acid derivatives

Preferably, when the linker has the structure *—R$^1$-L-R$^2$—*, L may represent a responsively cleavable covalent bond selected from disulfide, imine, amide, ester, urea, or thiourea.

Advantageously, the linker may represent a responsively cleavable fragment of a biological/biodegradable polymer selected from polysaccharides, polypeptides (e.g., polylysine), polynucleotides (e.g., DNA or RNA fragment) and synthetic biodegradable polyethyleneglycol or polylactide polymers, and the linker has the structure

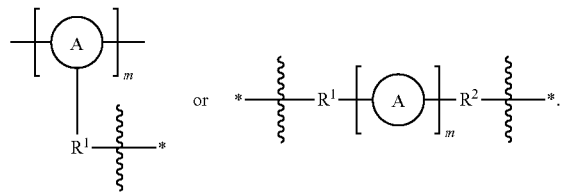

Advantageously, when the linker has the structure

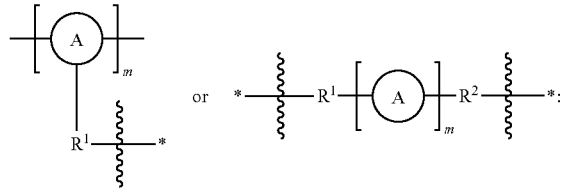

A may represent a carbohydrate monomer and the linker may be derived from a natural polysaccharide such as cellulose, amylose, dextran, etc. or a natural or synthetic oligosaccharide;

A may represent a peptide monomer (amino acid residue) and the linker may be derived from a naturally occurring protein or polypeptide (e.g., polylysine) or a synthetic polypeptide;

A may represent a polynucleotide and the linker may be derived from an RNA or DNA fragment.

It is understood that the linker having the structure

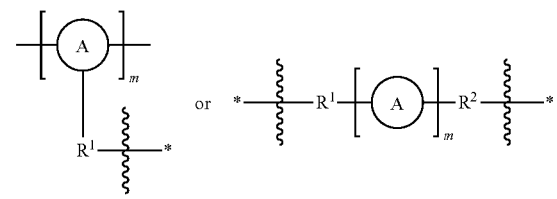

may be a homopolymer fragment (i.e., each occurrence of A is identical), or a copolymer fragment (i.e., not all occurrences of A are identical). In addition,

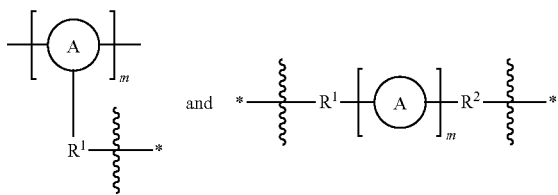

may represent a fragment of a block copolymer (i.e., m1 adjacent occurrences of monomer A1, followed by m2 adjacent occurrences of monomer A2, etc.), or a polymer fragment where the different monomers are randomly distributed.

The linker

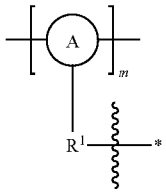

may be obtained by reaction of a reactive functional group present on the monomers A of a precursor polymer fragment

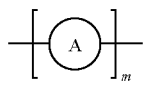

(for example, a hydroxyl, amino group, etc.) with an organosilane moiety $X^B$—$R^1M^1(X)_3$, wherein A, m, $M^1$, $R^1$ and X are as defined above, and $X^B$ represents a nonhydrolyzable group bearing a suitable functional group capable of forming a covalent bond with said reactive functional group present on A. Not all occurrences of A may end up being functionalized with, depending on the molar ratio $X^B$—$R^1M^1(X)_3$:m. For example, when $X^B$—$R^1M^1(X)_3$:m<1 (less than equimolar ratio), the monomers A may be randomly functionalized, the distribution of functionalized monomers A being controlled in part by the steric hindrance of $X^B$—$R^1M^1(X)_3$, and the identity (type) of A when

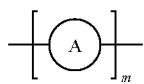

is made up of more than one type of monomer.

When the monomers A are not all identical on the linker

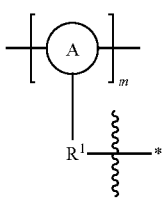

for example, it contains two types of monomers, $A_1$ and $A_2$, it is possible to selectively functionalized one type of monomer over the other by suitably selecting the reactive functional group on $X^B$ (for example, $A_1$ may be selectively functionalized over $A_2$). For example, $X^B$ may represent an optionally substituted C1-20 alkyl, C2-20 alkenyl or C2-20 alkynyl moiety, an optionally substituted C1-20 heteroalkyl, C2-20 heteroalkynyl or C2-20 heteroalkynyl moiety, or an optionally substituted phenyl moiety, wherein the phenyl, alkyl, alkenyl, alkynyl, heteroalkyl, heteroalkenyl and heteroalkynyl moieties may be independently bear at least one functional group capable of covalently reacting with a reactive functional group present on the monomers A of a precursor polymer fragment

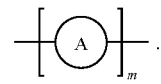

As non limiting examples:

when A represents a carbohydrate monomer: $X^B$ may bear a reactive functional such as halogen, —$CO_2R$, isocyano, or an oxirane/epoxyde moiety, wherein R is selected from H or C1-6 alkyl, which can react with an —OH group present on A. For example, $X^B$ may represent —$(CH_2)_{1-6}R^X$ preferably —$(CH_2)_3R^X$, wherein $R^X$ represents halogen, —NCO, or

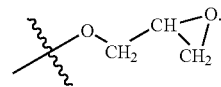

when A represents a peptide monomer (amino acid residue): $X^B$ may bear a reactive functional such as halogen, —$CO_2H$, isocyano, or an oxirane/epoxyde moiety, which can react with an —OH or —$NH_2$ group present on A. For example, $X^B$ may represent —$(CH_2)_{1-6}R^X$, preferably —$(CH_2)_3R^X$, wherein $R^X$ represents halogen, —NCO, or

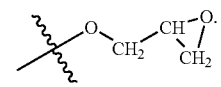

when A represents a nucleotide monomer (nucleotide base): $X^B$ may bear a reactive functional such as halogen, —$CO_2H$, isocyano, or an oxirane/epoxyde moiety, which can react with an —OH or —$NH_2$ group present on A. For example, $X^B$ may represent —$(CH_2)_{1-6}R^X$, preferably —$(CH_2)_3R^X$, wherein $R^X$ represents halogen, —NCO, or

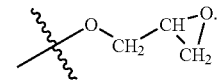

Likewise, the linker having the structure

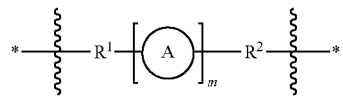

may be obtained by reaction of reactive functional groups present at each extremity of a polymer precursor

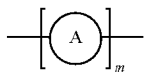

(for example, a hydroxyl, amino group, etc.) with an organosilane moiety $X^B$—$R^1M^1(X)_3$, wherein A, m, $M^1$, $R^1$ and X are as defined above, and $X^B$ represents a nonhydrolyzable group bearing a suitable functional group capable of forming a covalent bond with said reactive functional group present on each extremity of

As non limiting examples:
when

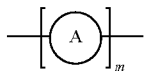

represents a PEG fragment: $X^B$ may bear a reactive functional such as halogen, —$CO_2R$, isocyano, or an oxirane/epoxyde moiety, wherein R is selected from H or C1-6 alkyl, which can react with the terminal PEG —OH groups. For example, $X^B$ may represent —$(CH_2)_{1-6}R^X$, preferably —$(CH_2)_3R^X$, wherein $R^X$ represents halogen, —NCO, or

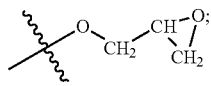

when

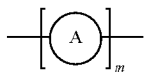

represents a polylactide fragment: $X^B$ may bear a reactive functional such as halogen, —$NH_2$, —$CO_2R$, isocyano, or an oxirane/epoxyde moiety, wherein R is selected from H or C1-6 alkyl, which can react with the terminal —OH and —COOH groups of the polylactide fragment.

Advantageously, the cleavage/degradation of the linker *—$R^1$-L-$R^2$*,

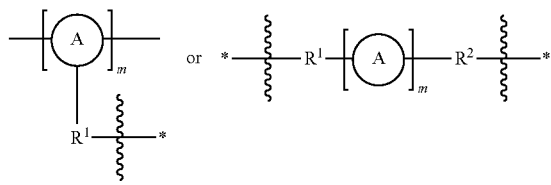

may be triggered by any suitable means. For example, it may be a change in pH (either an increase or a decrease), a change in redox potential, application of UV, visible or near infrared light, ultrasounds, electromagnetic radiation, a change in temperature, enzymatic cleavage, DNA binding, etc. . . . . The following Table 2 gives examples of cleavage/degradation triggering means for each of the aforementioned types of responsively cleavable linkers:

TABLE 2

| L | Exemplary Triggers |
|---|---|
| Disulfide | Reducing agents (e.g., NaBH$_4$, dithiothreitol (DTT), glutathione) |
| Diselenide | Reducing agents (e.g. thiols, metal complexes) |
| Ester | pH, enzymatic cleavage (e.g. esterase) [14] |
| Amide | Enzymatic cleavage (e.g. amidase) [15] |
| Imine | pH |
| Acetal/ketal | pH |
| Anhydride | pH |
| Urea/thiourea | Enzymatic cleavage (e.g. urease) [16] |
| Hydrazone | pH |
| Oxyme | pH |
| Boronic acid (complexed with diols) | pH, sugars |
| Boronic esters | pH, reducing agents (e.g., LiAlH$_4$) |
| Carbohydrate | pH, enzymatic cleavage (e.g. glycosidases) [17] |
| Peptide (e.g., polylysine) | Enzymatic cleavage (e.g. protease) [18] |
| Polyethyleneglycol (PEG) | Enzymatic cleavage (e.g. dehydrogenase) [19] |
| Polylactide | Enzymatic cleavage (e.g. esterase) [20] |
| Polynucleotide (e.g., RNA or DNA) | Enzymatic cleavage (e.g. nuclease, glycosidase) [21] |

Advantageously, the porous organometaloxide material according to the invention may comprise in its pores or at its surface at least one compound depending on the intended use of the porous organometaloxide material.

Advantageously, the compound may be a marker and/or cosmetically or pharmaceutically active principle. Advantageously, the marker may be selected from a contrast agent, a tracer, a radioactive marker, a fluorescent marker, a phosphorescent marker, a magnetic resonance imaging agent or a positron emission tomography agent, such as pyrene, rhodamine, IR783, Gd-EDTA or $^{64}$Cu-EDTA.

Advantageously, the marker may be any commercial dye. For example it may be a fluorescent molecule selected from rhodamines, fluorescein, luciferase, pyrene-containing markers, aminopyrrolidino-7-nitrobenzofurazan, or indocyanine green (ICG) for NIR emission.

2) Synthetic Overview:

In yet another aspect, there is provided a method for producing a new class of nanocomposite materials so called disintegratable hybrid porous organometaloxides, disintegratable hybrid microporous and macroporous organometaloxides, or disintegratable hybrid mesoporous-macroporous metaloxides (collectively, "DHMOs"). This new class of materials includes porous organometaloxide framework systems in whose framework a precursor having one of the following structures:

$(X)_3M_1$-$R^1$-L-$R^2$-$M_2(X)_3$;

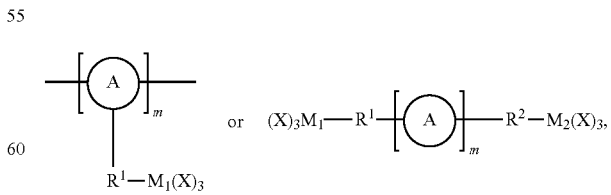

wherein A, L, $R^1$, $R^2$ and m are as defined above, and $M_1$ and $M_2$ independently represent Si, Ti or Zr, has been chemically inserted via conventional sol-gel chemistry. The unusual combination of inorganic and organic chemical structure with this scale of porosity and surfaces, together with the enhanced degradability, suggest a myriad of uses for DHMOs, such as but not limited to the controlled release and uptake of chemicals and drugs, ink, their use for sensing, diagnostics, bioassays, cosmetics, catalysis, and any use of porous Si-, Ti- and/or Zr-based organometaloxide materials known in the art.

Thus, in one aspect, there is provided a method of synthesizing disintegratable hybrid mesoporous organometaloxide materials (DHMOs) by covalently introducing a preselected precursor (general structure

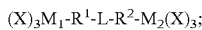

$(X)_3M_1\text{-}R^1\text{-}L\text{-}R^2\text{-}M_2(X)_3;$

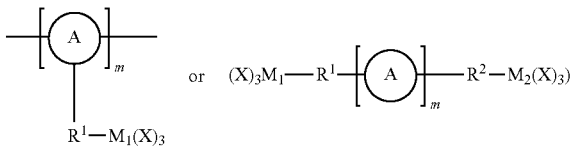

with a responsively cleavable linker, as defined herein, in the framework of the porous material itself. As such, the resulting DHMOs have a porous framework and present controlled self-destructive behavior in the environment where it is intended to perform its activity. The controlled self-destructive behavior is a property that provides numerous avenues of important applications for such porous systems, ranging from medical to cosmetics to catalysis and purification.

The practitioner has a well-established literature of porous organometaloxide materials chemistry to draw upon, in combination with the information contained herein, for guidance on synthetic strategies, protecting groups, and other materials and methods useful for the synthesis of the disintegratable materials of this invention.

General Synthetic Methods

Advantageously, the method (method 1) may comprise steps of:

a) Producing a supramolecular template by mixing a suitable surfactant and an aqueous solvent;

b) Adding a mixture of a precursor $M(X^A)_4$ and a selected precursor having the structure: $(X)_3M_1\text{-}R^1\text{-}L\text{-}R^2\text{-}M_2(X)_3;$

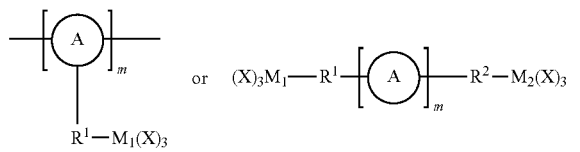

in an aqueous solvent under alkaline conditions; thereby coating the supramolecular template with an organometaloxide sol-gel mixture obtained by hydrolysis-condensation of metal alkoxide; and c) Removing the supramolecular template; thereby producing a porous organometaloxide material comprising a porous three-dimensional framework of metal-oxygen bonds, wherein at least a subset of metal atoms in the material's framework are connected to at least another metal atom in the framework through a linker having one of the following structures:

*—$R^1$-L-$R^2$—*,

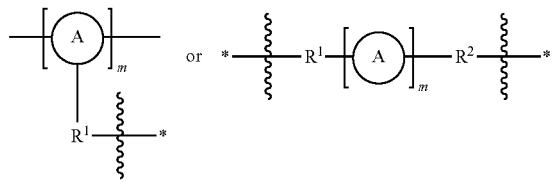

wherein:
each occurrence of * denotes a point of attachment to a metal atom in the material's framework;
A represents a monomer of a responsively cleavable fragment of biological/biodegradable polymer;
m is an integer from 2 to 10000 and m represents the number of monomers in the fragment of biological/biodegradable polymer;
M and each occurrence of $M_1$ and $M_2$ independently represents a metal selected from Si, Ti and Zr;
each occurrence of X and $X^A$ independently represents a hydrolysable or nonhydrolyzable group, provided that on each occurrence of $M_1$ and $M_2$, at least one occurrence of X represents a hydrolysable group and at least two occurrences of $X^A$ in the precursor $M(X^A)_4$ independently represent a hydrolysable group; wherein (i) when X or $X^A$ represents a nonhydrolysable group, it may be selected from an optionally substituted C1-20 alkyl, C2-20 alkenyl or C2-20 alkynyl moiety, an optionally substituted C1-20 heteroalkyl, C2-20 heteroalkenyl or C2-20 heteroalkynyl moiety, or an optionally substituted phenyl moiety, wherein the substituents on the phenyl, alkyl, alkenyl, alkynyl, heteroalkyl, heteroalkenyl and heteroalkynyl moieties may be independently selected from halogen, —$NO_2$, —CN, isocyano, C1-6 alkoxy, an oxirane/epoxyde moiety, —$N(R)_2$ wherein each occurrence of R is independently selected from H or C1-6 alkyl; and (ii) when X or $X^A$ represents a hydrolysable group, it may be selected from a C1-6 alkoxy, C1-6 acyloxy, halogen or amino moiety;
L represents a responsively cleavable covalent bond; and
$R^1$ and $R^2$ independently represent an optionally substituted C1-20alkylenyl moiety, an optionally substituted C1-20heteroalkylenyl moiety, an optionally substituted ethylenyl moiety, —C≡C— or an optionally substituted phenyl moiety, wherein the C1-20alkylenyl, C1-20heteroalkylenyl or ethylenyl moiety may bear one or more substituents selected from halogen or —OR where R may represent H or C1-6alkyl, and the phenyl moiety may bear one or more substituents independently selected from halogen, C1-6alkyl, —$NO_2$, —CN, isocyano, —$OR^p$, —$N(R^p)_2$ wherein each occurrence of $R^p$ independently represents H or C1-6alkyl.

Advantageously, a minimum of 30% molar ratio (based on the metal centers) of $(X)_3M_1\text{-}R^1\text{-}L\text{-}R^2\text{-}M_2(X)_3$ to 70% of $M(X^A)_4$ precursor may be used. Because $(X)_3M_1\text{-}R^1\text{-}L\text{-}R^2\text{-}M_2(X)_3$ is bivalent (i.e., because this precursor contains two metal atoms per cleavable bond L), the ratio 0.15 eq $(X)_3M_1\text{-}R^1\text{-}L\text{-}R^2\text{-}M_2(X)_3$/0.70 eq $M(X^A)_4$ means that $M_1$ and $M_2$ will represent 30% of the metal centers in the resulting organometaloxide material (i.e., 30% doping). For a doping of 100%, $(X)_3M_1\text{-}R^1\text{-}L\text{-}R^2\text{-}M_2(X)_3$ may be used as the only source of metal (i.e., no $M(X^A)_4$ is used). For exemplary ratios of equivalents $(X)_3M_1$-$R^1$-L-$R^2$-$M_2(X)_3$/$M(X^A)_4$ to reach a variety of % doping≥30%, see Table 1A.

Advantageously, a minimum of 5% molar ratio (based on the metal centers) of

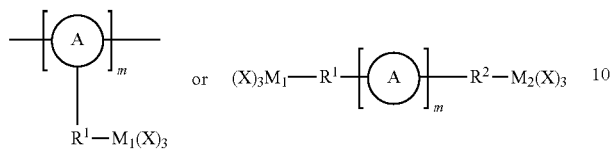

is to 95% of $M(X^A)_4$ precursor may be used. See Tables 1B and 1C.

Advantageously, for 100% doped porous organometaloxide materials, the method (method 2) may comprise steps of:
a) Producing a supramolecular template by mixing a suitable surfactant and an aqueous solvent;
b) Adding a selected precursor having the structure:

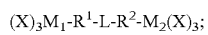

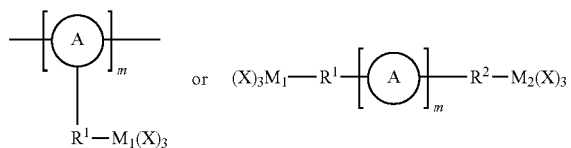

in an aqueous solvent under alkaline conditions; thereby coating the supramolecular template with an organometaloxide sol-gel mixture obtained by hydrolysis-condensation of metal alkoxide; and
c) Removing the supramolecular template; thereby producing a porous organometaloxide material comprising a porous three-dimensional framework of metal-oxygen bonds, wherein at least a subset of metal atoms in the material's framework are connected to at least another metal atom in the framework through a linker having one of the following structures:

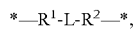

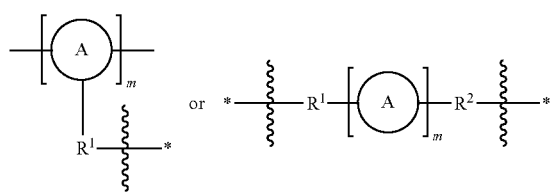

wherein:
each occurrence of * denotes a point of attachment to a metal atom in the material's framework;
A represents a monomer of a responsively cleavable fragment of biological/biodegradable polymer;
m is an integer from 2 to 10000 and m represents the number of monomers in the fragment of biological/biodegradable polymer;
each occurrence of $M_1$ and $M_2$ independently represents a metal selected from Si, Ti and Zr;
each occurrence of X independently represents a hydrolysable or nonhydrolyzable group, provided that on each occurrence of $M_1$ and $M_2$, at least one occurrence of X represents a hydrolysable group; wherein (i) when X represents a nonhydrolyzable group, it may be selected from an optionally substituted C1-20 alkyl, C2-20 alkenyl or C2-20 alkynyl moiety, an optionally substituted C1-20 heteroalkyl, C2-20 heteroalkynyl or C2-20 heteroalkynyl moiety, or an optionally substituted phenyl moiety, wherein the substituents on the phenyl, alkyl, alkenyl, alkynyl, heteroalkyl, heteroalkenyl and heteroalkynyl moieties may be independently selected from halogen, —$NO_2$, —CN, isocyano, C1-6 alkoxy, an oxirane/epoxyde moiety, —$N(R)_2$ wherein each occurrence of R is independently selected from H or C1-6 alkyl; and (ii) when X represents a hydrolysable group, it may be selected from a C1-6 alkoxy, C1-6 acyloxy, halogen or amino moiety;
L represents a responsively cleavable covalent bond; and
$R^1$ and $R^2$ independently represent an optionally substituted C1-20alkylenyl moiety, an optionally substituted C1-20heteroalkylenyl moiety, an optionally substituted ethylenyl moiety, —C≡C— or an optionally substituted phenyl moiety, wherein the C1-20alkylenyl, C1-20heteroalkylenyl or ethylenyl moiety may bear one or more substituents selected from halogen or —OR where R may represent H or C1-6alkyl, and the phenyl moiety may bear one or more substituents independently selected from halogen, C1-6alkyl, —$NO_2$, —CN, isocyano, —$OR^p$, —$N(R^p)_2$ wherein each occurrence of $R^p$ independently represents H or C1-6alkyl.

Advantageously, for both methods 1 and 2, the supramolecular template may be made up of any suitable surfactant known in the art to be used in the preparation of porous organometaloxide materials. For example, in a nonlimiting exemplary embodiment, the supramolecular template may be formed of self-aggregated rod-shaped micelles of suitable ionic or non-ionic surfactant molecules.

In an effort to avoid unnecessary repetitions, and for concision purposes, every single variant and embodiments described above in section 1) with respect to variables M, M1, M2, A, m, R1, R2, L, X, the precursors $(X)_3M_1$-$R^1$-$R^2$-$M_2(X)_3$;

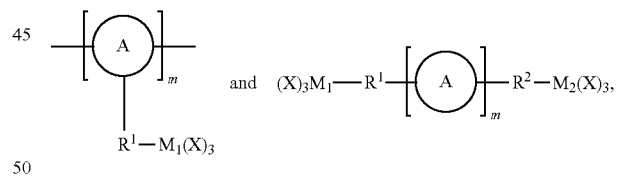

as well as the linkers *—$R^1$-L-$R^2$—*,

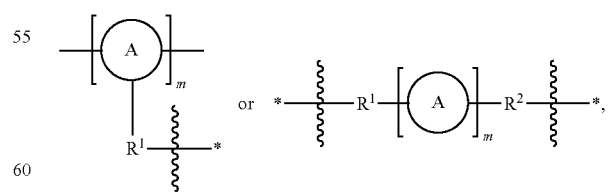

are applicable mutadis mutandis to the synthetic method described immediately above.

It will be appreciated that the exemplary responsively cleavable linkers described herein are for purposes of illustrating and are not in any way meant to limit the scope of the present invention. Other responsively cleavable linkers based on the same concept may also be used. The reader will know how to adapt the teachings described herein, and the Examples for suitable synthetic approaches for these other linkers.

Advantageously, the disintegratable porous organometaloxide material according to the invention may have amorphous pore walls. Advantageously, the disintegratable porous organometaloxide material according to the invention may have crystalline pore walls. Advantageously, the disintegratable porous organometaloxide material according to the invention may have partially crystalline pore walls. Advantageously, the disintegratable porous organometaloxide material according to the invention may have periodically ordered pore walls. Advantageously, the pore walls of the disintegratable porous organometaloxide material according to the invention may be disordered.

For the biological/biodegradable polymer strategy, two different approaches can be pursued: either each of the units of the polymer

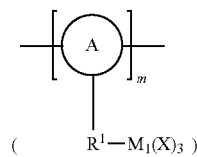

or only the extremities of the polymeric fragment

Figure 2:
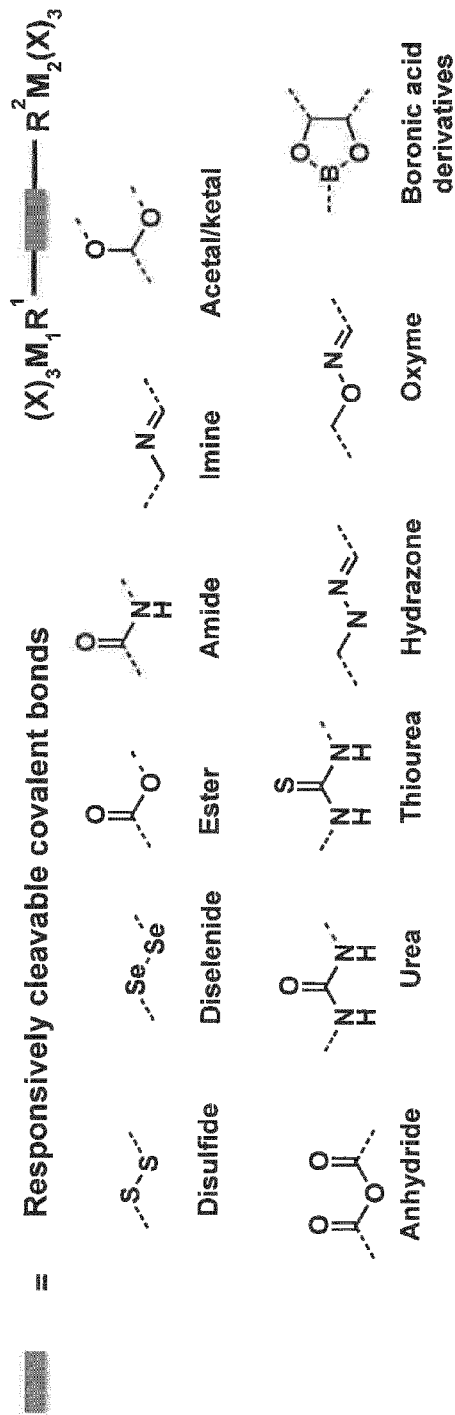
FIG. 2 represents examples of possible responsively cleavable linkers to be incorporated into the porous organometaloxide framework.
Figure 2:
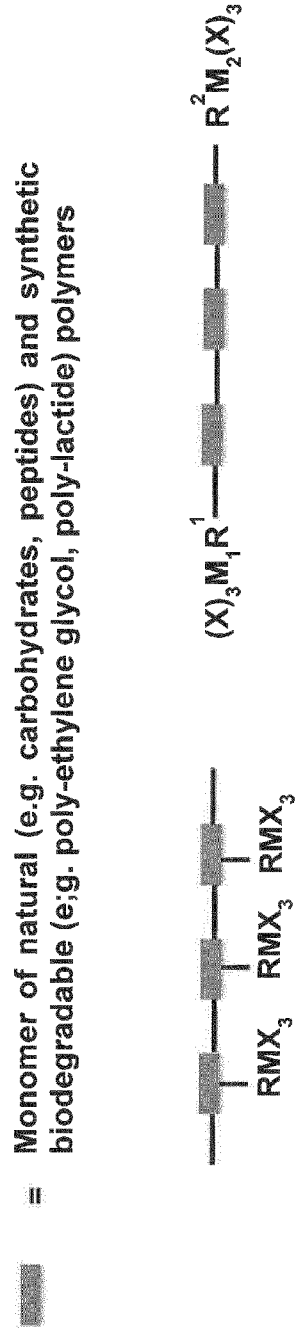
Figure 3:
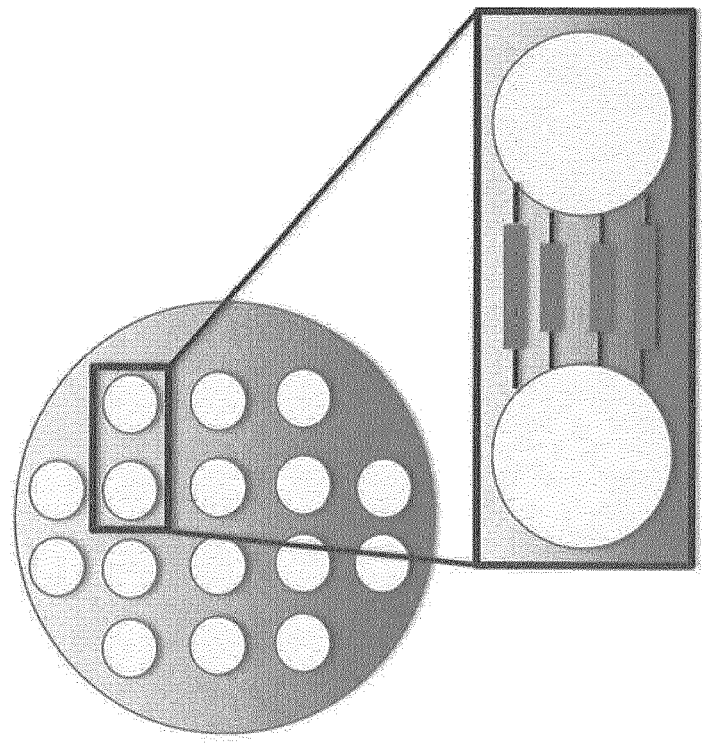
FIG. 3 represents an exemplary tunable reaction procedure to produce the responsively disintegratable porous organometaloxide framework according to the invention.
Figure 3:
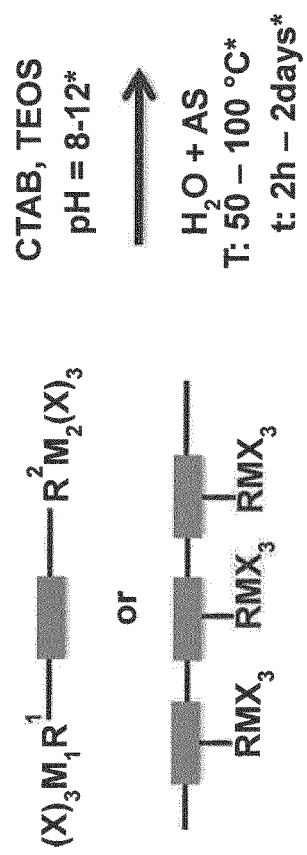

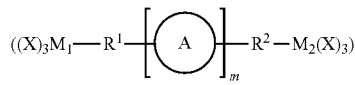

may be equipped with a linking function, of the general formula [(X)$_3$MR-], with X being as defined herein (preferably X may be Cl, Me, OMe, OEt, OPr, OBu) and R having the same definition as R$^1$ and R$^2$ as defined herein, as illustrated at the bottom half of FIG. 2 and FIG. 3.

Advantageously, for both methods 1 and 2, in step b) a pH adjusting agent may be used to modulate the pH to the desired value. As the pH-adjusting agent, there can be mentioned, for example, acids such as sulfuric acid, hydrochloric acid and the like; and alkalis such as sodium hydroxide, ammonia and the like. Advantageously, in the case of disintegratable mesoporous silicon oxide materials according to the present invention, the pH of the reaction system may be preferably adjusted to 0 to 5, most preferably 1 to 5, when an acid agent is used, and to 8 to 14, most preferably, 8 to 13, when an alkaline agent is used.

Advantageously, for both methods 1 and 2, the removing step c) may be carried out using various methodologies depending on the type of responsively cleavable linker:

thermal removal usually means heating in air or oxygen to oxidatively remove said template containing organic-functionalized porous materials from the material obtained in step b), under conditions that do not destroy said terminal organic function.

Photochemical removal usually means irradiating said template containing organic-functionalized porous materials with ultraviolet light in air or oxygen to photooxidatively remove said template from the material obtained in step b), under irradiation conditions that do not destroy said terminal organic function.

Chemical removal usually means reacting said template containing organic-functionalized porous materials with a reagent that serves to chemically remove said template from the material obtained in step b), under conditions that do not destroy said terminal organic function.

Advantageously, refluxing in a solvent in which the template is soluble allows to remove said template, for example by extraction. For example, a solvent like ethanol, methanol, toluene or any other suitable solvent may be used to remove the template.

Embodiments related to organosilica, and particularly mesoporous organosilica, as the porous framework material but it will be described in more details. This is by no means meant to limit the invention to mesoporous organosilica porous frameworks. Similar embodiments related to other metal oxides will be readily apparent to the skilled artisan base don extensive knowledge on the field of sol-gel synthesis of organometaloxides materials (porous or non-porous) and from reading the contents of the present disclosure. As such, the skilled practitioner will know how to adapt the teachings herein to the preparation of disintegratable porous organometaloxides materials other than organosilica, and will be bale to practice the present invention in its full scope.

Disintegratable Porous Silicon Oxide Materials

What follows deals with specific embodiments drawn to disintegratable porous organosilane materials, but the teachings are readily applicable to Ti- and Zr-based materials according to the present invention.

Advantageously, the metal (M, M$_1$ or M$_2$, as defined above) may be Si.

Thus, there is provided a synthetic strategy for creating a new class of disintegratable hybrid mesoporous, macroporous, or mesoporous-macroporous organometaloxide materials, exemplified but not limited to hybrid mesoporous organosilicas. In one aspect, this strategy involves the incorporation of either responsively cleavable covalent bonds or responsively cleavable fragments of biological/biodegradable polymers; directly in the porous framework of the material, as shown as exemplary embodiment in FIG. 1.

The resulting materials, which may be in the form of nanoparticles, are hence able to respond to a specific trigger (e.g., chemical, physical or enzymatic stimulation), by undergoing a structural breakdown. This property leads to an improved porous material with potential for multiple types of application, ranging from controlled release and uptake of chemicals and drugs, or bioassays, cosmetics, catalysis to name a few. Indeed, the unusual behavior of the materials according to the invention confers them an enhanced biodegradability, reducing larger particles into smaller, more easily hydrolysable, and consequently less harmful fragments. This in turn reduces the persistence phenomenon of the materials in their working environment, consequently reducing accumulation risks, and purification/removal costs.

Advantageously, the metal M may be Si and M(X$^A$)$_4$ may represent any Si source suitable for carrying out sol-gel silicon oxide framework synthesis, for example, colloidal silica, sodium silicate, silicon alkoxides, tetramethylammonium silicate and tetraethylorthosilicate (TEOS) and the like. Advantageously, M(X$^A$)$_4$ may represent a tetraalkoxysilanes such as tetramethoxysilane, tetraethoxysilane and tetrapropoxysilane, preferably tetraethoxysilane (TEOS).

Advantageously, the silane precursor M(X$^A$)$_4$ may preferably contain an alkoxysilane having an organic functional group; in other word, at least one occurrence of X$^A$ may be substituted with a substituent bearing an organic functional group, such that it allows further functionalization. Using the alkoxysilane, it is possible to form a silica framework out of alkoxysilyl groups while disposing organic functional groups on the surfaces of the materials. It is further possible to give suitable properties to the mesoporous silica particles by chemically modifying the organic functional group with other organic molecules or the like.

Functionalized organosilane chemistry is well known, and the reader may refer to the following citations for illustrative synthetic guidance that may be readily adapted in the context of the present invention: [6]

Advantageously, the surfactant may be a cationic surfactant, an anionic surfactant, a non-ionic surfactant; preferably a cationic surfactant such as octadecyl trimethyl ammonium bromide, hexadecyl trimethyl ammonium bromide, tetradecyl trimethyl ammonium bromide, dodecyl trimethyl ammonium bromide, decyl trimethyl ammonium bromide, octyl trimethyl ammonium bromide, hexyl trimethyl ammonium bromide and other quaternary ammonium salt-type cationic surfactants. There can also be mentioned, for example, cetyltrimethylammonium bromide (CTAB), cetyltrimethylphosphonium, octadecyltrimethylphosphonium, benzyltrimethylammonium, cetylpyridinium, myristyltrimethylammonium, decyltrimethylammonium, dodecyltrimethylammonium, dimethyldidodecylammonium, pore swelling agents like 1,3,5-trimethylbenzene (TMB) and the like.

Because certain silane precursors $Si(X^4)_4$ like TEOS are not soluble in water alone, a co-solvent, preferably ethanol, may be added. Other solvent such as methanol or DMF can be used. Advantageously, the aqueous solvent comprises an alcohol, such as methanol or ethanol.

Advantageously, the silane precursor $M(X^4)_4$ may be TEOS and the surfactant/TEOS mole ratio can be varied to control the pore-volume fraction in the final material and to vary the pore structure. Also, it will be recognized by those skilled in the art that a much wider range of surfactant sizes and amounts in the family of small polyoxyethylene ethers may be possible with different solvent amounts.

The size and shape of the pores may be controlled by varying the type, the quantity and concentration of surfactant in step a). It will be appreciated that the technique of adding a hydrophobic additive to enlarge mesopores when preparing a mesoporous material is disclosed in prior documents. [10] Thus, in certain embodiments, the method may comprise adding a hydrophobic additive to control the size of the mesopores.

The mixing ratio of the silica precursors $M(X^4)_4$ and $(X)_3Si-R^1-L-R^2-Si(X)_3$ to the surfactant is not particularly limited, but a molar ratio of 3:1 is preferred. If the amount of the surfactant is outside this range relative to the silica precursors, the structure of the product may be less regular, and it may be difficult to obtain mesoporous silica particles with a regular arrangement of mesopores. It is possible to easily obtain mesoporous silica particles with a regular arrangement of mesopores particularly when the molar percentage of linker is in the range but not limited to 10 and 50% of overall silicon source.

As described above, advantageously, a minimum of 30% molar ratio (based on the metal centers) of $(X)_3M_1-R^1-L-R^2-M_2(X)_3$ to 70% of $M(X^4)_4$ precursor may be used, to effect of minimum of 30% doping of the resulting organosilica material. For a doping of 100%, $(X)_3Si-R^1-L-R^2-Si(X)_3$ may be used as the only source of metal (i.e., no $Si(X^4)_4$ is used). For exemplary ratios of equivalents $(X)_3Si-R^1-L-R^2-Si(X)_3/Si(X^4)_4$ to reach a variety of % doping≥30%, see Table 1A.

Likewise, advantageously, a minimum of 5% molar ratio (based on the metal centers) of

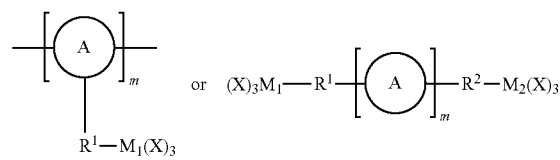

is to 95% of $M(X^4)_4$ precursor may be used. See Tables 1B and 1C.

Advantageously, the linker may comprise a disulfide bond (—S—S—), a peptide bond, an imine bond (—N=CH—) or a carbohydrate moiety, as responsively cleavable bond or moiety.

Advantageously, the precursor having the structure $(X)_3M-R^1-L-R^2-M(X)_3$ may produced in situ. For example, a general synthetic approach for in situ generation of the precursor is depicted in Scheme 1 below:

TABLE 2

Exemplary synthetic conditions for preparing porous organosiliconoxide materials according to the invention

| Exemplary Sol-gel conditions | Responsively cleavable Linker | Exemplary Strategy | Exemplary starting materials |
|---|---|---|---|
| Suitable surfactant, TEOS, auxiliary solvent (e.g., EtOH, DMF, etc.) $(X)_3M_1-R^1-L-R^2-M_2(X)_3$ | L = —S—S— | Commercially available linker. | 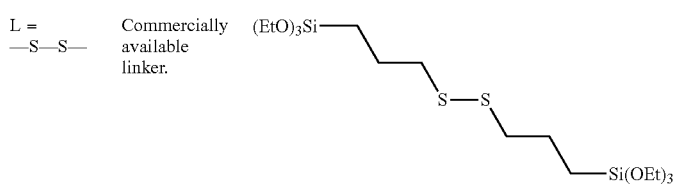 |

TABLE 2-continued

Exemplary synthetic conditions for preparing porous organosiliconoxide materials according to the invention

| Exemplary Sol-gel conditions | Responsively cleavable Linker | Exemplary Strategy | Exemplary starting materials |
|---|---|---|---|
| Suitable surfactant, TEOS, auxiliary solvent (e.g., EtOH, DMF, etc.) $(X)_3M_1-R^1-L-R^2-M_2(X)_3$ | L = —S—S— | Commercially available linker. | $(EtO)_3Si$-propyl-S-S-propyl-$Si(OEt)_3$ |
| Suitable surfactant, TEOS, auxiliary solvent (e.g., EtOH, DMF, etc.) $(X)_3M_1-R^1-L-R^2-M_2(X)_3$ | L = —Se—Se— | Synthesis of a diselenide functionalized with 2 functional groups (e.g. double bonds) reactable with a silane source (e.g. HSi(OEt)$_3$). | bis(4-vinylphenyl) diselenide + HSi(OEt)$_3$ |
| Suitable surfactant, TEOS, auxiliary solvent (e.g., EtOH, DMF, etc.) $(X)_3M_1-R^1-L-R^2-M_2(X)_3$ | L = —C(=O)O— | Synthesis of an ester functionalized with 2 functional groups (e.g. double bonds) reactable with a silane source (e.g. HSi(OEt)$_3$). | vinyl alcohol + acryloyl chloride → vinyl acrylate + HSi(OEt)$_3$ |
| Suitable surfactant, TEOS, auxiliary solvent (e.g., EtOH, DMF, etc.) $(X)_3M_1-R^1-L-R^2-M_2(X)_3$ | L = —C(=O)NH— | Bis-carboxylic acid molecule derivatized with a silane source (e.g. APTES). | succinic acid + (EtO)$_3$Si-propyl-NH$_2$ (2 eq.) |
| Suitable surfactant, TEOS, auxiliary solvent (e.g., EtOH, DMF, etc.) $(X)_3M_1-R^1-L-R^2-M_2(X)_3$ | L = —N=CH— | Condensation of an aldehyde (e.g. 4-(triethoxysilyl)butanal) and an amino-derivatized silane (APTES). | (EtO)$_3$Si-propyl-NH$_2$ + (EtO)$_3$Si-butyl-CHO |
| Suitable surfactant, TEOS, auxiliary solvent (e.g., EtOH, DMF, etc.) $(X)_3M_1-R^1-L-R^2-M_2(X)_3$ | L = -Acetal/ketal | Synthesis of acetals functionalized with 2 functional groups (e.g. double bonds) reactable with a silane source (e.g. HSi(OEt)$_3$). | divinyl spiro-bis-dioxane + HSi(OEt)$_3$ |

TABLE 2-continued

Exemplary synthetic conditions for preparing porous organosiliconoxide materials according to the invention

| Exemplary Sol-gel conditions | Responsively cleavable Linker | Exemplary Strategy | Exemplary starting materials |
|---|---|---|---|
| Suitable surfactant, TEOS, auxiliary solvent (e.g., EtOH, DMF, etc.) $(X)_3M_1—R^1—L—R^2—M_2(X)_3$ | L = —S—S— | Commercially available linker. | (EtO)$_3$Si—\—\—S—S—\—\—Si(OEt)$_3$ |
| Suitable surfactant, TEOS, auxiliary solvent (e.g., EtOH, DMF, etc.) $(X)_3M_1—R^1—L—R^2—M_2(X)_3$ | L = -Anhydride | Synthesis of an anhydride functionalized with 2 functional groups (e.g. double bonds) reactable with a silane source (e.g. HSi(OEt)$_3$). | CH$_2$=CH—(CH$_2$)$_n$—C(O)—O—C(O)—(CH$_2$)$_n$—CH=CH$_2$ + HSi(OEt)$_3$ |
| Suitable surfactant, TEOS, auxiliary solvent (e.g., EtOH, DMF, etc.) $(X)_3M_1—R^1—L—R^2—M_2(X)_3$ | L = -Urea/ thiourea | Condensation of an isocyannate (e.g. 3-(Tri-ethoxysilyl)-propyl isocyan-nate) and an amino-deriva-tized silane (e.g. APTES). | (EtO)$_3$Si—\—\—NCO + (EtO)$_3$Si—\—\—NH$_2$ |
| Suitable surfactant, TEOS, auxiliary solvent (e.g., EtOH, DMF, etc.) $(X)_3M_1—R^1—L—R^2—M_2(X)_3$ | L = —N—N=CH— | Functionaliza-tion of an hydrazone with a silane deriva-tive (e.g. 3-(tri-ethoxysilyl)-propyl isocyan-nate). | CH$_3$—C(O)—(CH$_2$)$_n$—C(O)—CH$_3$ + NH$_2$NH$_2$ → H$_2$N—N=C(CH$_3$)—(CH$_2$)$_n$—C(CH$_3$)=N—NH$_2$ + (EtO)$_3$Si—\—\—NCO |
| Suitable surfactant, TEOS, auxiliary solvent (e.g., EtOH, DMF, etc.) $(X)_3M_1—R^1—L—R^2—M_2(X)_3$ | L = —O—N=CH— | Functionaliza-tion of an oxyme with a silane derivative (e.g. 3-(triethox-ysilyl)-propyl chloride). | OHC—(CH$_2$)$_n$—CHO + NH$_2$OH → HO—N=CH—(CH$_2$)$_n$—CH=N—OH + (EtO)$_3$Si—\—\—Cl |
| Suitable surfactant, TEOS, auxiliary solvent (e.g., EtOH, DMF, etc.) $(X)_3M_1—R^1—L—R^2—M_2(X)_3$ | L = -Boronic acid derivatives | Complexation with a tetraalco-hol (i.e penta-erithritol) of a boronic acid possessing with 2 functional groups (e.g. double bonds) reactable with a silane source (e.g. HSi(OEt)$_3$). | C(CH$_2$OH)$_4$ + 4-(B(OH)$_2$)-C$_6$H$_4$-CH=CH$_2$ (2 eq.) + HSi(OEt)$_3$ |

TABLE 2-continued

Exemplary synthetic conditions for preparing porous organosiliconoxide materials according to the invention

| Exemplary Sol-gel conditions | Responsively cleavable Linker | Exemplary Strategy | Exemplary starting materials |
|---|---|---|---|
| Suitable surfactant, TEOS, auxiliary solvent (e.g., EtOH, DMF, etc.) $(X)_3M_1-R^1-L-R^2-M_2(X)_3$ | L = —S—S— | Commercially available linker. | $(EtO)_3Si$—\\—S—S—\\—$Si(OEt)_3$ |
| [diagram with A and R¹] | A = Carbohydrates | Functionalization of the monomers of a carbohydrate (e.g. amilose) with epoxy terminating silane derivative (i.e. 3-glycidoxypropyl triethoxy silane). | [glucose structure] + $(EtO)_3Si$—\\—O—\\—epoxide |
| [diagram with A and R¹] | A = Peptides | Functionalization of the monomers of a polypeptide (e.g. Polylysine) with an isocyanate terminating silane derivative (e.g. 3-triethoxysilyl)-propyl isocynnate). | [polylysine structure] + $(EtO)_3Si$—\\—NCO |
| [diagram with A, R¹, R²] | A = Biodegradable polymers | Functionalization of the monomers of the extremities of a biodegradable polymer (e.g. PEG) with an epoxy terminating silane derivative (e.g. 3-glycidoxypropyl triethoxy silane) | $HO$—(—O—)ₙ—$H$ + $(EtO)_3Si$—\\—O—\\—epoxide (2 eq.) |

Scheme 1: Exemplary synthesis of a pH responsive linker (M = Si).

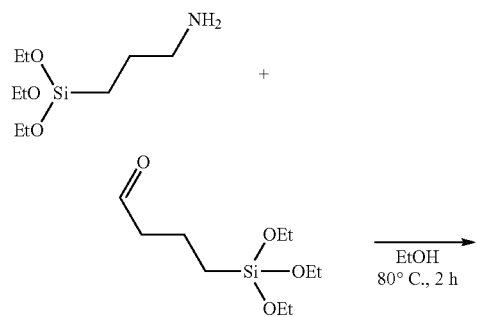

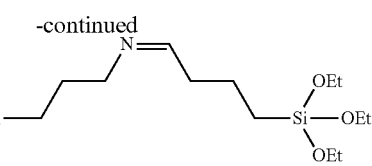

-continued

In this aspect of the invention the step of preparing a porous framework material may include synthesizing the porous framework material by mixing the precursors (($X_3Si$)R1-L-R2($SiX_3$); and $Si(X^A)_4$) of the framework material with a suitable supramolecular template under conditions suitable for self-assembly of the particulate constituent to form the framework material, and subsequent removing the supramolecular template. The framework material being an organometaloxide, which may be mesoporous, macroporous, or combined mesoporous-macroporous having a porosity containing both size regimes of pores. The metaloxide may be silica.

The method for producing disintegratable porous silica materials of the present invention is not particularly limited, but the method preferably includes the following steps. The first step is a "surfactant micellar assembly step" wherein the surfactant serve as template for the porous organosiliconoxide material (step a)). The next step is a "organosiliconoxide covering step" comprising:

Method 1: adding a silica source $Si(X^A)_4$ to the surfactant template, together with a suitable precursor $(X)_3M_1$-$R^1$-L-$R^2$-$M_2(X)_3$,

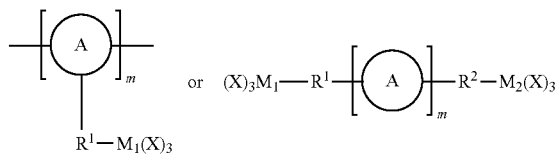

(where M=M1=M2=Si), to thereby cover the surface (periphery) of the surfactant template with organosiliconmetaloxide (step b)); or Method 2: adding a suitable precursor $(X)_3M_1$-$R^1$-L-$R^2$-$M_2(X)_3$,

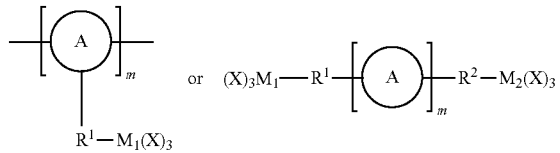

(where M1=M2=Si), to the surfactant template, to thereby cover the surface (periphery) of the surfactant template with organosiliconmetaloxide (step b)).

As discussed before, for method 1, advantageously, the mixing ratio of the silica sources $(X)_3Si$—$R^1$-L-$R^2$—$Si(X)_3/Si(X^A)_4$;

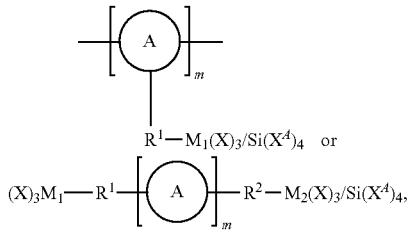

respectively, may be adjusted to control the desired % doping in the resulting porous organosiliconmetaloxide material. For exemplary ratios of equivalents $(X)_3Si$—$R^1$-L-$R^2$—$Si(X)_3/Si(X^A)_4$ to reach a variety of % doping≥30%, see Table 1A. See also Tables 1B and 1C for the polymer A version.

The final step is a "removal step" of removing the surfactant template (step c)). The final step may be performed or not depending on the type/use of the surfactant.

Advantageously, the surface of the porous silica material according to the invention may be functionalized with a surface agent, for example by using a function group-containing trialkoxysilane, such as a PEG group linked to a trialkoxysilane. Likewise, marking of the porous silica material (for example for medical purposes) may be achieved by condensation of a marker-containing trialkoxysilane. The marker may be selected from a contrast agent, a tracer, a radioactive marker, any commercial dye, such as a fluorescent marker or a phosphorescent marker, a magnetic resonance imaging agent or a positron emission tomography agent, such as pyrene, rhodamine, IR783, Gd-EDTA or $^{64}Cu$-EDTA. The marker may be a fluorescent molecule selected from rhodamines, fluorescein, luciferase, pyrene-containing markers, aminopyrrolidino-7-nitrobenzofurazan, or indocyanine green (ICG) for NIR emission.

As used herein, the term "surface agent" refers to a molecule that partly or totally covers the surface of the porous material, allowing the surface properties of the material to be modified, for example:
- modifying its biodistribution, for example to avoid its recognition by the reticulo-endothelial system ("furtiveness"), and/or
- giving it advantageous bioadhesion properties during oral, ocular or nasal administration, and/or
- enabling it to specifically target certain sick organs/tissues, etc.

According to the invention, several surface agents may be used to combine the abovementioned properties. For example, a surface agent combining at least two of the abovementioned properties may be used. For example, the organic surface agent may be chosen from:
- an oligosaccharide, for instance cyclodextrins,
- a polysaccharide, for instance chitosan, dextran, fucoidan, alginate, pectin, amylose, starch, cellulose or xylan,
- a glycosaminoglycan, for instance hyaluronic acid or heparin,
- a polymer, for instance polyethylene glycol (PEG), polyvinyl alcohol or polyethyleneimine,
- a surfactant, such as pluronic or lecithin,
- vitamins, such as biotin,
- coenzymes, such as lipoic acid,
- antibodies or antibody fragments,
- amino acids or peptides.

3) Compositions and Uses

The porous organometaloxide framework materials of the invention are useful for any known use of porous organometaloxide framework materials known in the art. The porous organometaloxide framework materials of the invention are particularly adapted for uses of this type of materials where the self-destructive behavior that characterizes the organometaloxide of the invention provides an advantage. In particular, in contrast to conventional porous organometaloxide framework materials known in the art, the materials of the invention have the unexpected property of completely losing their structural integrity (disintegration) upon application of a suitable stimuli. Owing to the intrinsic porosity combined to their disintegratable properties, the materials of the invention prove much more efficient in releasing and delivering compounds that they might be loaded with (e.g., therapeutically and/or cosmetically active principles, or other chemicals). In other words, release of the compounds trapped/encapsulated in the materials' porous framework occurs much more efficiently than with conventional porous organometaloxides known in the art. For biomedical applications (e.g., when the framework metal is Si), this means less bio-accumulation, better elimination, and less toxicity.

These uses include:

Biomedical applications, including controlled drug release and uptake, and their use in sensing, diagnostics and bioassays. See for example WO2005087369, WO2011124739, WO2009024635, us2013195963, us20100278931

Cosmetics WO 2010030252, JP 2002348380, WO 2010030252

Catalysis KR 2013113770

Photovoltaics WO 2013154964, US 20130269782

Inks/Paints additive WO2011119265 A1, U.S. Pat. No. 4,877,451 A

Optical coating WO 2012022983 A1

Anti-microbial WO2006120135 A1

Accordingly, there is provided compositions comprising a disintegratable porous organometaloxide framework material according to the invention and any compound and/or additive suitable for any one or more of the material's intended use describe above.

Thus, for applications that involve a disintegratable porous organometaloxide framework material according to the invention loaded with one or more compounds (for medical or cosmetic uses for example), the process for preparing the porous organometaloxide materials according to the invention may further comprise a step (d) of introducing, into the pores or at the surface of the porous organometaloxide materials, at least one molecule of interest, which may be a pharmaceutically active principle and/or a marker. Any method known to those skilled in the art may be used to that end. The molecule of interest may be introduced, for example, into the porous organometaloxide materials of the present invention:

- via impregnation, by immersing the material in a solution of the molecule of interest;
- by sublimation of the molecule of interest, and the gas is then adsorbed by the material; or
- via rotary roll milling, which consists in mechanically mixing the material and the molecule of interest.

The form of the porous material of the invention may be adapted to fit the intended use. For example, for applications in catalysis, the disintegratable porous organometaloxide framework material according to the invention may be in the form of a monolith or fragments. For ink, paint, biomedical or cosmetic applications, the disintegratable porous organometaloxide framework material according to the invention may be in the form of nanoparticles. For separation/purification and catalysis applications, the disintegratable porous organometaloxide framework material according to the invention may be in the form of thin or thick films.

In one aspect, for medical applications, a composition according to the invention may comprise a disintegratable porous organometaloxide framework material according to the invention loaded with a pharmaceutically active principle and/or a marker, for example in its pores.

In another aspect of the present invention, pharmaceutically acceptable compositions are provided, wherein these compositions comprise any of the porous organometaloxide materials as described herein, and optionally comprise a pharmaceutically acceptable carrier, adjuvant or vehicle. In certain embodiments, these compositions optionally further comprise one or more additional therapeutic agents.

The use of carriers and vectors for molecules of interest, especially molecules with a therapeutic effect or markers, has become a major issue for the development of novel diagnostic methods or novel medicaments. Specifically, the molecules of interest have characteristics that have an influence on the pharmacokinetics and biodistribution of these molecules and that are not always favorable or adaptable to the medium into which they are introduced. They are, for example, physicochemical characteristics, such as instability, a strong tendency toward crystallization, poor water solubility and/or biological characteristics such as toxicity, biodegradability, etc.

The porous organometaloxide materials according to the invention may be used for that purpose, namely for drug delivery, and for improving the pharmacokinetic profile of drugs, for example in terms of escaping the immune system and/or uptake by certain organs, for example the liver or the kidney, thus avoiding their accumulation in these organs.

There is thus provided porous organometaloxide materials (for example in the form of nanoparticles) for use as medicament and/or drug delivery/controlled release. For example, the porous organometaloxide materials may comprise in their pores or at their surface at least one pharmaceutically active principle. There is also provided porous organometaloxide materials (for example in the form of nanoparticles), for use in medical imaging. For example, the porous organometaloxide materials may comprise in their pores or at their surface at least one marker. There is also provided a method for treating a condition or disease comprising administering to a subject in need thereof a disintegratable porous organometaloxide material according to the present invention, appropriately loaded on its surface or in its pore with a drug moiety adapted for such treatment.

Likewise, for cosmetic applications, a composition according to the invention may comprise a disintegratable porous organometaloxide framework material according to the invention loaded with a cosmetically active principle, for example in its pores.

In another aspect, the invention provides the use of disintegratable porous organometaloxide framework material according to the invention in a cosmetic composition.

In another aspect, the invention provides the use of disintegratable porous organometaloxide framework material according to the invention in catalysis.

In another aspect, the invention provides the use of disintegratable porous organometaloxide framework material according to the invention in photovoltaics.

The disintegratable porous organometaloxide materials according to the invention therefore can find applications in in vitro and in vivo diagnostics, therapy, in cosmetics, in drug delivery, and in any other application where a release can be envisaged.

Other advantages may also emerge to those skilled in the art upon reading the examples below, with reference to the attached figures, which are provided as nonlimiting illustrations.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

The present invention will now be exemplified using mesoporous organosilica as the porous framework material but it will be understood this is not meant to limit the invention to mesoporous organosilica porous frameworks.

The tested particles will be tested in their triggered degradation ability, and evidence of the breakdown of the material will be given by demonstrating the structural/morphological transformations occurring in the responsively disintegratable particles during the triggered breakdown process.

Example 1—Introducing an S—S Bond in the Framework of Mesoporous Silica Nanoparticles (SNPs)

Synthesis
  Synthesis of 20 nm average diameter S—S doped SNPs: CTAB (145 mg) was added to a mixture of 72 ml of $H_2O$, 3 ml of EtOH, and 0.6 ml of a 28 wt % ammonia solution. The reaction mixture was stirred at 50° C. for 1 h before the addition of 1.25 ml of a 0.88 M ethanolic solution of: the disulfide silane (bis(3-triethoxysilyl-propyl)disulfide, 30% in molar ratio with respect to the Si centers), phosphonated silane (3-(trihydroxysilyl) propyl methylphosphonate monosodium salt, 3%); and Tetraethyl orthosilicate (TEOS) (67% in molar ratio with respect to the Si centers). The above reaction mixture was continuously stirred for 24 h at 70° C. The Cetyltrimethylammonium bromide (CTAB) mesoporous template was then removed by stirring the sample in acidic ethanol (50 ml) at 90° C. for 12 h. The resulting solid was recovered by centrifugation, washed with water and ethanol several times, and finally preserved in water as a suspension.
  Fluorescein-tagging of SS doped SNPs (SS-NPs): the S—S doped SNPs were dispersed in 20 ml of toluene, before adding to the suspension a solution of fluorescein isothiocyanate (FITC) and (3-aminopropyl)-triethoxysilane (APTES) in ethanol, characterized by a concentration of 0.5 mmol per mg of NPs to be functionalized. The suspension was then heated at reflux for 14 h. The resulting solid was recovered by centrifugation, washed with toluene, water and ethanol several times, and finally preserved in water.
  Chemical biodegradability test: reduction of the S—S bond was performed with $NaBH_4$, being an efficient and irreversible reducing agent, not forming residual by-products, which might hamper visual evaluation of the efficacy of the reduction. In a typical reduction experiment, $NaBH_4$ (1 mg) was added to a stable suspension of the luminescent SS-NPs in MeOH (1 mg/ml). After 6 hours, the reaction was quenched by addition of a small amount of water (0.1 ml) to deactivate unreacted $NaBH_4$.

Figure 4:
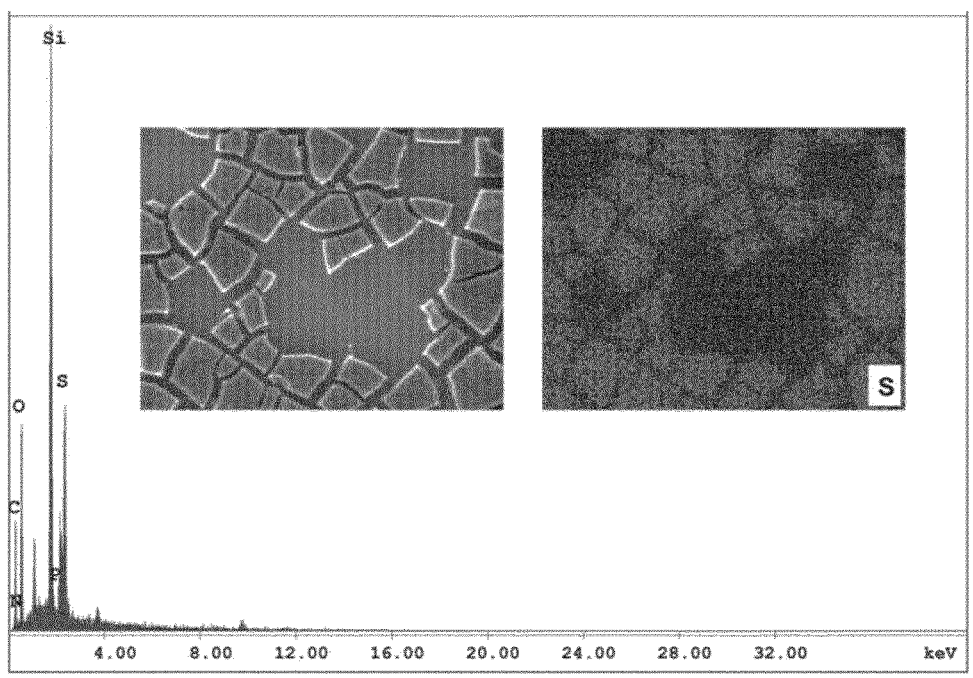
FIG. 4 represents EDX spectra and map of the fluorescein-tagged SS-NPs prepared in Example 1.
Figure 5:
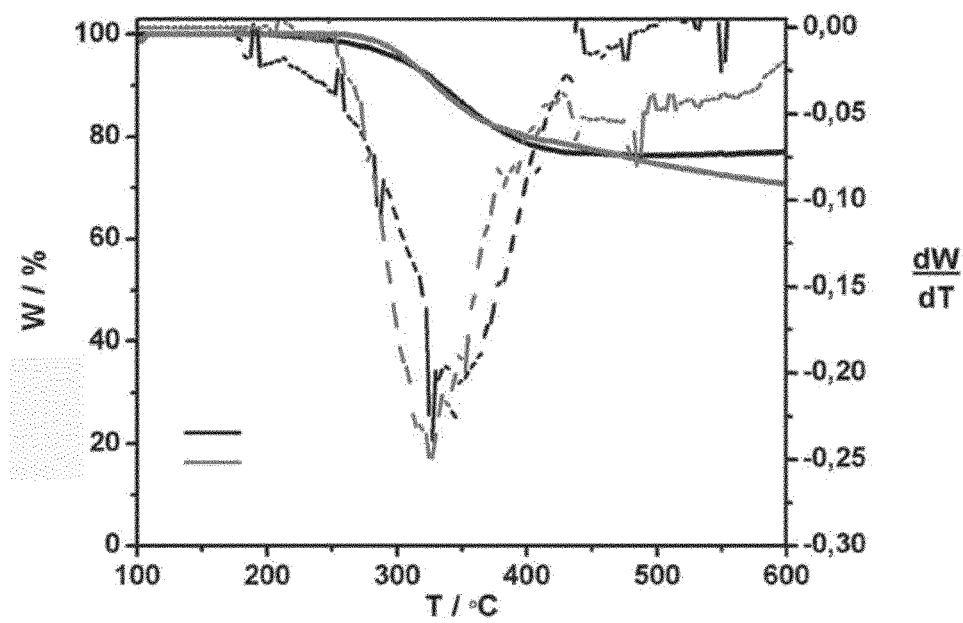
FIG. 5 represents a TGA analysis of the SS-NPs of Example 1 before (black line) and after functionalization with fluorescein (grey line). In dashed lines the relative derivatives.
Figure 6:
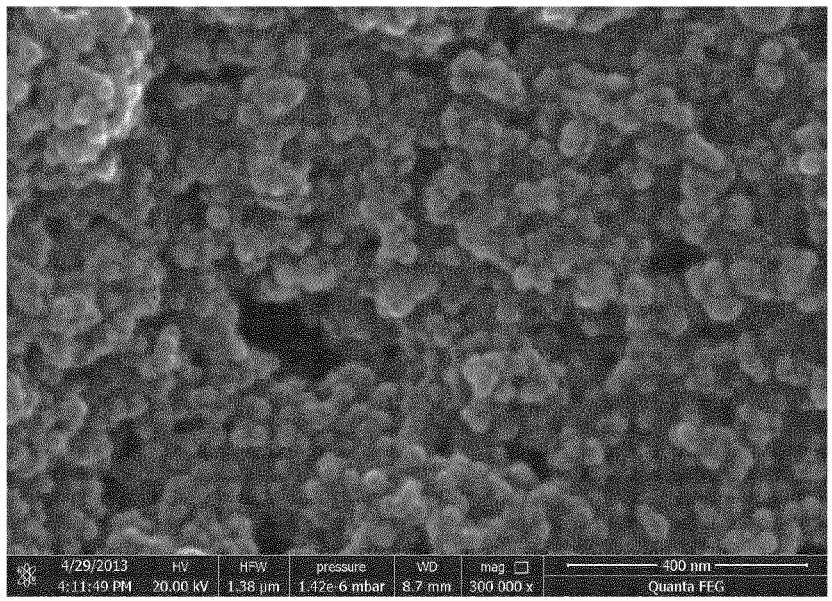
FIG. 6 represents an SEM image of SS-NPs of Example 1.
Figure 7:
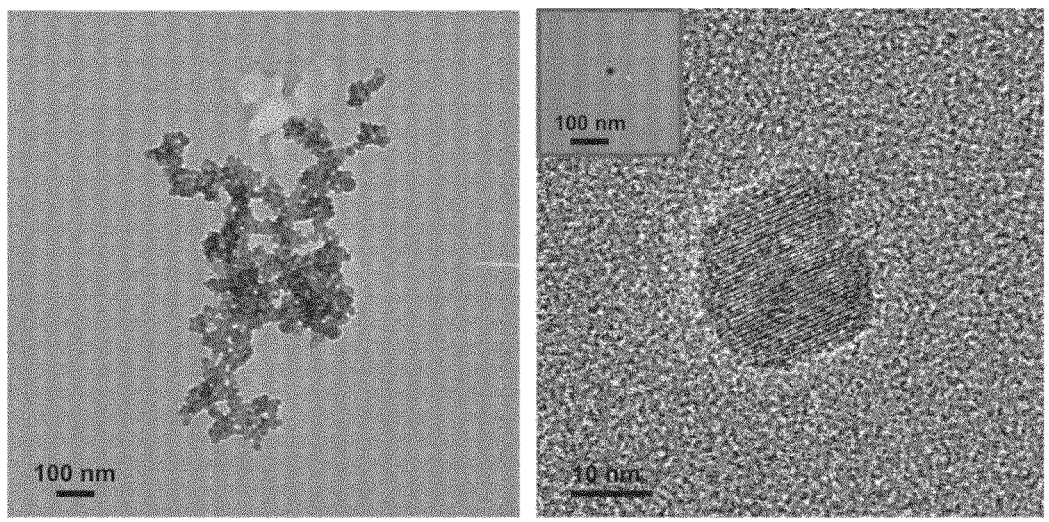
FIG. 7 represents TEM and HRTEM images of SS-NPs of Example 1. On the right image it is possible to notice the ordered channels.
Figure 8:
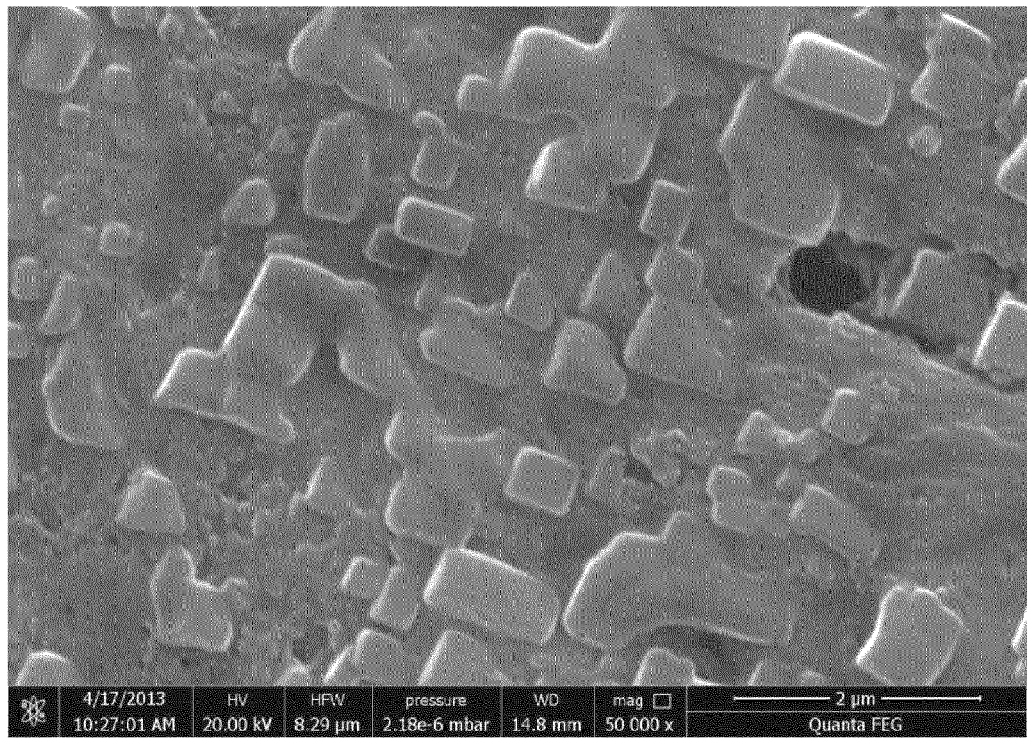
FIG. 8 represents an SEM image of the reduced SS-NPs of Example 1.
Figure 9:
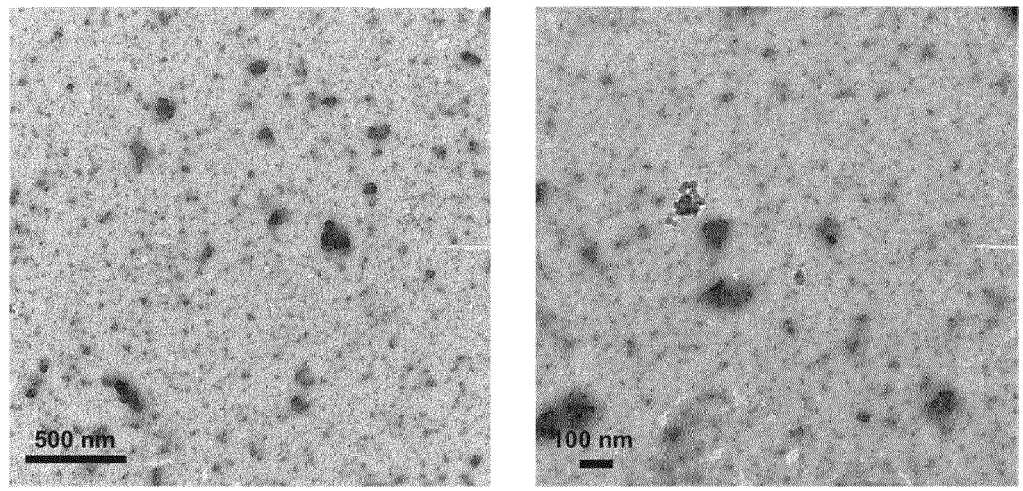
FIG. 9 represents a TEM analysis of the SS-NPs of Example 1 treated with $NaBH_4$.
Figure 10:
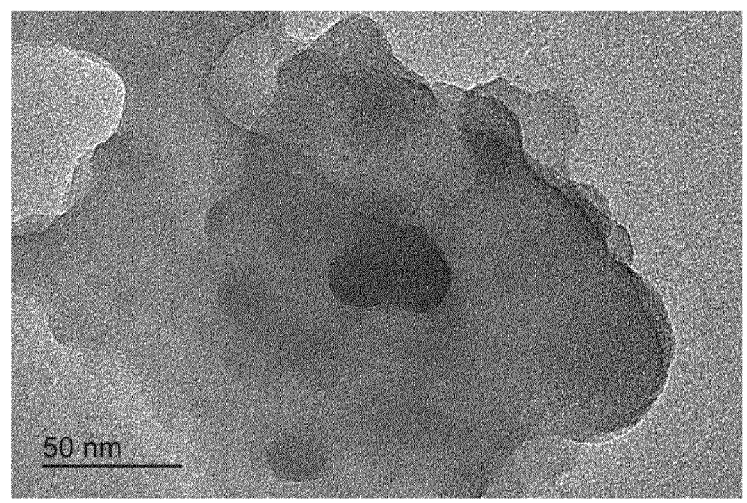
FIG. 10 represents a HRTEM analysis of the reduced SS-NPs of Example 1.
Figure 11:
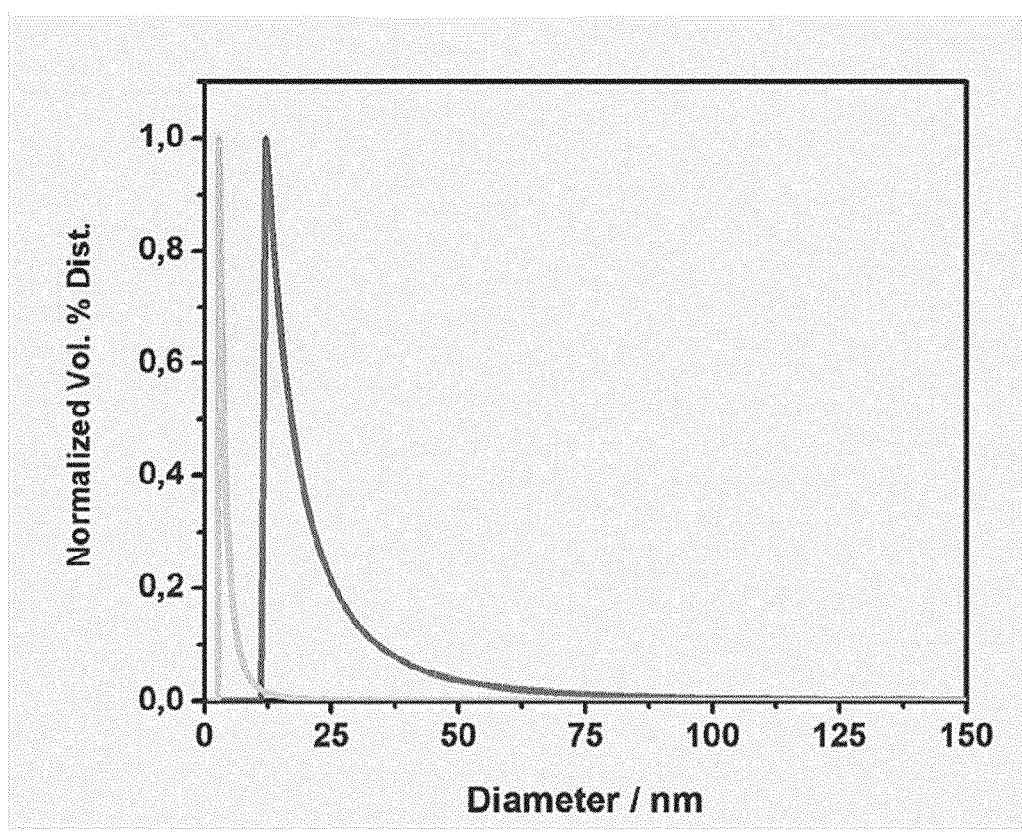
FIG. 11 represents a DLS analysis of the SS-NPs of Example 1 before (dark grey line) and after degradation with $NaBH_4$ (light grey line).
Figure 12:
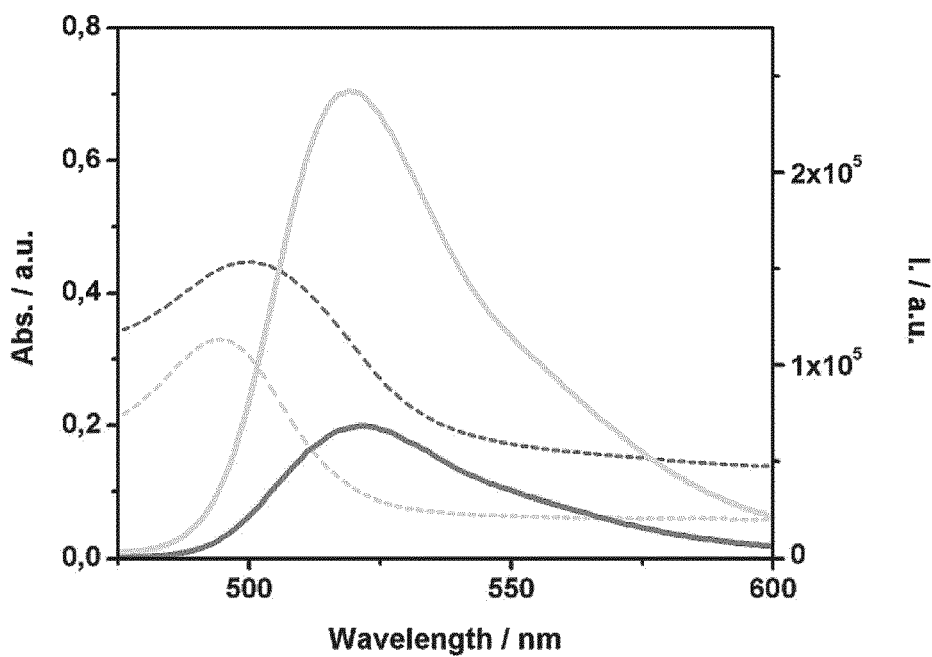
FIG. 12 represents absorption (dashed lines) and emission profiles (thick lines) of the SS-NPs of Example 1 before (dark grey line) and after (light grey line) reduction with $NaBH_4$.
Figure 13:
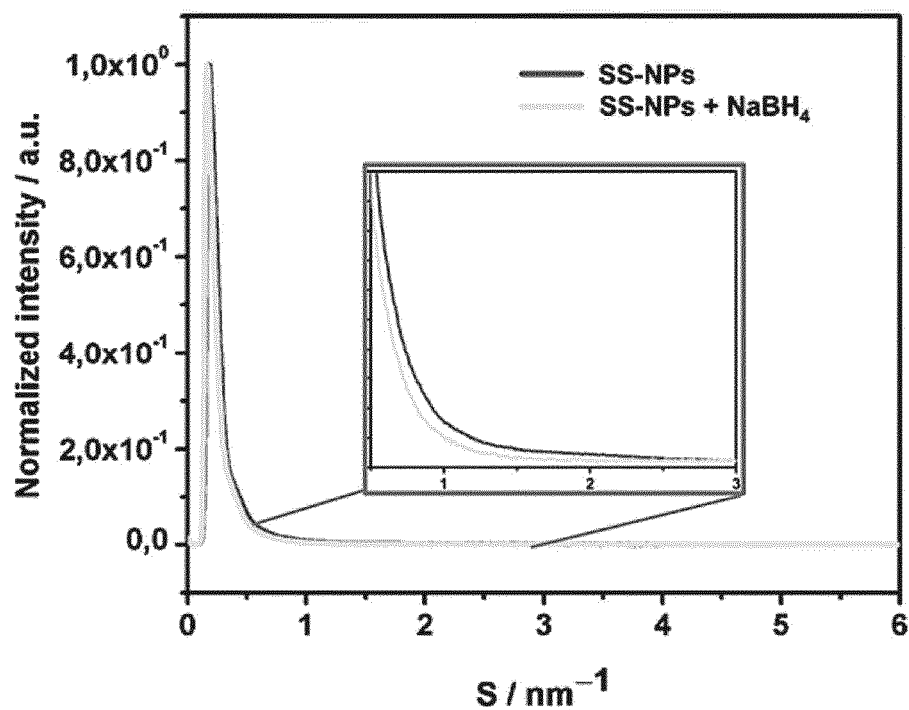
FIG. 13 represents an SAXS analysis of the SS-NPs of Example 1 before (dark grey line) and after (light grey line) reduction.
Figure 14:
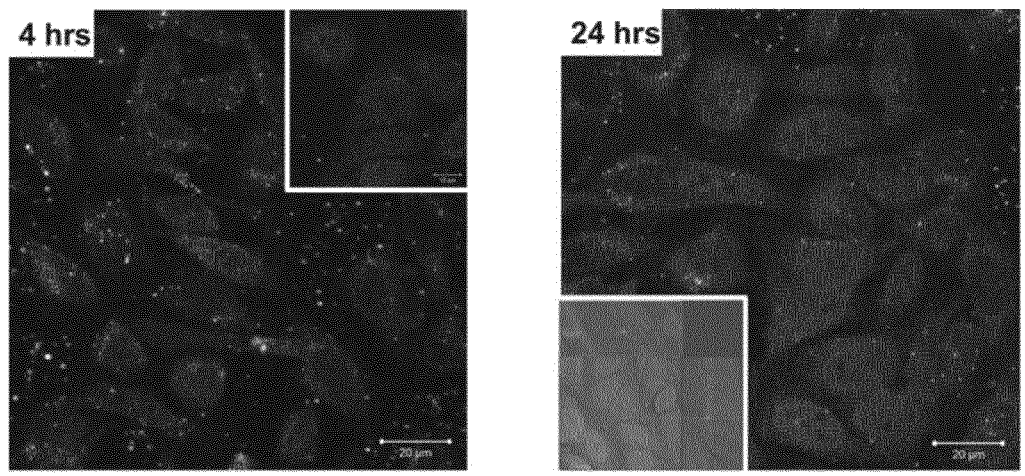
FIG. 14 represents confocal microscope images of the SS-NPs of Example 1 incubated in Hela cells for 4 hours, and 24 hours. After 1 day, degradation initiates and the particles seem to solubilize inside the biological environment. In the inset, Z-stack analysis of the internalized nanoparticles.
Figure 15:
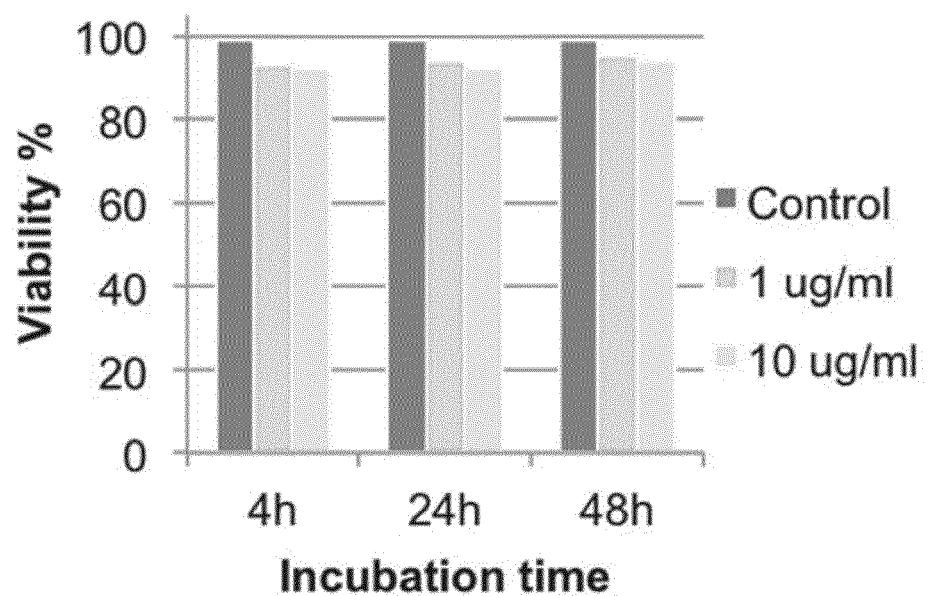
FIG. 15 represents a viability screening of the effect of the internalization of SS-NPs of Example 1 inside HeLa cells.
Figure 16:
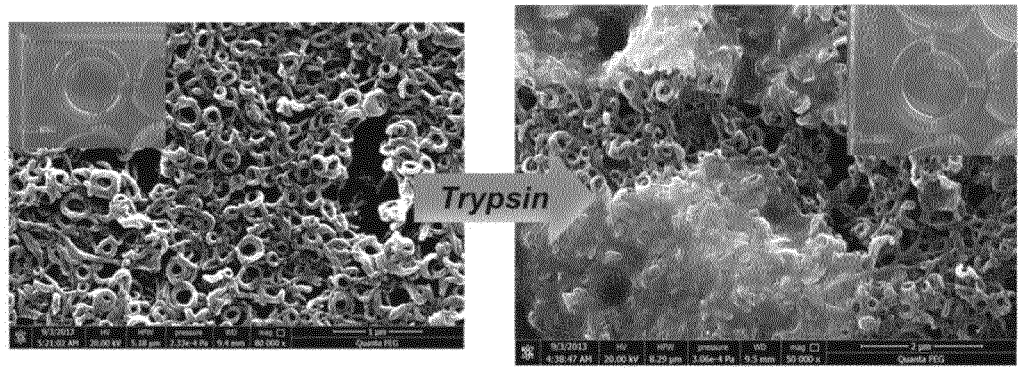
FIG. 16 represents images of the Rho-tagged Pep-SNPs of Example 2 before and after the addition of trypsin to the suspension. In the insets, images of the reaction environment, showing the precipitation of the material that interacted with the enzyme.

Analysis and Results
  Characterization of the composition of the nanoparticle was firstly performed by means of electron diffraction X-ray spectroscopy (EDX) and thermogravimetric analysis (TGA), in order to confirm the presence of the linker in the structure of the particle (FIG. 4-5). The EDX spectrum and EDX map shown in FIG. 4 reports the presence of the signal of S in the material, clearly confirming the introduction of the disulfide bridge in the SS-NPs' structure.
  The presence of the organic fragments was further sustained by thermogravimetric analysis. From the TGA plot it resulted possible to detect the content of organic material in the NPs, characterized by a lower decomposition temperature compared to the silica framework. Indeed, as demonstrated in FIG. 4, the pristine SS doped NPs are characterized by a percentage weight loss of 23% at 350° C. This data corresponds to a presence of disulfide bridging ligand. For the fluorescein functionalized SS-NPs a weight loss of 30% was instead recorded at 350° C., due to the further functionalization with the dye.
  Scanning Electron Microscopy (SEM), Transmission Electron Microscopy (TEM) and high resolution Transmission Electron Microscopy (HRTEM) were used to confirm the nanoparticle morphology of the synthesized responsively disintegratable material, as well as the presence of the porous framework (FIG. 6-7). It was hence determined that the average diameter of the particles results around 20 nm. After the chemical degradation, the porous structure was lost, and only small particle fragments, or amorphous silica was detected in the sample (FIG. 8-10).
  Important evidence of the degradation in solution came from Dynamic light scattering (DLS) analysis (FIG. 11). As can be clearly seen the initial size of the nanoparticles (19 nm±10) is completely changed after the reduction reaction and the particles size is reduced to 5 nm±3.
  Absorption (UV-Vis) and emission properties of the SS-NPs were evaluated before and after their reduction (FIG. 12). Regarding the absorption properties, after the reduction, the broken particles' suspension presents a much lower degree of scattering, due to the reduced size of the particles. Also the luminescence of the reduced material increases considerably, indicating a lower quenching occurring from the particles, again attributable to the smaller size of the reduced material.
  Small angle X-ray scattering (SAXS) analysis confirmed the HRTEM results, indicating that the synthesized responsively disintegratable SS-NPs indeed present a mesoporous network, which is partially lost after the breaking experiment.
  To prove that these pores system can be used in biomedicine and that the degradation can occur also in biological systems, where for biological systems is intended cells, bacteria, virus, cell experiment were done.
  The cell up-take of SS-NPs was tested with Hela cells. As depicted in FIG. 14, the results show that the NPs are internalized by the cells. The NPs have been labeled with a green fluorescent dye and therefore the localization of the porous particles and the dye will be the same if the particles are not degraded. Indeed this is the case for the first 4 hours (FIG. 14 left). However after longer time incubation the fluorescein seems to diffuse inside the cell, suggesting the occurring decomposition of the particles in the cellular environment and the spreading of the small resulting pieces all over the cytoplasm (FIG. 14 right). To prove that the fragments are not toxic viability tests have been performed on the cell monitoring their death after 4, 24 and 48 hours. The results shown in FIG. 15 do not show any mortality of the cells.

Example 2—Introducing a Small Peptide in the Framework of Mesoporous Silica Nanoparticles Synthesis
  Synthesis of trilysine-doped mesoporous silica nanoparticles (Pep-SNPs): CTAB was dissolved in a mixture of $H_2O$ and 28 wt % ammonia solution (amount depending on the requested morphology). The reaction mixture was stirred at 50° C. for 1 h before the addition of a solution of Tri-lysine (LLL), containing 6 mg of the peptide, 27 µl of 3-(Triethoxysilyl)propyl isocyanate (NCO-PTES), 15 µl of TEA in 1 ml of DMF. The above described reaction mixture was hence stirred for an additional 2 h at 50° C. The CTAB mesoporous template was removed by stirring the sample in ethanol (50 ml) at 50° C. for 6 h. The resulting solid was recovered by centrifugation, washed with water and ethanol several times, and finally preserved in water as a suspension.
  Rhodamine-tagging of the Pep-SNPs: the peptide doped NPs were dispersed in 50 ml of EtOH, before adding to the suspension a solution of rhodamine B isothiocyanate (RITC) in EtOH, characterized by a concentration of 0.5 mmol per mg of NPs to be functionalized. The suspension was then heated at reflux for 14 h. The resulting solid was recovered by centrifugation, washed with ethanol and water several times, and finally conserved in water.
  Biodegradability test: destruction of the Rho-tagged Pep-SNPs was performed upon exposure of the particles to an enzyme (trypsin), able to attack and destroy the peptide fragment introduced in the framework of the material. Specifically, in a typical experiment, trypsin (50 µl) was added to a stable suspension of the luminescent Pep-SNPs (0.1 mg/ml) in a 1 w % dispersion of poly-lysine in water, and the mixture incubated at 37.5° C. for 3 days.

Figure 17:
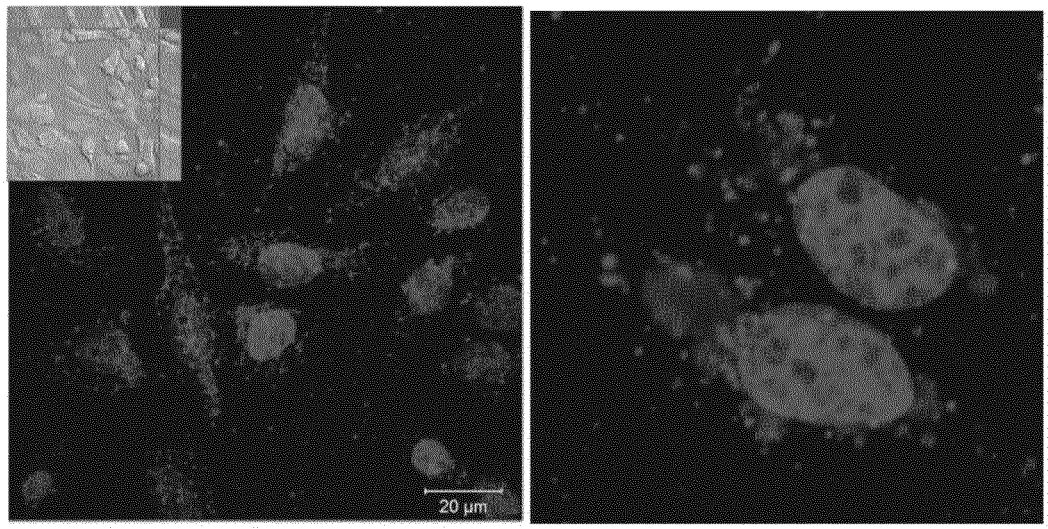
FIG. 17 Left: confocal microscope imaging of Hela cells incubated with the Rho-tagged SNPs of Example 2, taken after 48 hours incubation. In the inset: the Z-scan of the Rho-Pep-SNPs of Example 2 demonstrating their internalization. Right: highlight of cells in which the decomposition of the particles has started.

Analysis and Results
  To prove that the degradation can also enzymatically triggered a small peptide was introduced in the framework of mesoporous silica nanoparticles. The results clearly indicated that also in this case a full breaking of the silica is observed and the supported experiments are reported below.
  Scanning electron microscopy (SEM) images of Pep-SNPs before and after exposure to the trypsin enzyme highlight a difference in the morphology of the material. In fact, the typical annular morphology of the particles is lost, and mainly amorphous silica is detected.
  The cell up-take of Rho-tagged Pep-SNPs was also tested with Hela cells. As depicted in FIG. 17, preliminary results show that the NPs are up-taken by the cells (average viability of 95%). Also, even more relevantly for the biodegradability issue, whilst at the beginning the NPs enter the cell as small agglomerates, with time the rhodamine seems to diffuse, suggesting, once again, the occurring decomposition of the NPs.

Example 3—Mixed Si—Ti Mesoporous Nanoparticles

Synthesis
  Synthesis of mixed Si—Ti mesoporous nanoparticles (STNPs): 1 g of Pluronic P123 surfactant was dissolved in 25 g of EtOH. The mixture was stirred at 40° C. for 1 hour before the addition of 5 mL ethanol solution of 1.04 g of TEOS and 2.37 g of bis(triethoxysilyl-propyl)disulfide and 1.42 g of titanium isopropoxyde (TIPO). After several minutes, 1.89 g of concentrated HCl was added to the solution. The above reaction mixture was continuously stirred for an additional 1 h and transferred to petri dish. The mother gel was then kept in the oven for 4 days at 35° C. The surfactant template was removed by Soxhlet extraction techniques.

Analysis and Results
  Characterization of the composition of the materials was firstly performed by means of small angle x-ray scattering (SAXS), electron diffraction X-ray spectroscopy (EDX) and thermogravimetric analysis (TGA), in order to confirm the presence of the linker in the structure of the materials.
  The presence of the organic fragments was further sustained by thermogravimetric analysis. From the TGA plot it resulted possible to detect the content of organic material in the materials, characterized by a lower decomposition temperature compared to the inorganic framework.
  Scanning Electron Microscopy (SEM), Transmission Electron Microscopy (TEM) and high resolution Transmission Electron Microscopy (HRTEM) were used to confirm the morphology of the synthesized responsively disintegratable material, as well as the presence of the porous framework.

Example 4—Synthesis of 100 nm Average Diameter SS-Doped SNPs (SS-Doped Mesoporous Silica Nanoparticles) and Tagging with Rhodamine Synthesis of 100 nm SS-Doped SNPs
  Synthesis of SS-doped SNPs (100 nm average diameter): CTAB (250 mg) was dissolved in a solution of distilled water (110 mL), EtOH (10 mL) and NaOH (2M, 0.875 mL) that was heated to 80° C. and stirred vigorously. After complete solubilization of CTAB, TEOS (0.875 mL) and Bis-(triethoxy-silyl-propyl)-disulfide ("BTSPD", 0.390 mL) were added under vigorous stirring. After 6 h the solution was cooled to room temperature and the particles, recovered by centrifugation (20 minutes at 40 krcf), were then purified through a sequence of sonication/centrifugation cycles in EtOH. To remove the surfactants from the pores, the particles were dissolved in acidic EtOH (100 mL, 30 mL of HCl) and refluxed o.n. The particles were hence purified by a sequence of sonication/centrifugation cycles in EtOH and finally dried under vacuum. The material was finally thoroughly characterized by means of XPS, TGA, SAXS, $N_2$ adsorption, SEM and TEM analysis techniques.

Figure 18:
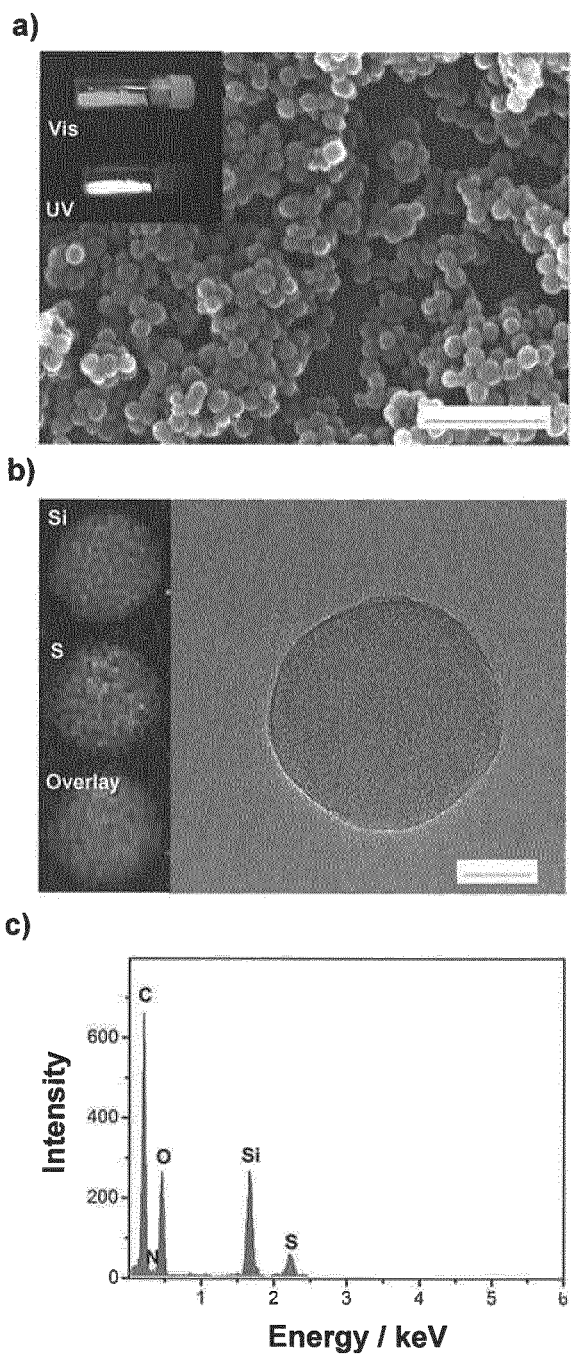
FIG. 18 represents SEM, TEM and EDX characterization of the rhodamine-tagged SS-doped SNPs of Example 4. a) SEM image of SS-doped SNPs. Scale bar=500 nm. Inset: image of the SS-doped SNPs under Vis and UV illumination. b) TEM image of SS-doped SNPs with the corresponding EDX mapping investigation highligthing the presence of S throughout the whole particle structure. Scale bar=20 nm. c) EDX survey analysis of the nanoparticle.
Figure 19:
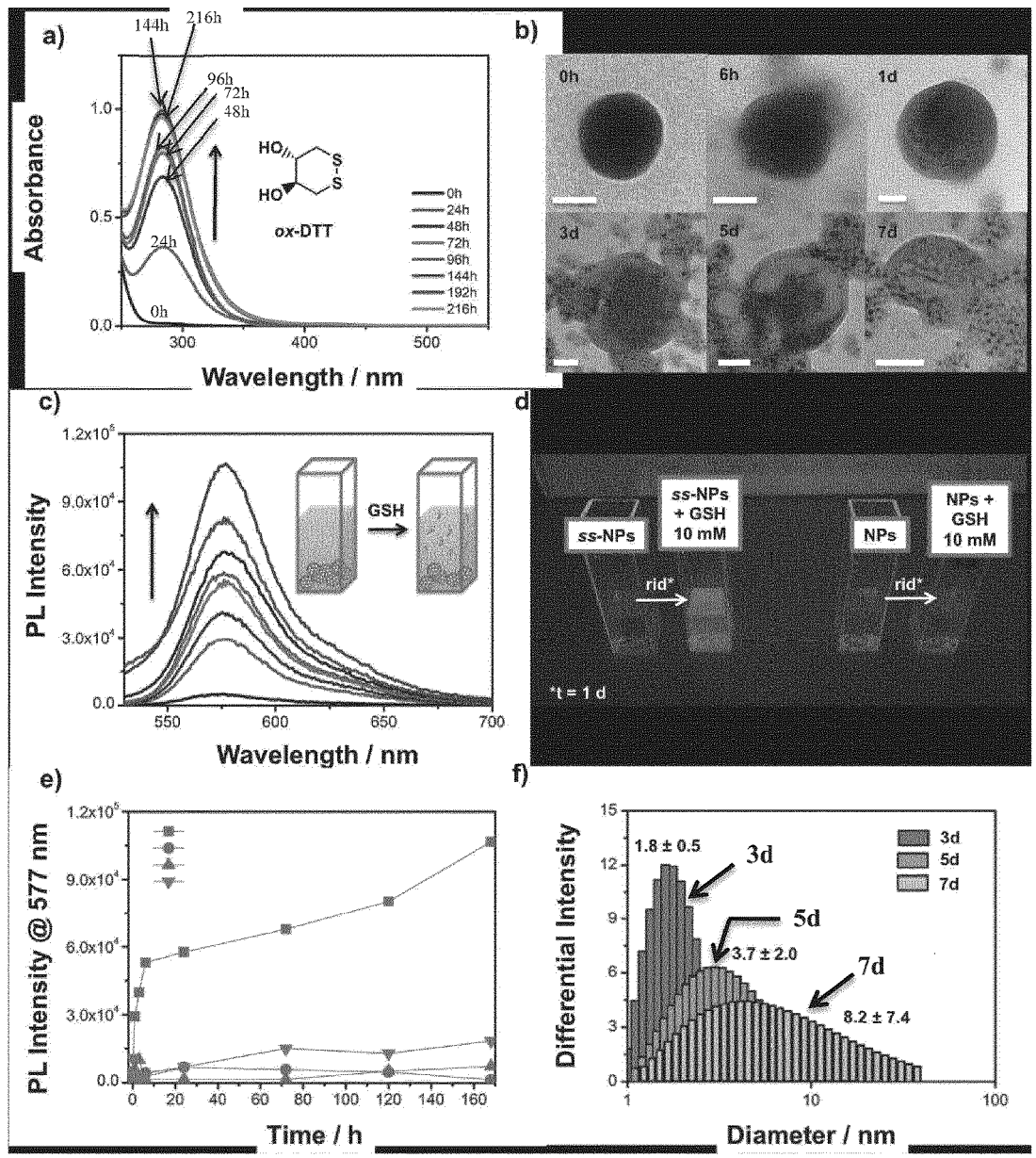
FIG. 19 represents a demonstration (UV, PL, TEM, DLS) of the breaking of the 100 nm SS-doped SNPs of Example 4 in presence of a reducing agent (DTT and GSH). a) DTT (5 mM) titration of SS-doped SNPs (0.1 mg/mL, PBS); b) TEM analysis of a suspension of SS-doped SNPs (0.1 mg/mL, PBS, 37° C.) undergoing GSH (10 mM) reduction (0-168 h). Scale bar=50 nm. Observed structural breakdown within 7 days both in presence of the reducing agent, the reduced glutathione (GSH) in pseudo-physiological conditions (37° C. and PBS); c) PL emission intensity measured at different time points (0-168 h: black 0 h, red 1 h, blue 3 h, magenta 6 h, green 24 h, navy 72 h, violet 120 h, wine 168 h) of the supernatant of centrifuged SS-doped SNPs (0.1 mg/mL, PBS, 37° C.; GSH 10 mM) presenting the broken fragments of the reduced particle; d) image under UV light of the supernatants of SS-doped SNPs and standard NPs before and after GSH reduction (10 mM in PBS, 1 day); e) Plot of the PL intensity vs. time of the supernatants of the centrifuged SS-doped SNPs suspensions (0.1 mg/mL, PBS, 37° C.) in presence of: no GSH, 2 mM GSH, and 10 mM GSH (pink triangle, circle, square); NPs in presence of 10 mM GSH (grey triangle); f) DLS analysis of the supernatant of the of centrifuged dispersion of SS-doped SNPs (0.1 mg/mL, PBS; GSH 10 mM) stirred at 37° C. after 3, 5 and 7 days.
Figure 20:
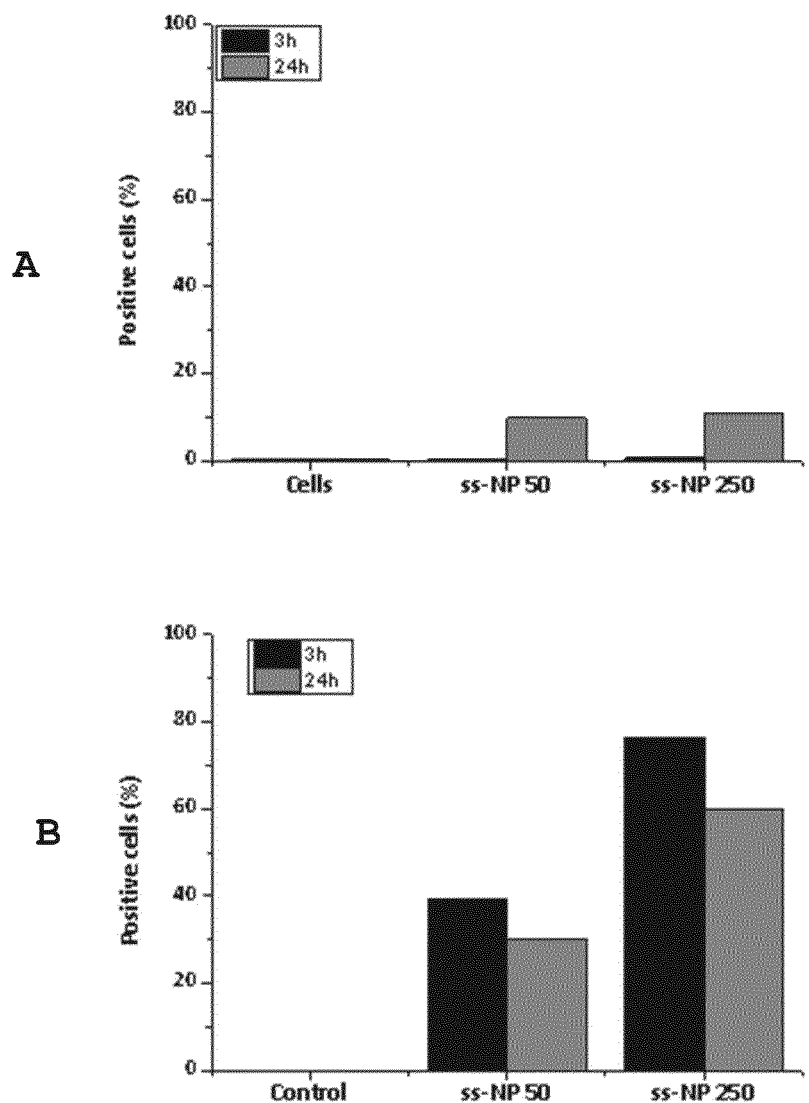
FIG. 20 represents a cytometry study of the uptake of the Rhodamine-tagged 100 nm SS-doped SNPs of Example 4 at two different concentrations: 50 μg/mL and 250 μg/mL. A) in primary cells and B) in Glioma C6 cells. The study shows that the uptake of the SS-doped SNPs is both concentration and time dependent: after 24 h we have less particles than after 3 h, but with the increase of the administered dose we register an increased uptake. In the figures, "ss-NP 50" refers to SS-doped SNPs at 50 μg/mL concentration, and "ss-NP 250" refers to SS-doped SNPs at 250 μg/mL concentration.
Figure 21:
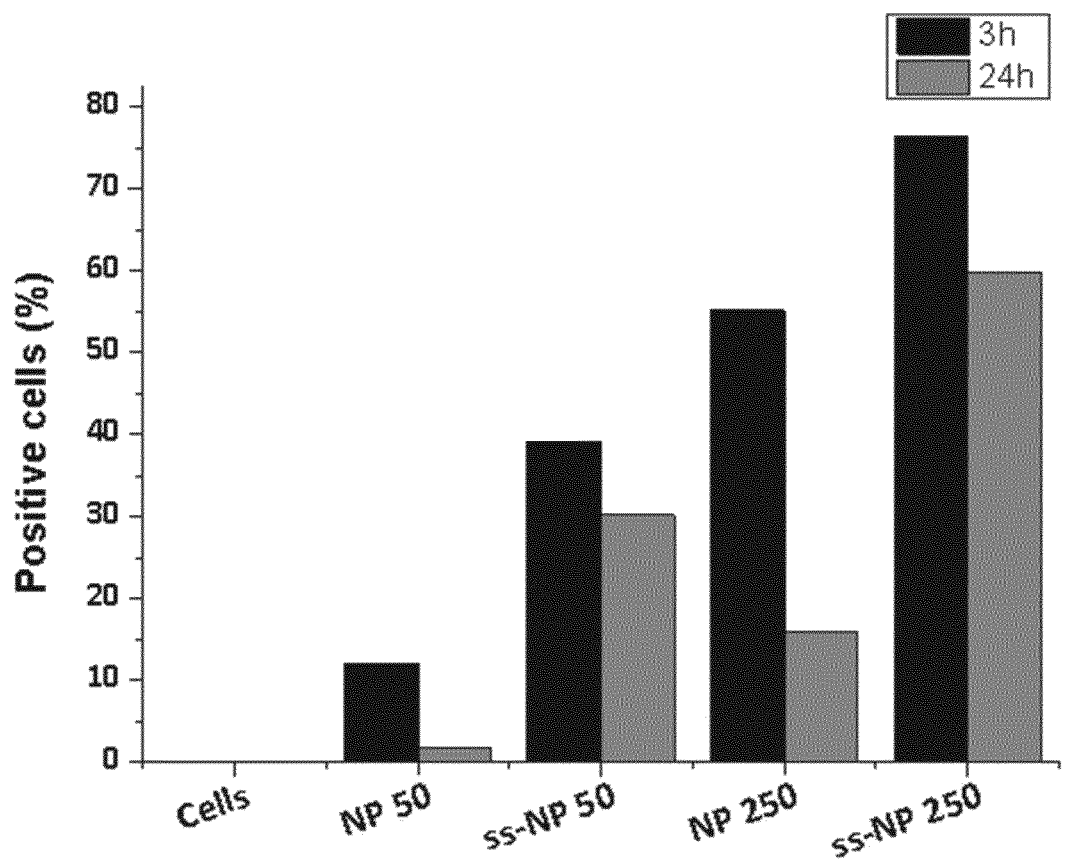
FIG. 21 represents a comparative cytometry study of the uptake of Rhodamine-tagged SS-doped SNPs of Example 4 as compared to standard organosilica nanoparticles (prepared from hydrolysis/condensation of TEOS), at two different concentrations: 50 μg/mL and 250 μg/mL. Uptake of the SS SNPs is significantly higher than the uptake of standard mesoporous silica nanoparticles, independently of the concentration. In the figure, "NP 50" and "NP 250" refer to standard mesoporous silica nanoparticles at 50 μg/mL concentration, and 250 μg/mL concentration, respectively. "ss-NP 50" and "ss-NP 250" refers to SS-doped SNPs at 50 μg/mL concentration, and "ss-NP 250" refer to SS-doped SNPs at 50 μg/mL concentration, and 250 μg/mL concentration, respectively. All particles are of comparable size: 100 nm.
Figure 22:
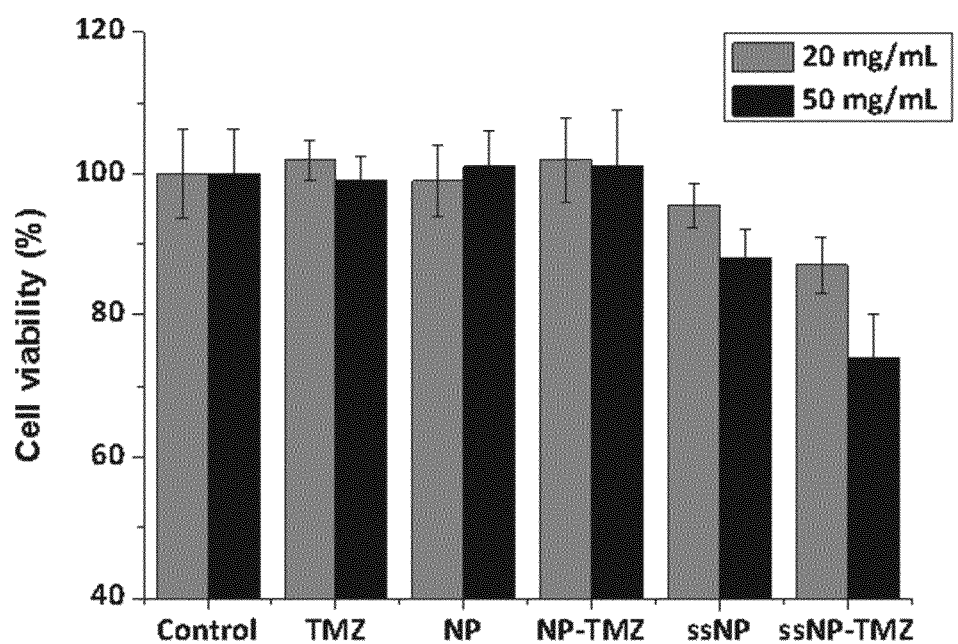
FIG. 22 represents a cell viability screening of the comparative effect of the TMZ-loaded SS-doped SNPs of Example 5 inside Glioma C6 cells, as compared to mesoporous silica nanoparticles not containing S—S cleavable bonds (i.e., standard organosilica nanoparticles prepared from hydrolysis/condensation of TEOS). The results clearly show enhanced efficacy when the TMZ is administered loaded in SS-doped SNPs according to the invention. In the figure, "NP" refers to standard mesoporous silica nanoparticles, while "ssNP" refer to SS-doped SNPs according to the invention.

Synthesis of Rhodamine Tagged SS-Doped SNPs
  Synthesis of S—S doped SNPs (100 nm average diameter): 2.5 mg of rhodamine B isothiocyanate (RITC) were dissolved in EtOH (5 mL) before adding APTES (6 mL). In another flask CTAB (250 mg) was dissolved in a solution of distilled water (110 mL), EtOH (10 mL) and NaOH (2M, 0.875 mL) that was heated to 80° C. and stirred vigorously. The RITC/APTES solution was stirred for 30 minutes before adding TEOS (0.875 mL) and Bis-(triethoxy-silyl-propyl)-disulfide ("BTSPD", 0.390 mL). Once the temperature of the CTAB solution had stabilized, the solution containing the silane sources was added. After 6 h the solution was cooled to room temperature and the particles, recovered by centrifugation (20 minutes at 40 krcf where "rcf" stands for "relative centrifugal force"), were then purified through a sequence of sonication/centrifugation cycles in EtOH. To remove the surfactants from the pores, the particles were dissolved in acidic EtOH (100 mL, 30 mL of HCl) and refluxed o.n. The particles were hence purified by a sequence of sonication/centrifugation cycles in EtOH and finally dried under vacuum. The material was finally thoroughly characterized by means of XPS, TGA, SAXS, N2 adsorption, SEM and TEM analysis techniques. SEM, TEM and EDX characterization of the resulting particles is provided in FIG. 18.

Example 5—Synthesis of SS-Doped SNPs Loaded with Temozolomide (TMZ)

Loading with TMZ

Encapsulation of Temozolomide in the Rhodamine B doped SS-doped SNPs (TMZ⊙ ss-NPs): encapsulation of temozolomide (TMZ) within the pores of the ss-NPs was performed by wet extraction methodology. [22, Vallet-Regi et al., Chem. Mater. 2001, 13, 308] Specifically 30 mg of ss-NPs were dispersed in 9 mL of EtOH by sonication whilst 5 mg of TMZ were dissolved in 1 mL of EtOH. The latter solution was added to the dispersion and the whole introduced in a rotary shaker for 3 days. The mixture was then centrifuged (20 minutes at 40 krcf) and the supernatant removed, before adding to the pelleted particles fresh EtOH (10 mL). The material was again purified by a sequence of sonication/centrifugation cycles in EtOH, and finally dried under vacuum.

Synthesis of Standard Mesoporous Silica Nanoparticles:

Synthesis of Rhodamine B doped NPs: 2.5 mg of RITC were dissolved in EtOH (1.5 mL) before adding APTES (6 µL). In another flask CTAB (250 mg) was dissolved in a solution of distilled water (120 mL) and NaOH (2M, 0.875 mL) that was heated to 80° C. and stirred vigorously. The RITC/APTES solution was stirred for 30 minutes before adding TEOS (1.25 mL). Once the temperature of the CTAB solution had stabilized, the solution containing the silanes was added. After 2 h the solution was cooled to r.t. and the particles, recovered by centrifugation (20 minutes at 40 krcf), were then purified through a sequence of sonication/centrifugation cycles in EtOH. To remove the surfactants from the pores, the particles were dissolved in acidic EtOH (100 mL, 30 µL of HCl) and refluxed o.n. The particles were hence purified by a sequence of sonication/centrifugation cycles in EtOH and finally dried under vacuum.

Loading with TMZ

Encapsulation of Temozolomide in the Rhodamine B doped NPs (TMZ⊙NPs): encapsulation of temozolomide (TMZ) within the pores of the NPs was performed by wet extraction methodology [22]. Specifically 30 mg of NPs were dispersed in 9 mL of EtOH by sonication whilst 5 mg of TMZ were dissolved in 1 mL of EtOH. The latter solution was added to the dispersion and the whole introduced in a rotary shaker for 3 days. The mixture was then centrifuged (20 minutes at 40 krcf) and the supernatant removed, before adding to the pelleted particles fresh EtOH (10 mL). The material was again purified by a sequence of sonication/centrifugation cycles in EtOH, and finally dried under vacuum.

Cytotoxicity with TMZ Loaded Nanoparticles

Cytotoxicity of temozolomide loaded ss-NPs: Glioma C6 cells were seeded in glass cover slips in a 24-well cell culture plate at a density of 1.5×104 cells per well and allowed to grow 24 h. Next the media was removed and fresh media containing temozolomide loaded ss-NPs at different concentrations (20, and 50 µg/mL) was added to the cells and incubated for 3 h at 37° C. in a humidified atmosphere with 5% C02. Temozolomide loaded NPs were also incubated with the cells under the same conditions for comparison purposes. Control cells were treated with equivalets volumes of culture media. After 3 h the cells were trypsinated, centrifuged for 3 min at 1000 rpm and the resultant pellet was re-suspended in 500 mL of culture media for further analysis. Cell viability was measured using CASY® Cell Counter and Analyzer.

Example 6—Synthesis of ICG-Tagged SS-Doped SNPs (SS-Doped SNPs Tagged with Fluorescent Tag Indocyanin Green)

Functionalization with ICG-NHS

Synthesis of Rhodamine B doped SS-doped SNPs functionalized with Indocyanine Green N-succinimidyl ester (ICG-ss-NPs): 20 mg of ss-NPs were dispersed by sonication in DMSO (1 mL) and the solution diluted in toluene (4 mL). In a separate flask, ICG-NHS (0.1 mg) and 3-aminopropyldimethylmethoxysilane (3 µL) were stirred for 2 h in DMSO (1 mL) at r.t. [23, Lu et al., Small 2010, 16, 1794] This solution was hence added to the NPs suspension and the whole kept stirring at r.t. for further 20 h. The mixture was then centrifuged (20 minutes at 40 krcf) and the supernatant removed, before adding to the pelleted particles fresh EtOH (10 mL). The particles were hence purified by a sequence of sonication/centrifugation cycles in EtOH and finally dried under vacuum.

Biodistribution:

Mice were injected with 0.5 mg of ssNPs (tagged with ICG and dispersed in 200 uL of PBS) by intravenous retro-orbital injection. After 3 h from the injection biodistribution was performed. Excretion was monitored up to 48 h, when no more emission was observed in the animals.

Figure 23:
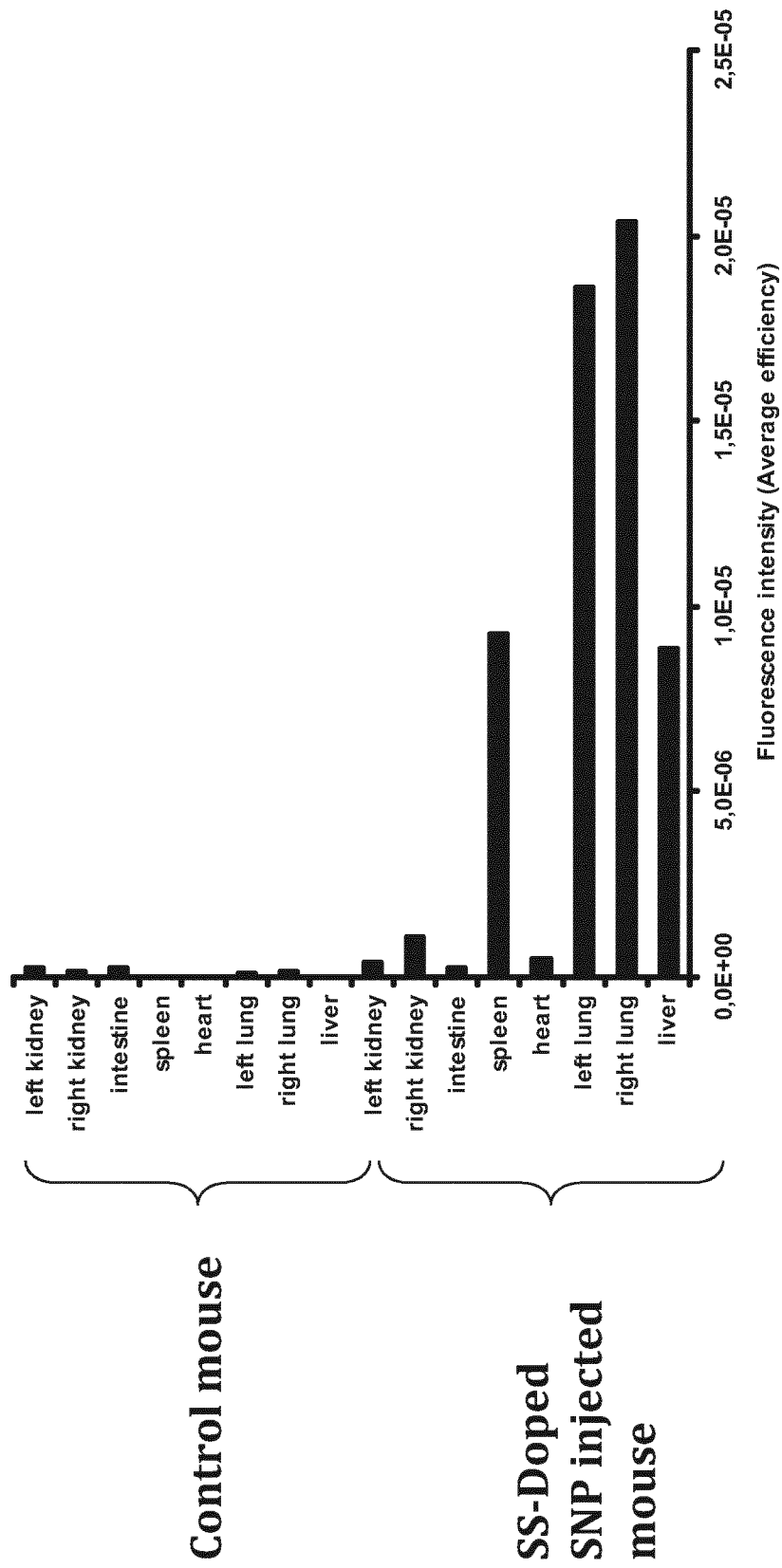
FIG. 23 represents biodistribution assessment of ICG-tagged SS-doped SNPs of Example 6 in mice, (results relative to a non injected mouse) performed 3 h after the retro-orbital injection of 0.5 mg of particles in 200 microL of PBS.

The biodistribution results are shown on FIG. 23: from the examination of the organs the particle seems to accumulate mainly in the lungs and in the liver.

Figure 24:
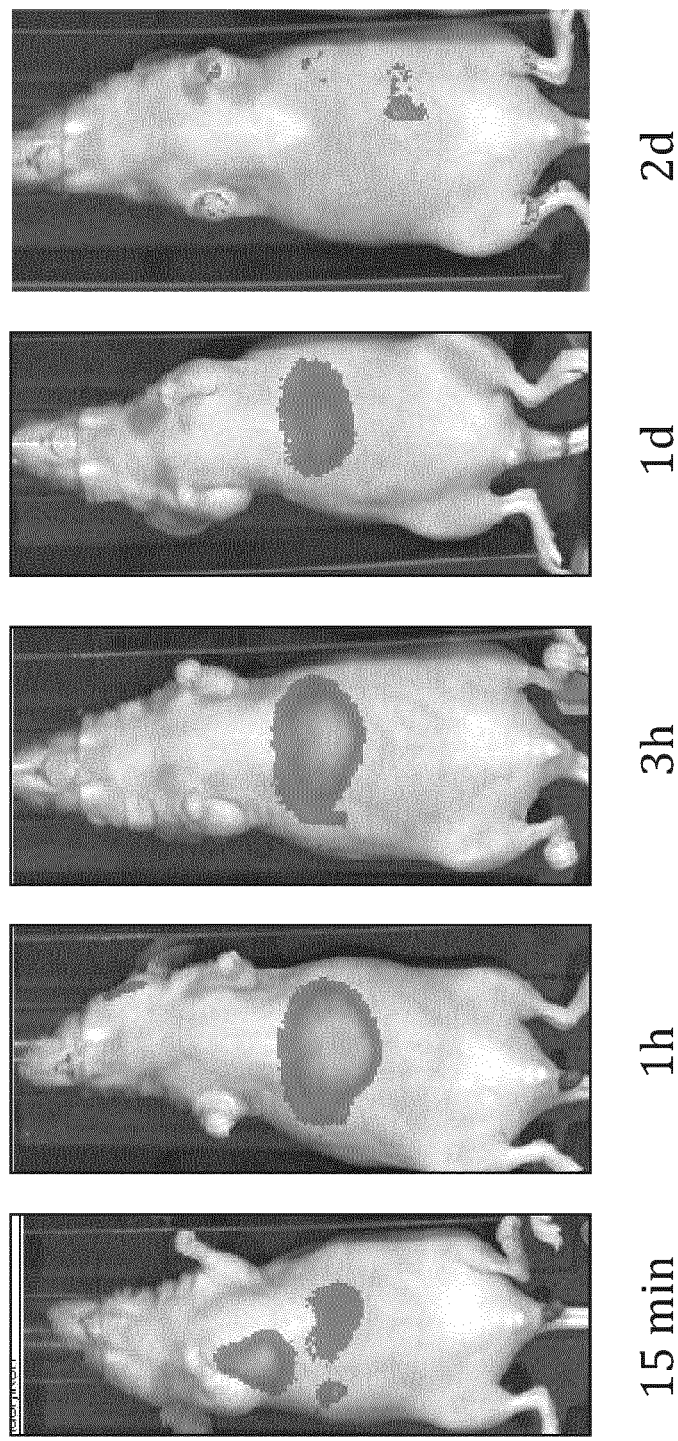
FIG. 24 reports the excretion results of Example 6.

The excretion results are shown on FIG. 24: absence of specific emission already after 2 days.

While we have described a number of embodiments of this invention, it is apparent that our basic examples may be altered to provide other embodiments that utilize the catalysts and methods of this invention. Therefore, it will be appreciated that the scope of this invention is to be defined by the appended claims rather than by the specific embodiments that have been represented by way of example.

LIST OF REFERENCES

[1] a) M. E. Davis, Nature, 2002, 417, 813; b) U. Ciesla, F. Schuth, Micropor. Mesopor. Mat. 1999, 27, 131.

[2] D. Zhao, J. Feng, Q. Huo, N. Melosh, G. H. Fredrickson, B. F. Chmelka, G. D. Stucky, Science, 1998, 279, 548.

[3] T. Linssen, K. Cassiers, P. Cool, E. F. Vansant, Adv. Coll. Interf. Sci. 2003, 103, 121.

[4] T. Asefa, G. A. Ozin, H. Grondey, M. Kruk, M. Jaroniec, Studies Surf. Sci. Catal. 2002, 141, 1.

[5] a) D. S. Shephard, W. Zhou, T. Maschmeyer, J. M. Matters, C. L. Roper, S. Parsons, B. F. G. Johnson, M. J. Duer, Angew. Chem., Int. Ed. 1998, 37, 2719; b) F. de Juan, E. Ruiz-Hitzky, Adv. Mater. 2000, 12, 430; c) K. Cheng, C. C. Landry, J. Am. Chem. Soc. 2007, 129, 9674.

[6] K. J. Shea, D. A. Loy, Chem. Mater. 2001, 13, 3306.

[7] S. Inagaki, S. Guan, T. Ohsuna, O. Terasaki, Nature, 2002, 416, 304.

[8] V. Valtchev, L. Tosheva, Chem. Rev., 2013, 113, 6734.

[9] S. J. Rowan, S. J. Cantrill, G. R. L. Cousins, J. K. M. Sanders, J. F. Stoddart, Angew. Chem. Int. Ed., 2002, 41, 898.

[10] M. Kruk, Acc. Chem. Res., 2012, 45, 1678.
[11] F. Hoffmann, M. Cornelius, J. Morell, M. Fröba, Angew. Chem. Int. Ed. 2006, 45, 3216-3251.
[12] S. V. M. de Moraes, J. B. Passos, P. Schossler, E. B. Caramão, C. C. Moro, T. M. H. Costa, E. V. Benvenutti, Talanta, 2003, 59, 1039.
[13] M. He, J. Bu, X. Yuan, Integrated Optics: Devices, Materials, and Technologies X. Edited by Sidorin, Yakov; Waechter, Christoph A. Proceedings of the SPIE, 2006, 6123, 130.
[14] M. Graffner-Nordberg, K. Sjödin, A. Tunek, A. Hallberg, Chem. Pharm. Bull., 1998, 46, 591.
[15] M. Kobayashi, Y. Fujiwara, M. Goda, H. Komeda, S. Shimizu, PNAS, 1997, 94, 11986.
[16] C. Lopreore, L. D. Byers, Arch. Biochem. Biophys., 1998, 349, 299.
[17] E. Khalikova, P. Susi, T. Korpela, Microbiol. Mol. Biol. Rev., 2005, 69, 306.
[18] R. Weissleder, C.-H. Tung, U. Mahmood, A. Bogdanov Jr., Nat. Biotech., 1999, 17, 375.
[19] M. Yamashita, A. Tani, F. Kawai, Appl. Microbiol. Biotechnol., 2004, 66, 174.
[20] S. H. Lee, W. S. Song, Text. Res. J., 2013, 83, 229.
[21] P. D. Hsu, D. A. Scott, J. Weinstein, F. A. Ran, S. Konermann, V. Agarwala, Y. Li, E. J. Fine, X. Wu, O. Shalem, T. J Cradick, L. A. Marraffini, G. Bao, F. Zhang, Nat. Biotech., 2013, 31, 827; M. Furutani, K. Ito, Y. Oku, Y. Takeda, K. Igarashi, Microbiol. Immunol., 1990, 34, 387.
[22] Vallet-Regi et al., Chem. Mater. 2001, 13, 308.
[23] Lu et al., Small 2010, 16, 1794.

The invention claimed is:

1. A disintegratable porous organometaloxide material comprising a porous three-dimensional framework of metal-oxygen bonds, wherein at least a subset of metal atoms in the material's framework are connected to at least another metal atom in the framework through a linker having one of the following structures:

*—$R^1$-L-$R^2$—*,

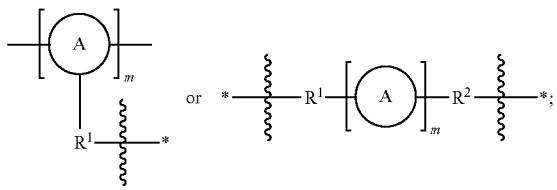

wherein:
each occurrence of * denotes a point of attachment to a metal atom in the material's framework;
A represents a monomer of a responsively cleavable fragment of biological/biodegradable polymer selected from carbohydrates, peptides, and synthetic biodegradable polyethyleneglycol or polylactide polymers;
m is an integer from 2 to 10000 and m represents the number of monomers in the fragment of biological/biodegradable polymer;
L represents a responsively cleavable covalent bond selected from boronic acid derivatives, diselenide, ester, amide, acetal, ketal, anhydride, thiourea, hydrazone, or oxyme, and
$R^1$ and $R^2$ independently represent an optionally substituted C1-20alkylenyl moiety, an optionally substituted ethylenyl moiety, —C≡C— or an optionally substituted phenyl moiety, wherein the C1-20alkylenyl, or ethylenyl moiety may bear one or more substituents selected from halogen or —OR where R may represent H or C1-6alkyl, and the phenyl moiety may bear one or more substituents independently selected from halogen, C1-6alkyl, —$NO_2$, —CN, isocyano, —$OR^P$, —$N(R^P)_2$ wherein each occurrence of $R^P$ independently represents H or C1-6alkyl.

2. The material of claim 1, wherein the three-dimensional framework of metal-oxygen bonds is mesoporous, microporous, macroporous or mixed mesoporous-macroporous.

3. The material of claim 1, wherein the linker has the structure *—$R^1$-L-$R^2$—*, and the subset of metal atoms in the material's framework that are connected to the linker *—$R^1$-L-$R^2$—*, represent at least 30% of the metal atoms present in the porous organometaloxide material.

4. The material of claim 1, wherein the linker represents a responsively cleavable fragment of biological/biodegradable polymer selected from carbohydrates, peptides and synthetic biodegradable polyethyleneglycol or polylactide polymers, and the linker has the structure

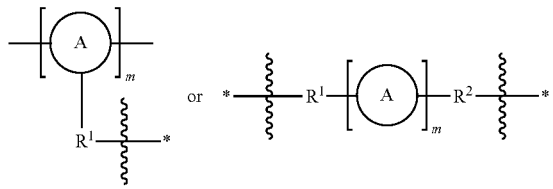

wherein A, m, $R^1$ and $R^2$ are as defined in claim 1.

5. The material of claim 1, wherein the metal is selected from Si, Ti or Zr, or any combination of at least two of these metals.

6. The material of claim 1, wherein the material contains 90.0-100% Si, 90.0-100% Ti or 90.0-100% Zr as metal, wherein the % are based on the number of available metal sites in the framework.

7. The material of claim 1, wherein the material is a Si—Ti mixed-metal organometaloxide material containing 0.1-50.0% Si and 0.1-50.0% Ti, the % sum of Si and Ti adding to 100% the number of available metal sites in the framework.

8. The material of claim 1, wherein in the linker represents *—$R^1$-L-$R^2$—*, $R^1$ and $R^2$ are identical, and each represent —$CH_2$—, —$(CH_2)_2$—, —$(CH_2)_3$—, —$(CH_2)_4$—, or phenyl.

9. The material of claim 1, said material comprising in its pores or at its surface at least one marker and/or cosmetically or pharmaceutically active principle.

10. The material of claim 9, wherein the marker is selected from a contrast agent, a tracer, a radioactive marker, a fluorescent marker, a phosphorescent marker, a magnetic resonance imaging agent or a positron emission tomography agent.

11. The material of claim 1, wherein the material is in the form of a monolith, a thin or thick film, a powder, nanoparticles, or spherical, cubic, cylindrical or disc-like particles.

12. A method for preparing a material of claim 1, comprising steps of:
a) Producing a supramolecular template by mixing a suitable surfactant and an aqueous solvent;

b) Adding a mixture of a precursor $M(X^A)_4$ and a selected precursor having the structure:

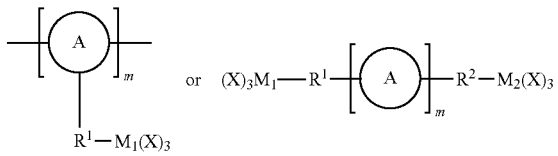

in an aqueous solvent under alkaline conditions; thereby coating the supramolecular template with an organometaloxide sol-gel mixture obtained by hydrolysis-condensation of metal alkoxide; and c) Removing the supramolecular template; thereby producing a porous organometaloxide nanoparticles comprising a porous three-dimensional framework of metal-oxygen bonds, wherein at least a subset of metal atoms in the material's framework are connected to at least another metal atom in the framework through a linker having one of the following structures:

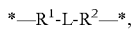

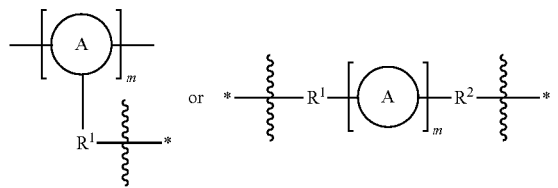

wherein:
each occurrence of * denotes a point of attachment to a metal atom in the material's framework;
A represents a monomer of a responsively cleavable fragment of biological/biodegradable polymer selected from carbohydrates, peptides, and synthetic biodegradable polyethyleneglycol or polylactide polymers;
m is an integer from 2 to 10000 and m represents the number of monomers in the fragment of biological/biodegradable polymer;
M and each occurrence of $M_1$ and $M_2$ independently represents a metal selected from Si, Ti and Zr;
each occurrence of X and $X^A$ independently represents a hydrolysable or nonhydrolyzable group, provided that on each occurrence of $M_1$ and $M_2$, at least one occurrence of X represents a hydrolysable group and at least two occurrences of $X^A$ in the precursor $M(X^A)_4$ independently represent a hydrolysable group; wherein (i) when X or $X^A$ represents a nonhydrolyzable group, it may be selected from an optionally substituted C1-20alkyl, C2-20alkenyl or C2-20alkynyl moiety, an optionally substituted C1-20heteroalkyl, C2-20heteroalkenyl or C2-20heteroalkynyl moiety, or an optionally substituted phenyl moiety, wherein the substituents on the phenyl, alkyl, alkenyl, alkynyl, heteroalkyl, heteroalkenyl and heteroalkynyl moieties may be independently selected from halogen, —$NO_2$, —CN, isocyano, C1-6alkoxy, an oxirane/epoxyde moiety, —$N(R)_2$ wherein each occurrence of R is independently selected from H or C1-6alkyl; and (ii) when X or $X^A$ represents a hydrolysable group, it may be selected from a C1-6alkoxy, C1-6acyloxy, halogen or amino moiety;
L represents a responsively cleavable covalent bond selected from boronic acid derivatives, diselenide, ester, amide, acetal, ketal, anhydride, thiourea, hydrazone, or oxyme ; and
$R^1$ and $R^2$ independently represent an optionally substituted C1-20alkylenyl moiety, an optionally substituted ethylenyl moiety, —C≡C— or an optionally substituted phenyl moiety, wherein the C1-20 alkylenyl, or ethylenyl moiety may bear one or more substituents selected from halogen or —OR where R may represent H or C1-6alkyl, and the phenyl moiety may bear one or more substituents independently selected from halogen, C1-6alkyl, —$NO_2$, —CN, isocyano, —$OR^P$, —$N(R^P)_2$ wherein each occurrence of $R^P$ independently represents H or C1-6alkyl.

13. The method of claim 12, wherein the ratio of equivalents $(X)_3M_1$-$R^1$-L-$R^2$-$M_2(X)_3$/$M(X^A)_4$ is one listed in the table below:

| $M(X^A)_4$ | $(X)_3M_1$-$R^1$-L-$R^2$-$M_2(X)_3$ | $(X)_3M_1$-$R^1$-L-$R^2$-$M_2(X)_3$ | % doping |
|---|---|---|---|
| 0.70 eq. | 0.30 eq.† | 0.15 eq. # | 30% |
| 0.60 eq. | 0.40 eq.† | 0.20 eq. # | 40% |
| 0.50 eq. | 0.50 eq.† | 0.25 eq. # | 50% |
| 0.40 eq. | 0.60 eq.† | 0.30 eq. # | 60% |
| 0.30 eq. | 0.70 eq.† | 0.35 eq. # | 70% |
| 0.20 eq. | 0.80 eq.† | 0.40 eq. # | 80% |
| 0.10 eq. | 0.90 eq.† | 0.45 eq. # | 90% |
| — | 1 eq.† | 0.5 eq. # | 100% |

† equivalents expressed in terms of metal atoms ($M_1$ and $M_2$) introduced by the bivalent starting material $(X)_3M_1$-$R^1$-L-$R^2$-$M_2(X)_3$ in the final organometaloxide material.
equivalents expressed in terms of responsively cleavable bond L introduced by the bivalent starting material $(X)_3M_1$-$R^1$-L-$R^2$-$M_2(X)_3$ in the final organometaloxide material.

14. A method for preparing a material of claim 1 being 100% doped, comprising steps of:
a) Producing a supramolecular template by mixing a suitable surfactant and an aqueous solvent;
b) Adding a selected precursor having the structure:

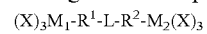

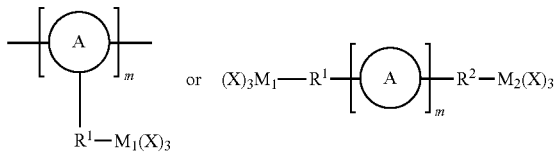

in an aqueous solvent under alkaline conditions; thereby coating the supramolecular template with an organometaloxide sol-gel mixture obtained by hydrolysis-condensation of metal alkoxide; and
c) Removing the supramolecular template; thereby producing a porous organometaloxide material comprising a porous three-dimensional framework of metal-oxygen bonds, wherein at least a subset of metal atoms in the material's framework are connected to at least another metal atom in the framework through a linker having one of the following structures:

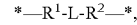

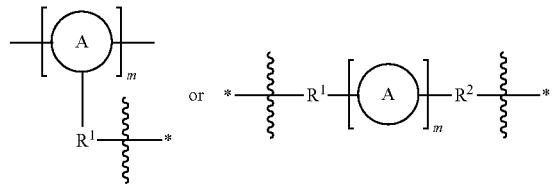

wherein:
each occurrence of * denotes a point of attachment to a metal atom in the material's framework;
A represents a monomer of a responsively cleavable fragment of biological/biodegradable polymer selected from carbohydrates, peptides and synthetic biodegradable polyethyleneglycol or polylactide polymers;
m is an integer from 2 to 10000 and m represents the number of monomers in the fragment of biological/biodegradable polymer;
each occurrence of $M_1$ and $M_2$ independently represents a metal selected from Si, Ti and Zr;
each occurrence of X independently represents a hydrolysable or nonhydrolyzable group, provided that on each occurrence of $M_1$ and $M_2$, at least one occurrence of X represents a hydrolysable group; wherein (i) when X represents a nonhydrolyzable group, it may be selected from an optionally substituted C1-20 alkyl, C2-20 alkenyl or C2-20 alkynyl moiety, an optionally substituted C1-20 heteroalkyl, C2-20 heteroalkynyl or C2-20 heteroalkynyl moiety, or an optionally substituted phenyl moiety, wherein the substituents on the phenyl, alkyl, alkenyl, alkynyl, heteroalkyl, heteroalkenyl and heteroalkynyl moieties may be independently selected from halogen, —$NO_2$, —CN, isocyano, C1-6 alkoxy, an oxirane/epoxyde moiety, —$N(R)_2$ wherein each occurrence of R is independently selected from H or C1-6 alkyl; and (ii) when X represents a hydrolysable group, it may be selected from a C1-6 alkoxy, C1-6 acyloxy, halogen or amino moiety;
L represents a responsively cleavable covalent bond selected from boronic acid derivatives, diselenide, ester, amide, acetal, ketal, anhydride, thiourea, hydrazone, or oxyme ; and
$R^1$ and $R^2$ independently represent an optionally substituted C1-20alkylenyl moiety, an optionally substituted ethylenyl moiety, —C≡C— or an optionally substituted phenyl moiety, wherein the C1-20alkylenyl, or ethylenyl moiety may bear one or more substituents selected from halogen or —OR where R may represent H or C1-6alkyl, and the phenyl moiety may bear one or more substituents independently selected from halogen, C1-6alkyl, —$NO_2$, —CN, isocyano, —$OR^P$, —$N(R^P)_2$ wherein each occurrence of $R^P$ independently represents H or C1-6alkyl.

15. The method of claim 12, wherein the metal is Si.

16. The method of claim 12, wherein the metal is Si and $M(X^A)_4$ represents a tetraalkoxysilane such as tetramethoxysilane, tetraethoxysilane and tetrapropoxysilane, preferably tetraethoxysilane (TEOS).

17. The method of claim 12, wherein the surfactant is a cationic surfactant, an anionic surfactant, a non-ionic surfactant; preferably a cationic surfactant such as octadecyl trimethyl ammonium bromide, hexadecyl trimethyl ammonium bromide, tetradecyl trimethyl ammonium bromide, dodecyl trimethyl ammonium bromide, decyl trimethyl ammonium bromide, octyl trimethyl ammonium bromide, hexyl trimethyl ammonium bromide and other quaternary ammonium salt-type cationic surfactants.

18. The method of claim 14, wherein the aqueous solvent comprises an alcohol, such as methanol or ethanol.

19. The method of claim 14, wherein linker comprises a peptide bond, or a carbohydrate moiety, as responsively cleavable bond or moiety.

20. The method of claim 12, wherein the precursor having the structure $(X)_3M-R^1-L-R^2-M(X)_3$ is produced in situ.

21. A porous organometaloxide material obtainable by a method of claim 12.

22. A method of preparing a medicament comprising incorporating into the medicament a porous organometaloxide material of claim 1 wherein the material comprises in its pores or at its surface at least one pharmaceutically active principle.

23. A medical imaging method comprising providing a porous organometaloxide material of claim 1 wherein the material comprises in its pores or at its surface at least one marker; and performing medical imaging using the material.

24. A method of preparing a cosmetic, catalytic, paint, ink, photovoltaic, or optical coating composition comprising providing a material according to claim 1 and at least one carrier, and incorporating the material into the composition.

25. A method of treating a condition or disease comprising administering to a subject in need thereof a disintegratable porous organometaloxide material according to claim 1, appropriately loaded on its surface or in its pore with a drug moiety adapted for such treatment.

* * * * *